United States Patent
Galli et al.

(10) Patent No.: US 10,064,876 B2
(45) Date of Patent: Sep. 4, 2018

(54) BILE ACID RECEPTOR AGONISM FOR TREATING ADDICTION

(71) Applicant: Vanderbilt University, Nashville, TN (US)

(72) Inventors: Aurelio Galli, Brentwood, TN (US); Heinrich J. G. Matthies, Nashville, TN (US); Naji N. Abumrad, Nashville, TN (US); India A. Reddy, Nashville, TN (US); Charles Robb Flynn, Nashville, TN (US); Kevin Erreger, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 15/218,976

(22) Filed: Jul. 25, 2016

(65) Prior Publication Data

US 2017/0020894 A1    Jan. 26, 2017

Related U.S. Application Data

(60) Provisional application No. 62/196,776, filed on Jul. 24, 2015.

(51) Int. Cl.
*A61K 31/575* (2006.01)
*A61K 31/00* (2006.01)

(52) U.S. Cl.
CPC .......... *A61K 31/575* (2013.01); *A61K 31/00* (2013.01)

(58) Field of Classification Search
CPC ............................ A61K 31/575; A61K 31/00
USPC ....................................................... 514/182
See application file for complete search history.

(56) References Cited

PUBLICATIONS

Hirschfield et al. Gastroenterology, 2015, 148, 751-761.*
Ahmad, N. N., et al. Int. J. Obes. (Lond.) 37, 1553-1559 (2013).
Anders, S. & Huber, W. Genome Biol. 11, R106 (2010).
Bentley, D. R. et al. Nature 456, 53-59 (2008).
Calipari, E.S., et al. Proc Natl Acad Sci U S A 113(10):2726-31 (2016).
Dekaney, C. M. et al. Surgery 144, 174-181 (2008).
Dowd, S. E., et al. Foodborne Pathog. Dis. 5, 459-472 (2008).
Dunn JP, et al. Diabetes Care 2012; 35:137-142.
Fabbrini E, et al. Gastroenterology 2010; 139:448-455.
Fiorucci S, et al. (2009). Trends Pharmacol Sci. 30(11):570-580.
Fiorucci S, et al. (2011). Mini Rev Med Chem. 11(9):753-762.
Flynn, C.R., et al. Nature communications 6:7715 (2015.
Furet, J. P. et al. Diabetes 59, 3049-3057 (2010).
Degirolamo, C., et al. Cell Rep. 7, 12-18 (2014).
Goodrich, J. K. et al. Cell 159, 789-799 (2014).
Graham, D.L., et al. Mol Psychiatry 18:961-962 (2013).
Grueter, B.A., et al. Curr Opin Neurobiol 22:545-551 (2012).
Grueter, B.A., et al. Nat Neurosci 13:1519-1525 (2010).
Guo, Y. et al. Genomics 103, 323-328 (2014).
Guo, Y., et al. Biomed. Res. Int. 2014, 248090 (2014).
Hagio M, et al. J Lipid Res 2009; 50:173-180.
Hardcastle, T. J. & Kelly, K. A. BMC Bioinformatics 11, 422 (2010).
Hernandez, L., et al. Life Sci 42:1705-1712 (1988).
Joffe, M.E., et al. Cognitive science 5:151-171 (2014).
Johnson, P.M. & Kenny, P.J. Nat Neurosci 13:635-641 (2010).
Keitel, V., et al. Glia 58:1794-1805 (2010).
Kohli, R. etal. J. Clin. Endocrinol. Metab. 98, E708-E712 (2013).
Kuipers, F., et al. Nature reviews. Endocrinology 10:488-498 (2014).
Li, F. et al. Nat. Commun. 4, 2384 (2013).
Li, S. et al. Cell Metab. 20, 320-332 (2014).
Liou, A. P. et al. Sci. Transl. Med. 5, 178ra141 (2013).
Lu, T. T. et al. Mol. Cell 6, 507-515 (2000).
Maruyama, T., et al. J Endocrinol 191:197-205 (2006).
Nakatani, H. et al. Metabolism 58, 1400-1407 (2009).
Narayanan NS, et al. (2010). Front Neuroendocrinol. 31(1):104-112.
Patti, M. E. et al. Obesity (Silver Spring) 17, 1671-1677 (2009).
Pellicciari R, et al. (2007). J Med Chem. 50(18):4265-4268.
Reddy IA, et al. (2014). ACS Chem Neurosci. 5(10):943-951.
Reddy IA, et al. (2014). Neurochem Int. 73:49-55.
Roberts, D.C.S. & Koob, G.F. Pharmacology, Biochemistry, and Behavior 17:901-904 (1982).
Robertson, S.D., et al. J Neurosci 30:11305-11316 (2010).
Robinson TE, et al. Philos Trans R Soc Lond B Biol Sci. 363(1507):3137-3146 (2008).
Robinson, M. D., et al. Bioinformatics 26, 139-140 (2010).
Rodrigues CM, et al. Biomed Chromatogr 10:1-5 (1996).
Sayin, S. I. et al. Cell Metab. 17, 225-235 (2013).
Schmitz, Y., et al. J Neurosci 22:8002-8009 (2002).
Simonen, M. et al. Obes.Surg. 22, 1473-1480 (2012).

(Continued)

*Primary Examiner* — Yevgeny Valenrod
(74) *Attorney, Agent, or Firm* — Meunier Carlin & Curfman LLC

(57) ABSTRACT

Compositions and methods for treating addiction in a subject are disclosed. In particular, compositions and methods for treating addiction to a dopaminergic psychostimulant are disclosed. In some embodiments, addiction is treated by agonizing bile acid receptors in the subject. For example, in some embodiments, the method comprises administering to the subject a therapeutically effective amount of a composition comprising a therapeutically effective amount of a bile acid receptor agonist. In some embodiments, the method comprises surgically diverting bile acids in the subject in a manner suitable to increase circulating bile acids in the subject.

4 Claims, 76 Drawing Sheets

Specification includes a Sequence Listing.

(56) References Cited

PUBLICATIONS

Steinert, R. E. et al. Obesity (Silver Spring) 21, E660-E668 (2013).
Svensson, P. A. et al. Biochem. Biophys. Res. Commun. 433, 563-566 (2013).
Tataranni PA, et al. Am J Clin Nutr 1995; 62:730-734.
Thomas, C. et al. Cell Metab. 10, 167-177 (2009).
Turnbaugh, P. J. et al. Nature 487, 47-48 (2012).
Vassileva, G., et al. Biochem J 398:423-430 (2006).
Volkow, N. D., et al. Biol Psychiatry 73:811-818 (2013).
Vorhees, et al. Nat Protoc. 1(2):848-858 (2006).
Watanabe, M. et al. Nature 439, 484-489 (2006).
Weir, J. B. J. Physiol. 109, 1-9 (1949).
Wolf, M.E. & Ferrario, C.R. Neurosci Biobehav Rev 35:185-211 (2010).
Yin, D. P. et al. Ann. Surg. 254, 73-82 (2011).
International Search Report and Written Opinion, issued in International Application No. PCT/US2016/043891, dated Oct. 17, 2016.
Anonymous, "Rote Liste 2004".
Bala, et al. Frontiers in Physiology vol. 5 (2014).
Han, et al. Obes Surg vol. 25 (2015).
Kumar, et al. The FASEB Journal vol. 29 (2015).
Lee, et al. Endocrine Reviews vol. 31 (2010).
Stanwood, et al. Neuropsychopharmacology vol. 38 (2013).

\* cited by examiner

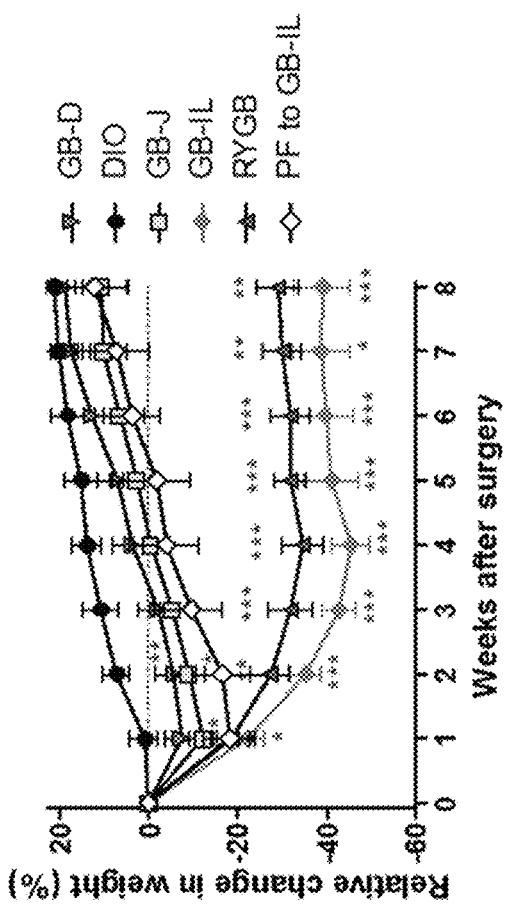
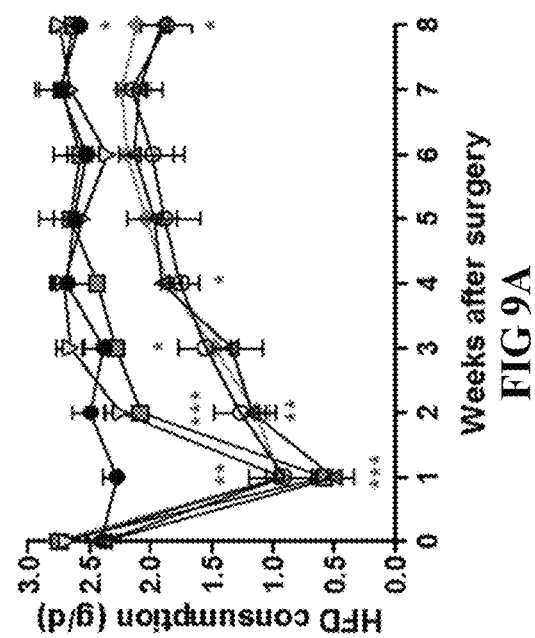
FIG 9B
FIG 9A

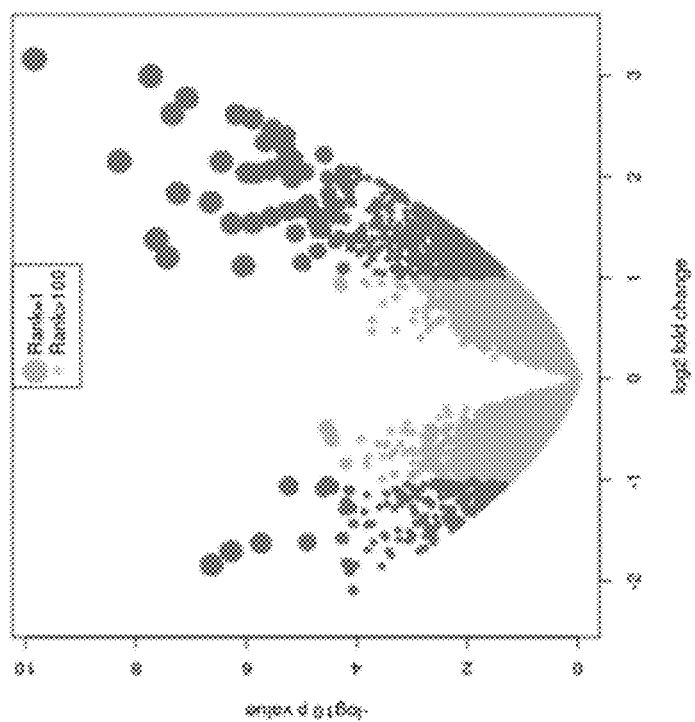
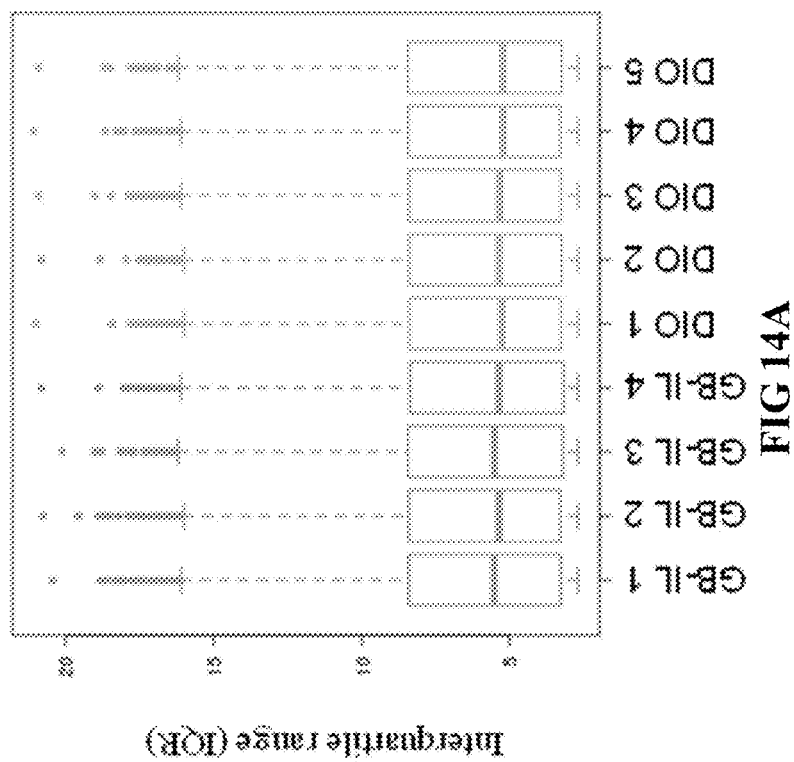
FIG 14B
FIG 14A

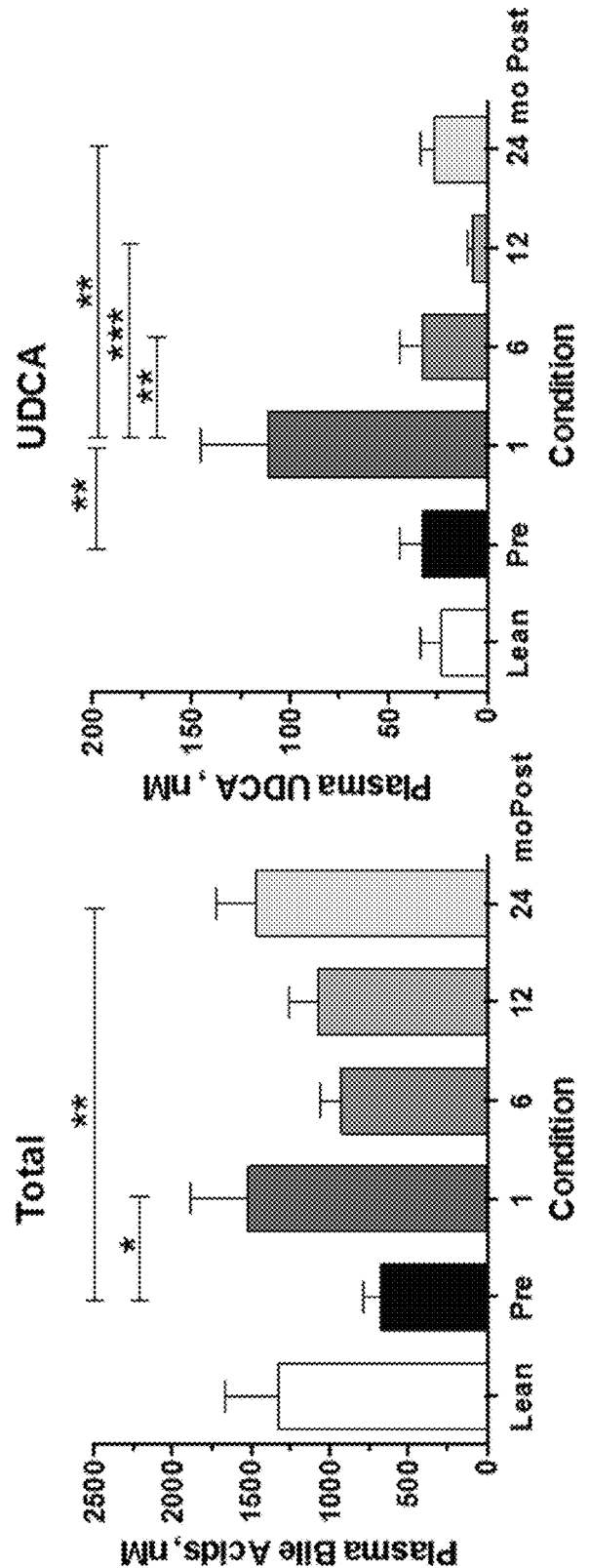

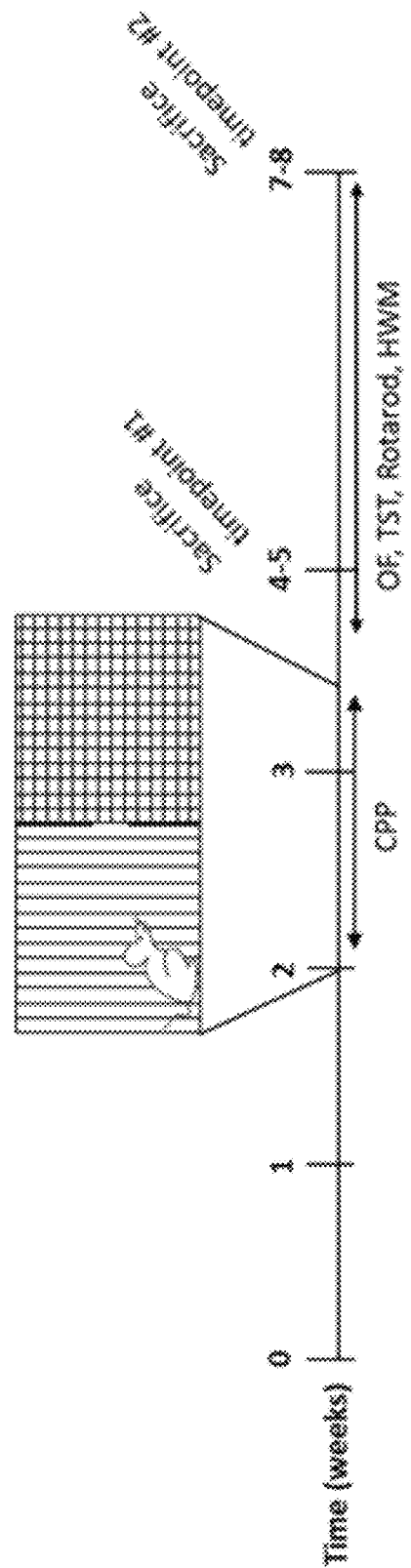

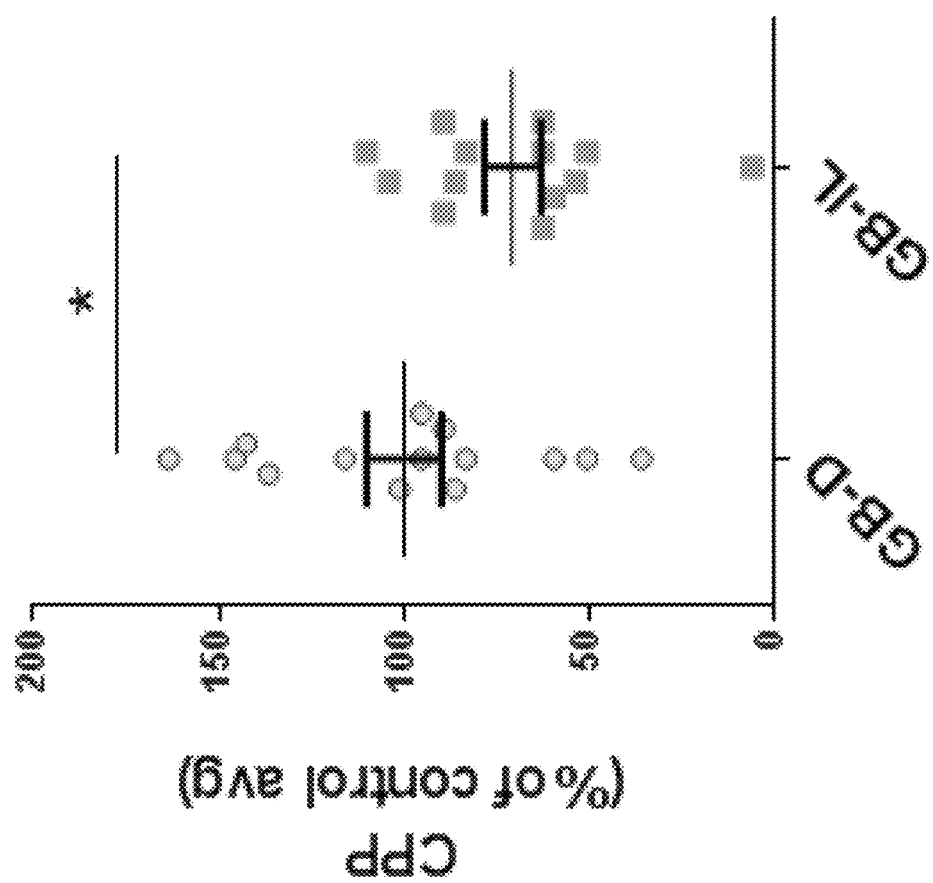

SEQUENCE LISTING

```
<160> NUMBER OF SEQ ID NOS: 24

<210> SEQ ID NO 1
<211> LENGTH: 21
<212> TYPE: DNA
<213> ORGANISM: Artificial Sequence
<220> FEATURE:
<223> OTHER INFORMATION: synthetic construct

<400> SEQUENCE: 1
accctggatc agctcctgga t                                           21
```

<210> SEQ ID NO 2
<211> LENGTH: 20
<212> TYPE: DNA
<213> ORGANISM: Artificial Sequence
<220> FEATURE:
<223> OTHER INFORMATION: synthetic construct

<400> SEQUENCE: 2
gttctcagct agcagcttgg                                                    20

<210> SEQ ID NO 3
<211> LENGTH: 22
<212> TYPE: DNA
<213> ORGANISM: Artificial Sequence
<220> FEATURE:
<223> OTHER INFORMATION: synthetic construct

<400> SEQUENCE: 3
ggaaacctgt tagttctcag gc                                                 22

<210> SEQ ID NO 4
<211> LENGTH: 21
<212> TYPE: DNA
<213> ORGANISM: Artificial Sequence
<220> FEATURE:
<223> OTHER INFORMATION: synthetic construct

<400> SEQUENCE: 4 gtggacccccc atatagtctc c                                                 21

<210> SEQ ID NO 5
<211> LENGTH: 20
<212> TYPE: DNA
<213> ORGANISM: Artificial Sequence
<220> FEATURE:
<223> OTHER INFORMATION: synthetic construct

<400> SEQUENCE: 5
ctgccaagga tgctaatgca                                                    20

<210> SEQ ID NO 6
<211> LENGTH: 21
<212> TYPE: DNA
<213> ORGANISM: Artificial Sequence
<220> FEATURE:
<223> OTHER INFORMATION: synthetic construct

<400> SEQUENCE: 6
cgatggctac cctttgcttc t                                                  21

<210> SEQ ID NO 7
<211> LENGTH: 21
<212> TYPE: DNA
<213> ORGANISM: Artificial Sequence
<220> FEATURE:
<223> OTHER INFORMATION: synthetic construct

<400> SEQUENCE: 7
accacttgct ccacactgct t                                                  21

<210> SEQ ID NO 8
<211> LENGTH: 21
<212> TYPE: DNA
<213> ORGANISM: Artificial Sequence
<220> FEATURE:

<223> OTHER INFORMATION: synthetic construct

<400> SEQUENCE: 8
cgttcctgag tcaacccaca t                                           21

<210> SEQ ID NO 9
<211> LENGTH: 23
<212> TYPE: DNA
<213> ORGANISM: Artificial Sequence
<220> FEATURE:
<223> OTHER INFORMATION: synthetic construct

<400> SEQUENCE: 9
tcccactttt cggagacagt aac                                         23

<210> SEQ ID NO 10
<211> LENGTH: 23
<212> TYPE: DNA
<213> ORGANISM: Artificial Sequence
<220> FEATURE:
<223> OTHER INFORMATION: synthetic construct

<400> SEQUENCE: 10
actgaggacc ttgaagtctt gga                                         23

<210> SEQ ID NO 11
<211> LENGTH: 20
<212> TYPE: DNA
<213> ORGANISM: Artificial Sequence
<220> FEATURE:
<223> OTHER INFORMATION: synthetic construct

<400> SEQUENCE: 11
atgaccacct gctccagctt                                             20

<210> SEQ ID NO 12
<211> LENGTH: 20
<212> TYPE: DNA
<213> ORGANISM: Artificial Sequence
<220> FEATURE:
<223> OTHER INFORMATION: synthetic construct

<400> SEQUENCE: 12
gcctttgtag ggcaccttgt                                             20

<210> SEQ ID NO 13
<211> LENGTH: 24
<212> TYPE: DNA
<213> ORGANISM: Artificial Sequence
<220> FEATURE:
<223> OTHER INFORMATION: synthetic construct

<400> SEQUENCE: 13
cagtcttacg agtgtgctcc agat                                        24

<210> SEQ ID NO 14
<211> LENGTH: 24
<212> TYPE: DNA
<213> ORGANISM: Artificial Sequence
<220> FEATURE:
<223> OTHER INFORMATION: synthetic construct

<400> SEQUENCE: 14
atgaggaata ctgcctctga agtg                                        24

<210> SEQ ID NO 15
<211> LENGTH: 21
<212> TYPE: DNA
<213> ORGANISM: Artificial Sequence
<220> FEATURE:
<223> OTHER INFORMATION: synthetic construct

<400> SEQUENCE: 15
tgttccaggt gcttgtcatc c                                           21

<210> SEQ ID NO 16
<211> LENGTH: 23
<212> TYPE: DNA
<213> ORGANISM: Artificial Sequence
<220> FEATURE:
<223> OTHER INFORMATION: synthetic construct

<400> SEQUENCE: 16
ccactgttag ccaagatgga gaa                                         23

<210> SEQ ID NO 17
<211> LENGTH: 20
<212> TYPE: DNA
<213> ORGANISM: Artificial Sequence
<220> FEATURE:
<223> OTHER INFORMATION: synthetic construct

<400> SEQUENCE: 17
gatgcggctc cttggaatta                                             20

<210> SEQ ID NO 18
<211> LENGTH: 22
<212> TYPE: DNA
<213> ORGANISM: Artificial Sequence
<220> FEATURE:
<223> OTHER INFORMATION: synthetic construct

<400> SEQUENCE: 18
ggaggaacat gcttgtcatg ac                                          22

<210> SEQ ID NO 19
<211> LENGTH: 21
<212> TYPE: DNA
<213> ORGANISM: Artificial Sequence
<220> FEATURE:
<223> OTHER INFORMATION: synthetic construct

<400> SEQUENCE: 19
caggagacgt gattgaaagg g                                           21

<210> SEQ ID NO 20
<211> LENGTH: 20
<212> TYPE: DNA
<213> ORGANISM: Artificial Sequence
<220> FEATURE:
<223> OTHER INFORMATION: synthetic construct

<400> SEQUENCE: 20
gcccccagag taagactggg                                             20

<210> SEQ ID NO 21
<211> LENGTH: 20
<212> TYPE: DNA
<213> ORGANISM: Artificial Sequence
<220> FEATURE:
<223> OTHER INFORMATION: synthetic construct

```
<400> SEQUENCE: 21
cagcacgtga aggtggggac                                               20

<210> SEQ ID NO 22
<211> LENGTH: 20
<212> TYPE: DNA
<213> ORGANISM: Artificial Sequence
<220> FEATURE:
<223> OTHER INFORMATION: synthetic construct

<400> SEQUENCE: 22
cagcacgtga aggtggggac                                               20

<210> SEQ ID NO 23
<211> LENGTH: 21
<212> TYPE: DNA
<213> ORGANISM: Artificial Sequence
<220> FEATURE:
<223> OTHER INFORMATION: synthetic construct

<400> SEQUENCE: 23
ttcgggagga actgtgggta t                                             21

<210> SEQ ID NO 24
<211> LENGTH: 20
<212> TYPE: DNA
<213> ORGANISM: Artificial Sequence
<220> FEATURE:
<223> OTHER INFORMATION: synthetic construct

<400> SEQUENCE: 24
ggttgctcac gcgttactca                                               20
```

BILE ACID RECEPTOR AGONISM FOR TREATING ADDICTION

CROSS-REFERENCE TO RELATED APPLICATIONS

This application claims benefit of U.S. Provisional Application No. 62/196,776, filed Jul. 24, 2015, which is hereby incorporated herein by reference in its entirety.

STATEMENT REGARDING FEDERALLY SPONSORED RESEARCH OR DEVELOPMENT

This invention was made with Government Support under Grant No. DK096527 awarded by the National Institutes of Health. The Government has certain rights in the invention.

BACKGROUND

Drug addiction represents a serious problem for many individuals, their families and society in general. While treatment for substance abuse and dependence often focuses on combating the psychological aspects of addiction, patients in treatment also often receive prescription drugs to assist in their recovery in a variety of ways. Finding new treatments to help addicts overcome their addiction and avoid future drug use would provide a significant advantage in combating drug addiction.

SUMMARY

Compositions and methods for treating addiction in a subject are disclosed. In some embodiments, the disclosed compositions and methods can be used to treat any substance use disorders supported by dysregulated dopamine neurotransmission. For example, in some cases, food "addiction" and obesity can be treated by the disclosed methods.

In particular, compositions and methods for treating addiction to a dopaminergic psychostimulant, such as cocaine, ketamine, methylenedioxypyrovalerone (MDPV), naphyrone, and Phencyclidine (PCP), amphetamine, methamphetamine, 3,4-methylenedioxymethamphetamine (MDMA), cathinone, methcathinone, mephedrone, methylone, methylphenidate (Ritalin, Metadate, Concerta), dexmethylphenidate (Focalin), dextroamphetamine (Dexedrine), mixed amphetamine salts (Adderall), dextromethamphetamine (Desoxyn), or lisdexamfetamine (Vyvanse), are disclosed.

In some embodiments, addiction is treated by agonizing bile acid receptors in the subject. For example, in some embodiments, the method comprises surgically diverting bile acids in the subject in a manner suitable to increase circulating bile acids in the subject.

In some embodiments, the method comprises administering to the subject a therapeutically effective amount of a composition comprising a bile acid receptor agonist. For example, the bile acid receptor agonist can be selected from the group consisting of cholic acid (CA), lithocholic (LCA), taurolithocholic acid (TLCA), deoxycholic acid (DCA), chenodeoxycholic acid (CDCA), ursodeoxycholic acid (UDCA), linolenic acid, oleanolic acid, betulinic acid, or any combination thereof. The bile acid receptor agonist can be selected from the group consisting of procyanidin extract, cafestol, or a combination thereof. The bile acid receptor agonist can be a synthetic bile acid receptor agonist, such as obeticholic acid.

In some embodiments, the bile acid receptor agonist is administered to the subject daily for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days, or at least 1, 2, 3, 4, 5, 6, 7, 8, 9, 10, 11, 12 weeks.

Also disclosed is a composition comprising a bile acid agonist in a therapeutically effective amount to treat addiction to a dopaminergic psychostimulant in a subject. In some cases, the composition is formulated for oral administration.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A illustrates the biliary diversion procedure, where the common bile duct was ligated proximal to the pancreatic duct. The gallbladder was then anastomosed to one of the following: (1) jejunum 4 cm distal to the ligament of Treitz (GB-J), (2) ileum 4 cm proximal to the ileo-caecal valve (GB-IL) or (3) gallbladder-duodenal anastomosis (GB-D model) at the level of the ampulla of Vater. GB-D was performed without significant alteration of bile flow and functioned as a sham surgery. The RYGB procedure was performed as we previously described (Furet, J. P. et al. Diabetes 59, 3049-3057 (2010)). Mice were fed a high fat diet (HFD) for induction of diet-induced obesity (DIO), underwent the surgical procedures and were monitored for 8 weeks post-operatively. FIGS. 1B to 1D are graphs showing average daily food intake, Bio-Sery F3282 (5.49 kcal g$^{-1}$) (FIG. 1B); relative change in body weight in N of 15 DIO, 15 GB-IL and 7 RYGB mice (FIG. 1C); and serial body composition measures via NMR of fat and lean mass (N of 15 DIO, 12 GB-D, 11 GB-J, 15 GB-IL, 12 RYGB) (FIG. 1D). Values shown are mean±s.e.m. *P<0.05, P<0.01, *P<0.001 versus DIO controls by one-way analysis of variance with Dunn's post-test.

FIG. 1A is a bar graph showing serum bile acid levels in mice subjected to biliary diversion (GB-D, GB-J and GB-IL) and RYGB relative to DIO controls at 8 weeks post-operative. *P<0.05, ** P<0.01 versus DIO by one-way analysis of variance with post-test. Values shown are mean±s.e.m. N of 5 per group. FIG. 2B is a bar graph showing fold change in serum BAs in in mice subjected to biliary diversion (GB-IL) and RYGB.

FIG. 3A is a bar graph showing blood glucose measured after a 4-h period of food-restriction. FIG. 3B is a bar graph showing area under the curve (AUC) measurements between 0 and 120 min in experimental groups that underwent intraperitoneal glucose challenge at 2, 4 and 8 weeks post-operative following biliary diversion procedures. FIGS. 3C to 3G are bar graphs showing fasting plasma insulin (FIG. 3C), the homeostatic model assessment of insulin resistance (HOMA-IR) (FIG. 3D), serum cholesterol (FIG. 3E), serum FFAs (FIG. 3F), serum triglycerides (FIG. 3G) determined at 4 weeks post-operative with GB-J, GB-IL and RYGB compared with DIO. FIGS. 3H and 3I show insulin sensitivity determined by the hyperinsulinemic-euglycemic clamp, where a continuous infusion of insulin (4 mU kg$^{-1}$ min$^{-1}$) was delivered with euglycemia (140 mg dl$^{-1}$) maintained by a variably adjusted glucose infusion. FIG. 3H is a graph showing glucose infusion rates (mg glucose per kg min$^{-1}$) over the 120 min procedure in DIO, GB-IL and RYGB mice (N=4). FIG. 3I is a bar graph showing the mean glucose infusion rates during the last 20 min of the clamp. FIG. 3J to 3M are bar graphs showing faecal fat (w/w % by mass) (FIG. 3J), faecal cholesterol (mol per g faeces) (FIG. 3K); faecal FFA (mol per g faeces) (FIG. 3L), and faecal triglyceride (mol per g faeces) (FIG. 3M) in mice under study. *P<0.05; P<0.01; *P<0.001 versus DIO by one-way analysis of variance with Dunn's post-test. Values shown are mean±s.e.m. (for a,b, n of 15 DIO, 17 GB-D, 18 GB-J, 23 GB-IL, 6 RYGB; for c,d; j-m, n of 5-10 per group).

FIG. 4A is a graph showing energy expenditure over a 24-h period was assessed by indirect calorimeter in DIO, GB-IL and DIO mice at 4 weeks post-operative. FIG. 4B is a bar graph showing unadjusted energy expenditure (kcal h$^{-1}$). FIG. 4C is a bar graph showing ANCOVA adjusted mean energy expenditure. FIG. 4D is a bar graphs showing food intake (kcal per day) monitored daily for 5 days in each study group. FIG. 4E is a gar graph showing the frequency of locomotor activity (pedestrian meters) as determined by beam breaks per 24-h period. N of 4 DIO, N of 6 GB-IL, N of 6 RYGB per group. Values shown are the mean±s.e.m. *P<0.05 by two-way ANCOVA.

FIG. 5A shows liver steatosis as assessed by H&E staining in lean, DIO, GB-D, GB-J, GB-IL and RYGB mice at 8 weeks after surgery. FIG. 5B is a bar graph showing that the liver steatosis was significantly reduced in GB-IL and RYGB mice relative to DIO. FIG. 5C shows expression of FXR target genes in liver at 4 weeks post-operative. FIGS. 5D and 5E show canonical pathways most differentially expressed between GB-IL versus DIO (FIG. 5D) and RYGB versus DIO (FIG. 5E). Expression of hepatic genes involved in agranulocyte adhesion (FIG. 5F), cholesterol biosynthesis (FIG. 5G), eicosanoid signaling (FIG. 5H), and stellate cell activation (FIG. 5I). FIGS. 5J to 5L show inflammation by hepatic F4/80 (FIG. 5J), Ki-67 (FIG. 5K) and caspase 3 (FIG. 5L) by immunohistochemical staining. *P<0.05, ***P<0.001 versus DIO by one-way analysis of variance with Dunn's post-test. Values are mean±s.e.m. (N of 5-10 per group for b-i; 4 per group for j-l). Magnification bar, 200 µm.

FIGS. 9A and 9B show HFD consumption (FIG. 9A) and relative changes in body weight (FIG. 9B) of DIO, GB-D, GB-J, GB-IL, RYGB and pair-fed to GB-IL mice up to eight weeks post-op. *P<0.05, P<0.01, *P<0.001 versus DIO controls. Values shown are means±SEM (one-way ANOVA with Dunn's post-test). N=15 DIO, 14 GB-D, 14 GB-J, 15 GB-IL, 7 RYGB, 6 PF to GB-IL.

FIGS. 14A to 14D show RNA-seq analysis (all transcripts represented, filtered to remove zero values; 25,212 transcripts) from GB-IL and DIO mouse livers (FIGS. 14A and 14B) or RYGB and DIO mouse livers (FIGS. 14C and 14D). FIGS. 14A and 14C are box plots depicting the difference among RNA-seq datasets after normalization by Robust Microarray Averaging (RMA). Boxes show the 25th and 75th percentiles in the distribution of log-transformed (log base 2) intensities. The median is the horizontal bar in the middle of the box. The whiskers (dotted lines extending from the boxes) illustrate the maximum value or 1.5 times the interquartile range of data (IQR), whichever is smaller. The circles display any points beyond these whiskers. FIGS. 14B and 14D are Volcano plots of log 2 fold-change (x-axis) versus −log 10 FDR-corrected p-value (y-axis, representing the probability that the gene is differentially expressed) in RNA-seq data of mouse livers from GB-IL vs DIO (FIG. 14B) and RYGB vs DIO mice (FIG. 14D).

FIG. 17A shows rarefaction curves (OUT at sequences dissimilarity cutoff<3%) calculated for OTUs indicating that the analysis neared plateau but could benefit from additional sequencing. FIG. 17B shows Chao1 estimates of gut microbial diversity. *P<0.05. FIG. 17C shows Principal component analysis indicating each sample microbiota variance relative to each other. N=5 per group.

FIGS. 18A to 18D show plasma concentrations of total, UDCA, and GUDCA bile acids preoperatively and following RYGB. Serial plasma samples were collected for bile acid measurements. FIG. 18A shows total bile acids concentration, which represents the sum of 17 different bile acid species, are significantly increased at one and 24 months after RYGB. FIGS. 18B to 18D show increases in total bile acid concentrations seen at one month are due to increases in ursodeoxycholic acid (FIG. 18B), glycoursodeoxycholic acid (FIG. 18C), and tauroursodeoxycholic acid (FIG. 18D). Sample size for each time point in the surgical cohort was 19-21 individuals. Lean individuals (n=8) are included for visual comparison only. Asterisks represent significant differences of indicated time points, *P<0.05, P<0.01, *P<0.001.

FIG. 19E shows hyocholic acid had a small but significant increase at 24 months compared to preoperative levels. Sample size for each time point in the surgical cohort is 20-30 individuals. Lean individuals (n=8) are included for visual comparison only. Asterisks represent significant differences of indicated time points, *P<0.05, **P<0.01.

FIGS. 21A to 21F show biliary diversion surgery impairs cocaine locomotor sensitization and CPP. FIG. 21A is a schematic representation of GB-D (control) surgery and GB-IL surgery. FIG. 21B shows weight changes following surgery in GB-D and GB-IL mice. FIG. 21C illustrates how mice underwent surgery (GB-D or GB-IL), recovered, and underwent CPP. Mice were later sacrificed or used for further behavioral testing. FIG. 21D shows average group locomotor activity in CPP chambers during four cocaine exposures (20 mg/kg, i.p.) with linear regression of activity over the four exposures (# indicates significant regression from zero slope). FIG. 21E shows percent CPP shows reduced preference for cocaine-paired side in GB-IL group. FIG. 21F shows open field locomotion. There was a reduced peak response to cocaine with no change in basal locomotion.

FIG. 22A shows a recording setup in the nucleus accumbens. The carbon fiber recording electrode was placed within the nucleus accumbens core with a two-pronged stimulating electrode. FIG. 22B shows Top, Control (GB-D) evoked DA responses are stable at 5 minute intervals. Cocaine robustly enhanced the evoked DA response. Bottom, Biliary diversion (GB-IL) evoked DA responses are stable at 5 minute intervals. The effect of cocaine is blunted, compared with control mice. FIG. 22C shows Area Under Curve of the evoked DA response normalized to the pre-cocaine control value in each slice. GB-IL slices exhibit a blunted response to cocaine compared to GD-D control slices (p<0.05, paired t-test). FIG. 22D shows the peak evoked DA response was not significantly different across groups, consistent with no change in the pre-synaptic DA vesicular release properties (p>0.05, one way ANOVA). FIGS. 22E and 22F show two kinetic measures of the rate of DA clearance from the extracellular space showed a trend of cocaine having a blunted impact in the GB-IL mice but did not reach statistical significance in this data set.

FIG. 23A shows GB-IL mice exhibit greatly elevated levels of serum bile acids, particularly conjugated bile acids. FIG. 23B illustrates how mice were treated with a fairly non-selective bile acid receptor agonist and bile acid analog (6-ECDCA/OCA) chronically for 4 weeks during which mice underwent CPP for cocaine. FIG. 23C shows cocaine CPP was significantly reduced in the group treated with 6-ECDCA, recapitulating the finding from the surgical model.

FIG. 24A shows there were no significant differences between groups in a Morris Water Maze acquisition task. FIG. 24B shows there were no significant differences between groups in a Morris Water Maze recall task. FIG. 24C shows mean swimming speed in GB-D and GB-IL mice. FIG. 24D shows there were no significant differences in latency to fall from a rotarod. FIG. 24E shows time immobile on a tails suspension task was similar between groups. FIG. 24F shows open field locomotion revealed a significant increase in center time in the GB-IL mice.

FIG. 27A is a schematic representation of GB-D (black arrow) and GB-IL (gray arrow) surgery. Dotted boxes outline incision sites in gallbladder and intestine. FIG. 27B shows body weight following GB-D or GB-IL surgery (n=17-21; *p<0.001 by multiple t test comparison). FIG. 27C shows amperometric recordings of DA from the NAc in GB-D (top) and GB-IL (bottom) mice. Electrically-evoked DA responses are stable at 5 minute intervals. Cocaine robustly enhanced the evoked DA response in the GB-D mice (n=4). This effect is blunted in GB-IL with respect to GB-D mice (n=5). FIG. 27D shows quantitation of the peak amplitude of amperometric recordings under baseline (dotted bar) or cocaine (checkered bar) conditions in GB-D (black) or GB-IL (gray) animals (p>0.05 comparing baseline to cocaine for each surgical group). FIG. 27E shows AUC of the evoked DA response normalized to the average of the pre-cocaine baseline values from each slice (n=4-5; *p<0.05, Student's t test). FIG. 27F shows levels of DA, NE, and 5-HT in NAc tissue punches from GB-D and GB-IL mice. No significant differences were noted (n=4-6; p>0.05 by Student's t test).

FIGS. 28A to 28D show bile diversion to the ileum blocks cocaine locomotor sensitization and reduces cocaine CPP. FIG. 28A illustrates how mice underwent surgery (GB-D or GB-IL), recovered for 2 weeks, and began the cocaine CPP paradigm. FIG. 28B shows average group locomotor activity in CPP chambers during four cocaine exposures (20 mg/kg, i.p.) with linear regression of activity over the four exposures (n=12-15; *p<0.05 indicates significant regression from zero slope; F(1,46)=6.280). FIG. 28C shows cocaine CPP expressed as % CPP normalized to GB-D average (n=13-14; *p<0.05 by Student's t test). FIG. 28D shows open field locomotion. GB-IL mice exhibit a reduced response to cocaine with no difference in basal locomotion (n=8-10; p<0.05 by two way RM ANOVA for cocaine administration, F(1, 16)=6.544; *p<0.001 between 10 and 30 min following cocaine injection by multiple t test comparison). (inset) Area under the curve for cocaine locomotor responses in GB-D and GB-IL mice (p<0.01 by Student's t test).

FIG. 29A shows GB-IL mice exhibit elevated levels of serum total and conjugated bile acids with respect to GB-D (n=7-8; *p<0.05 by Student's t test). FIG. 29B shows 10 μM OCA reduced EPSC amplitude in NAc medium spiny neurons (n=4; *p<0.05 by Student's t test). FIG. 29C illustrates how mice were treated orally with either vehicle or 10 mg/kg OCA six days a week for four weeks. After 2 weeks the mice were started on the cocaine CPP paradigm. FIG. 29D shows OCA-treated mice showed reduced preference for the cocaine-paired chamber (n=7-8; *p<0.05 by Student's t test) expressed as % CPP normalized to GB-D average. FIG. 29E shows constitutive deletion of the TGR5 receptor (−/−) results in increased preference for the cocaine-paired chamber, expressed as % CPP normalized to TGR5 (+/+) littermate average (n=11-14; *p<0.05 by Student's t test).

FIG. 31A shows there were no significant differences between GB-D and GB-IL mice in a Morris Water Maze acquisition task (n=7-8; p>0.05 by two-way RM ANOVA). FIG. 31B shows there were no significant differences between groups in a Morris Water Maze recall task (p>0.05 by Student's t test). FIG. 31C shows mean swimming speed in GB-D and GB-IL mice (p>0.05 by Student's t test). FIG. 31D shows there were no significant differences in latency to fall from a rotarod (n=5-8; p>0.05 by two-way RM ANOVA). FIG. 31E shows time immobile on a tail suspension task was similar between groups (n=7-8; p>0.05 by Student's t test). FIG. 31F shows open field locomotion revealed a significant increase in center time in the GB-IL mice (n=11-14; *p<0.05 by Student's t test).

DETAILED DESCRIPTION

Definitions

Figure 1A:
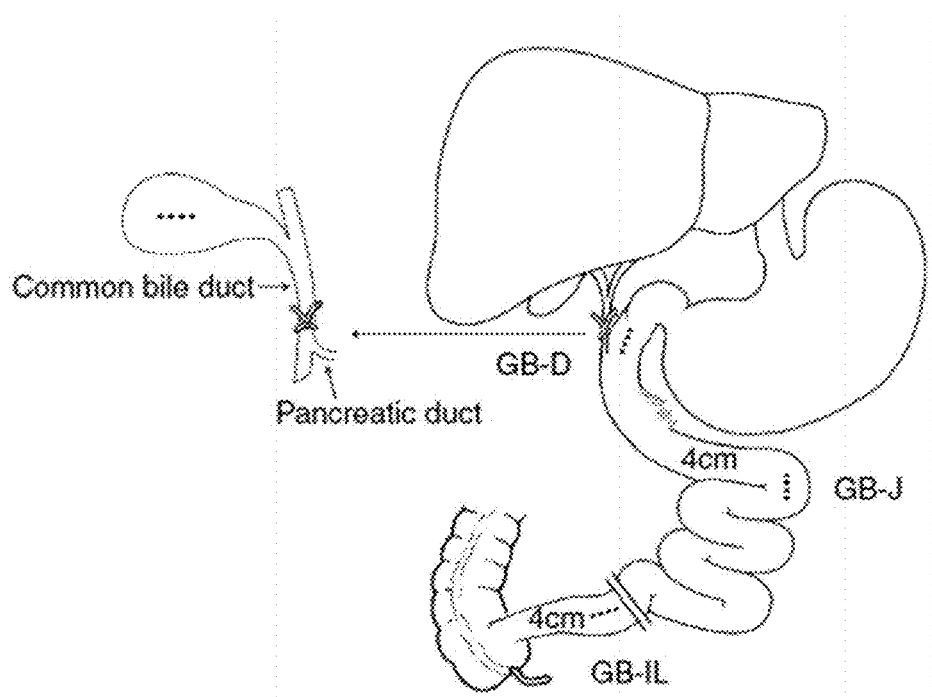
FIGS. 1A to 1D show biliary diversion schematic and effects on body weight, food intake and body composition.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "addiction" refers to a shift a neurological change from a controlled behavior to a compulsive behavior with loss of control despite adverse consequences. Drugs of abuse can alter dopamine neurotransmission in the nucleus accumbens and dorsal striatum. In a person who becomes addicted, the brain displays impaired dopamine receptor signaling. As a result of these adaptations, dopamine has less impact on the brain's reward center. It is thought that at this point, compulsion takes over. The pleasure associated with an addictive drug or behavior subsides—and yet the memory of the desired effect and the need to recreate it persists. The likelihood that the use of a drug or participation in a rewarding activity will lead to addiction is proportional to the speed with which it promotes dopamine release, the amount of that release, and the reliability of that release.

The term "dopaminergic psychostimulant" refers to psychoactive drugs that increase dopamine-related activity in the brain and thereby induce temporary improvements in either mental or physical functions or both. These stimulants can include dopamine precursors, dopamine receptor agonists, dopamine receptor antagonists, dopamine reuptake inhibitors, dopamine releasing agents, dopamine activity enhancers, and monoamine oxidase inhibitors. For example, the dopaminergic psychostimulant can be selected from the group consisting of cocaine, ketamine, methylenedioxypyrovalerone (MDPV), naphyrone, and Phencyclidine (PCP), amphetamine, methamphetamine, 3,4-methylenedioxymethamphetamine (MDMA), cathinone, methcathinone, mephedrone, methylone, methylphenidate (Ritalin, Metadate, Concerta), dexmethylphenidate (Focalin), dextroamphetamine (Dexedrine), mixed amphetamine salts (Adderall), dextromethamphetamine (Desoxyn), and lisdexamfetamine (Vyvanse).

The term "bile acid" refers to steroid acids found predominantly in the bile of mammals and other vertebrates.

The term "bile acid receptor" refers to farnesoid X receptor (FXR) nuclear receptor, G protein-coupled bile acid receptor 1 (TGR5), or a combination thereof.

The term "bile acid receptor agonist" refers to an agent that binds and activates a bile acid receptor. In some embodiments the bile acid receptor agonist is an agonist of TGR5 and/or FXR.

In some embodiments, the bile acid receptor agonist is a natural bile acid. For example, the bile acid receptor agonist can be selected from the group consisting of cholic acid (CA), lithocholic (LCA), taurolithocholic acid (TLCA), deoxycholic acid (DCA), chenodeoxycholic acid (CDCA), ursodeoxycholic acid (UDCA), linolenic acid, oleanolic acid, betulinic acid, or any combination thereof. In some cases, the bile acid receptor agonist is a procyanidin extract, a cafestol, or a combination thereof.

In some embodiments, the bile acid receptor agonist is a synthetic agonist. For example, the bile acid receptor agonist can be 6-ECDCA (INT-747, Obeticholic acid (OCA)) ((4R)-4-[(3R,5S,6R,7R,8S,9S,10S,13R,14S,17S)-6-Ethyl-3,7-dihydroxy-10,13-dimethyl-2,3,4,5,6,7,8,9,11,12,14,15,16,17-tetradecahydro-1H-cyclopenta[a]phenanthren-17-yl] pentanoic acid). Other synthetic bile acid receptor agonist include 23(S)-methylcholic acid, 23(S)-methyl-CDCA, 6α-ethyl-23(S)-methyl-3α,7α-dihydroxy-5β-cholan-24-oic acid, 6-methyl-2-oxo-4-thiophen-2-yl-1,2,3,4-tetrahydropyrimidine-5-carboxylic acid-benzyl ester, 5β-cholanic acid, 5β-cholanic acid-7α,12α-diol, 6 α-ethyl-3 α,7 α,23-trihydroxy-24-no-5β-cholan-23-sulfate sodium salt (INT-767), 6-methyl-2-oxo, imidazole[1,2-a][1,2]diazepin, fexaramine3-[2-[2-Chloro-4-[[3-(2,6-dichlorophenyl)-5-(1-methylethyl)-4-isoxazolyl]methoxy]phenyl]ethenyl]benzoic acid (GW4064), 17β-(4-hydroxybenzoyl)androsta-3,5-diene-3-carboxylic acid (MFA-1), and 3-(3,4-Difluorobenzoyl)-1,2,3,6-tetrahydro-1,1-dimethylazepino[4,5-b]indole-5-carboxylic acid 1-methylethyl ester (XL335, FXR450, WAY-362450).

In some embodiments, the synthetic bile acid receptor agonist is BR27, AGN43, MeCA, MeDCA, NIHS700, GSK8062, GSK2324, Compound 13 from Phenex, Compound 22 from Phenex, Px-102, 14 cc, Compound 32 from Kalypsys, Compound 6 from GSK, Compound 7 from GSK, and XL475.

In some embodiments, the synthetic bile acid receptor agonist is a quinazolinone disclosed in US 20120064025, which is hereby incorporated by reference in its entirety for the teaching of FXR agonists.

The compositions disclosed can be used therapeutically in combination with a pharmaceutically acceptable carrier. Pharmaceutical carriers suitable for administration of the compounds provided herein include any such carriers known to those skilled in the art to be suitable for the particular mode of administration. Suitable carriers and their formulations are described in Remington: The Science and Practice of Pharmacy, 22nd ed. 2005, ed. Allen, Loyd V., Jr. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical compositions may include carriers, thickeners, diluents, buffers, preservatives, surface active agents and the like in addition to the molecule of choice. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

In addition, the compounds may be formulated as the sole pharmaceutically active ingredient in the composition or may be combined with other active ingredients. For example, the compounds may be formulated or combined with known NSAIDs, anti-inflammatory compounds, steroids, and/or antibiotics.

The disclosed compositions, including pharmaceutical composition, may be administered in a number of ways. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant.

The compositions disclosed herein may be administered prophylactically to patients or subjects who are at risk for addiction. Thus, the method can further comprise identifying a subject at risk for addiction prior to administration of the herein disclosed compositions.

The exact amount of the compositions required will vary from subject to subject, depending on the species, age, weight and general condition of the subject, the severity of the disorder being treated, the particular drug used, its mode of administration and the like. Effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Bile Diversion to the Distal Small Intestine has Comparable Metabolic Benefits to Bariatric Surgery Results Biliary Diversion to the Illeum and RYGB Reduce Body Weight.

To determine the effects of bile diversion on weight loss and reversal of metabolic dysregulation, three mouse models were developed in which the GB was anastomosed to the duodenum (GB-D), jejunum (GB-J) or ileum (GB-IL) (FIG. 1A). The GB-D served as the sham control, as these mice have a surgical anastomosis without physiologic bile diversion. Three additional groups were studied; an RYGB group (Yin, D. P. et al. Ann. Surg. 254, 73-82 (2011)), a DIO control and control mice pair-fed to the GB-IL cohort.

Figure 1B:
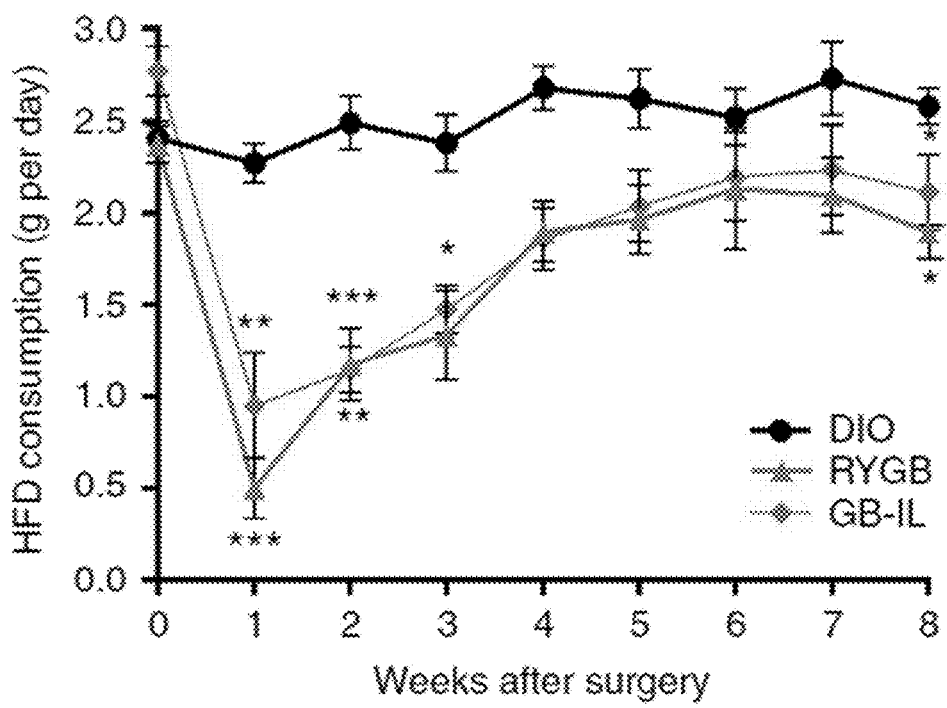
Figure 1C:
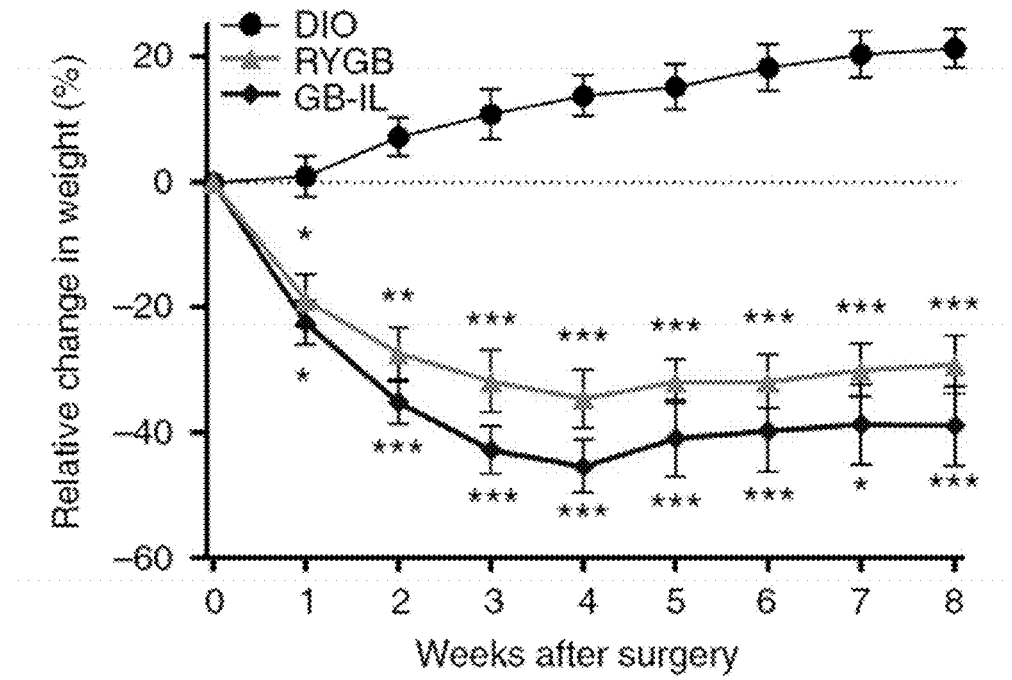
Figure 1D:
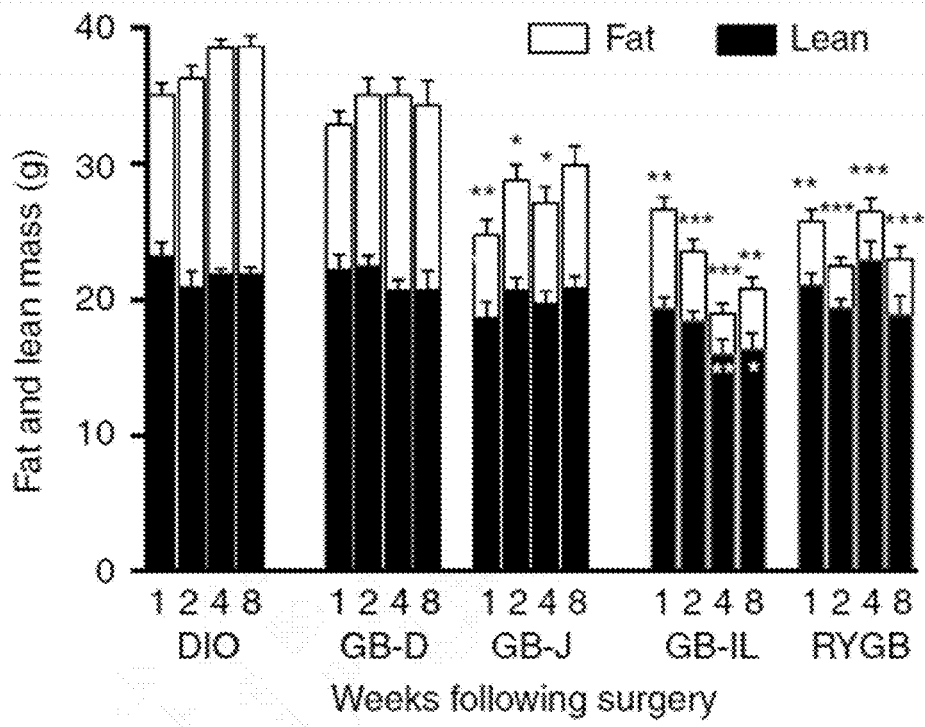

The relative efficacy of biliary diversion or RYGB on food intake (FIG. 1B), body weight (FIG. 1C) and body composition (FIG. 1D) was assessed in a mouse model of HFD-induced obesity (DIO). At 1 week post-operative, all mice that underwent surgical procedures including GB-IL and RYGB mice had decreased food consumption (FIG. 1B), consistent with the post-operative period. At 2 weeks the GB-D and GB-J mice increased their food consumption indicating surgical recovery; however, food intake in GB-IL and RYGB mice remained significantly less (FIG. 9A). Beyond 2 weeks, mice subjected to the GB-D and GB-J procedures displayed increasing body weight reaching DIO levels by 8 weeks; however, GB-IL and RYGB mice had sustained decreases in food intake (FIG. 1B and FIG. 9A). Surprisingly, mice receiving GB-IL procedures exhibited weight loss equal to or greater than that observed with RYGB throughout the remainder of the study. Consistent with the changes in body weight, mice in the GB-IL and RYGB groups had significant reductions in total body fat mass (FIG. 1D). Pair-feeding to the GB-IL cohort did not lead to weight loss similar to the GB-IL group (FIG. 9B), collectively suggesting that GB-IL and RYGB induce weight loss through mechanisms beyond reductions in food intake alone.

Biliary Diversion to the Ileum Increases Serum Bile Acids.

Figure 2A:
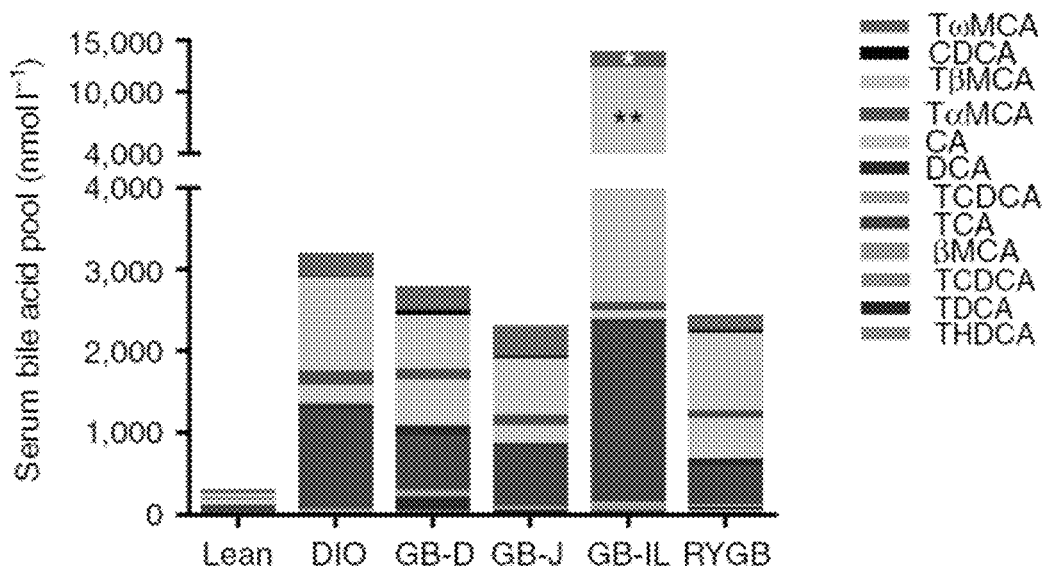
FIGS. 2A and 2B show biliary diversion modifies bile acid abundance and composition.
Figure 2B:
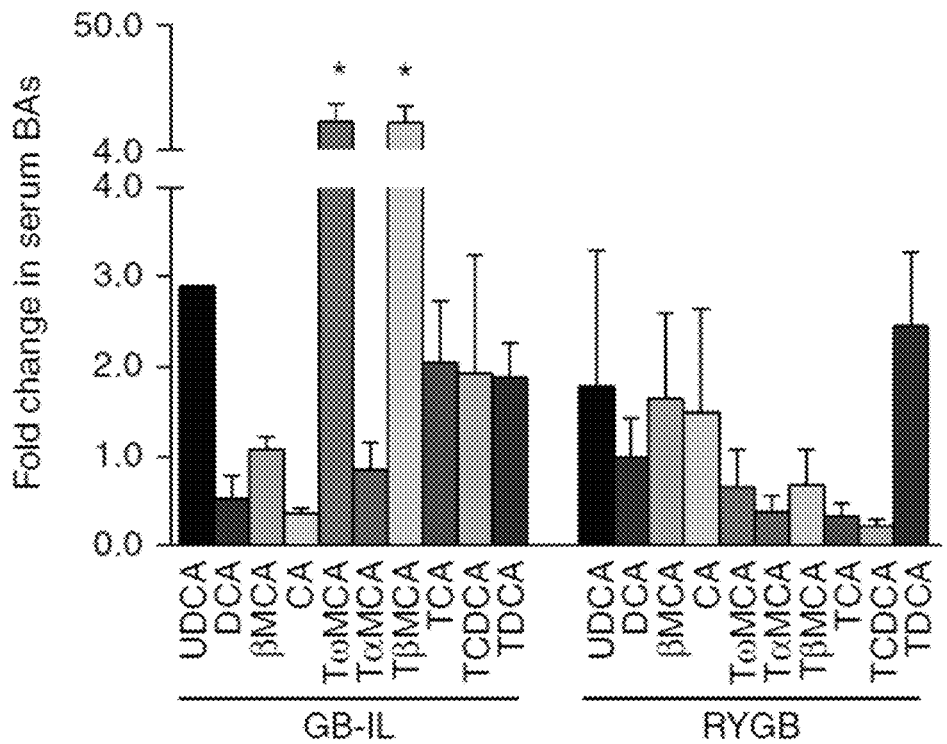
Figure 10:
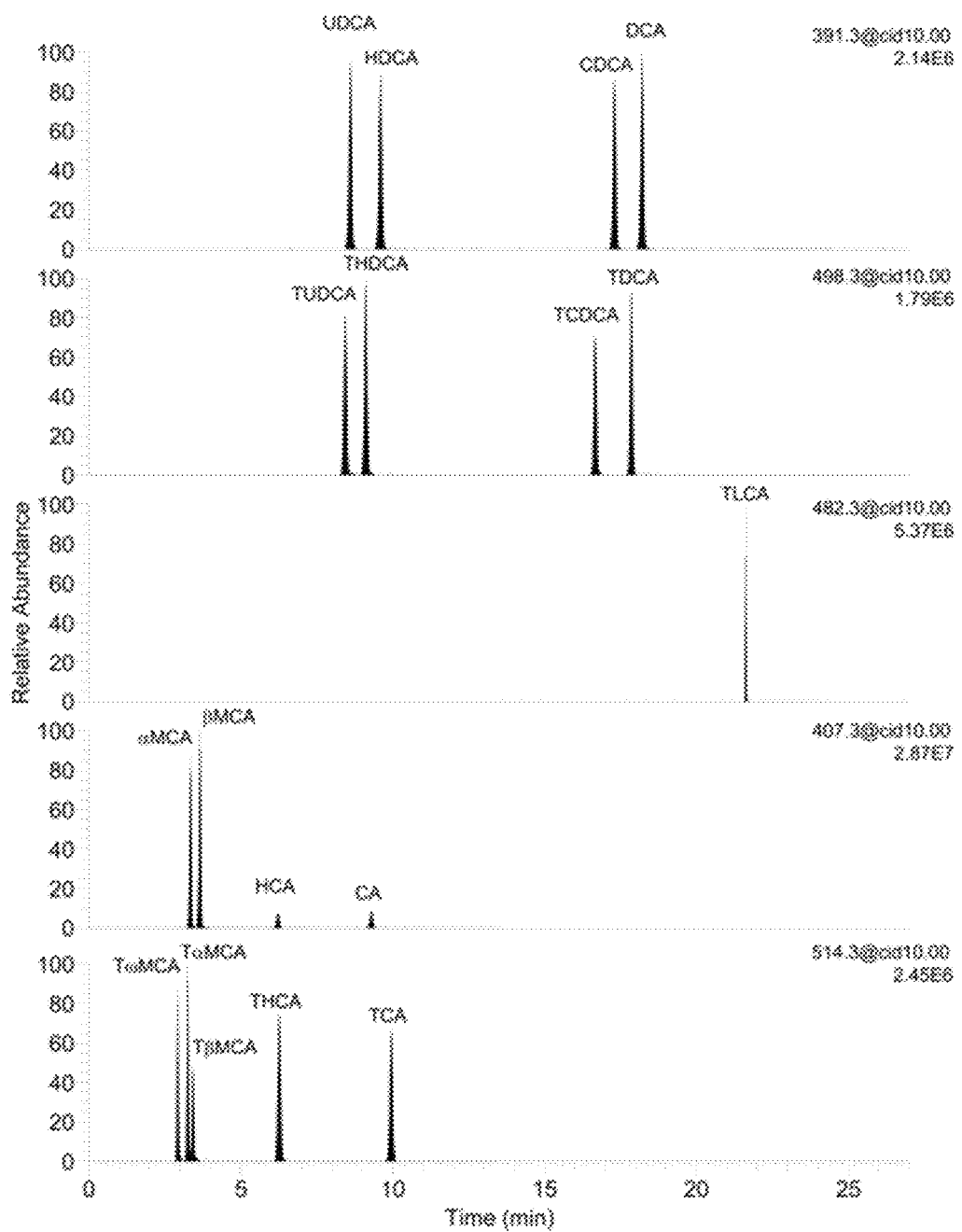
FIG. 10 shows extracted ion chromatograms of serum bile acids resolved by high-performance liquid chromatographic ESI-MS/MS. Individual samples spikes with deuterated bile acid standards were resolved over a 28 min gradient. Eluting bile acid species were subjected to mass analysis and area under the curve (AUC) determinations were made.
Figure 11:
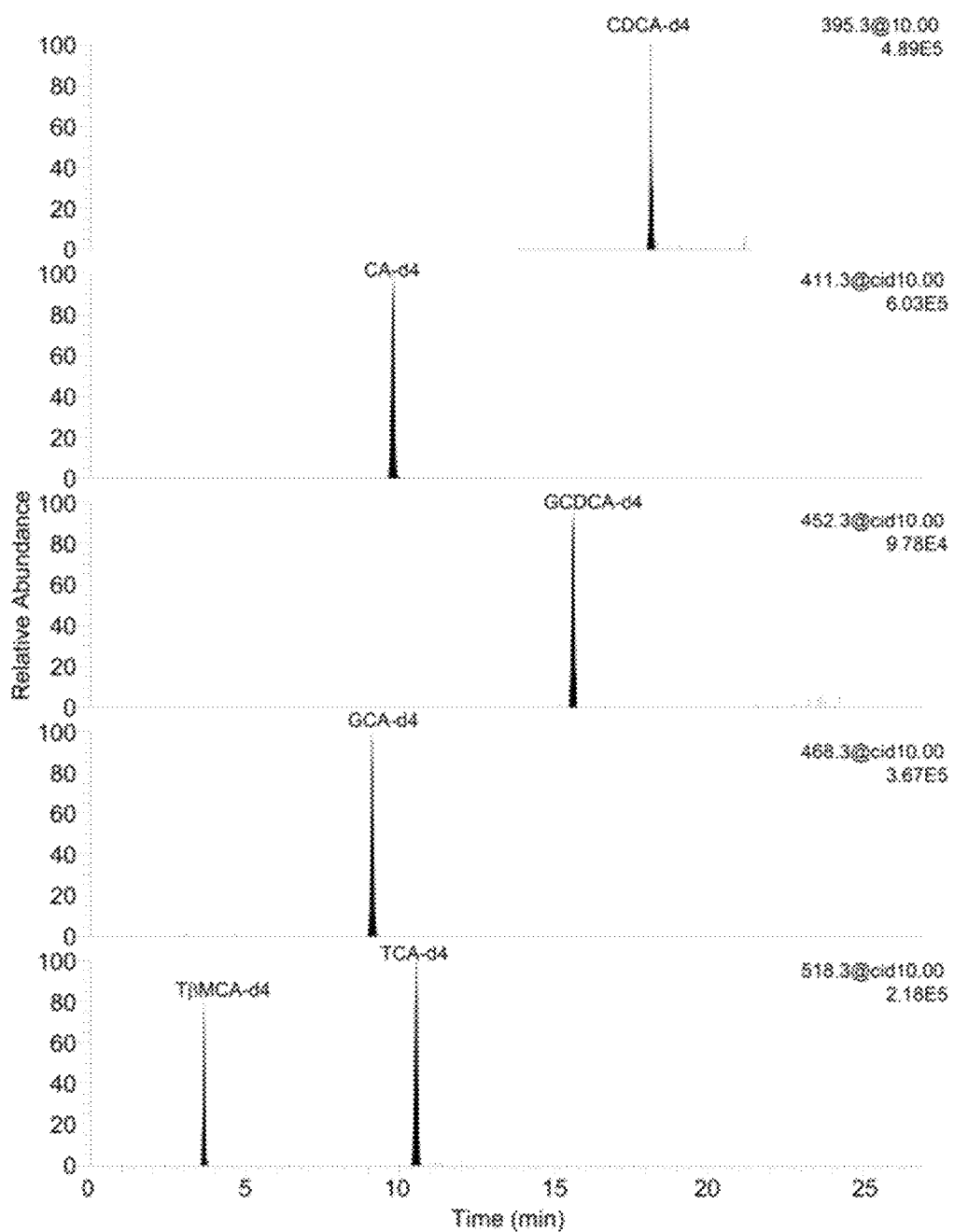
FIG. 11 show sextracted ion chromatograms of deuterated bile acids standards used as internal standards in the quantitation analysis. Individual samples spiked with deuterated bile acid standards were resolved over a 28 min gradient and used to quantify bile acid species.

To examine the potential effects of bile acid diversion on circulating bile acid levels, we measured total and fractionated bile acid concentrations in DIO controls and bile diverted mice 8 weeks post-operative. Serum bile acid levels were not significantly different among GB-D, GB-J or RYGB cohorts compared with DIO mice (FIG. 2A, FIGS. 10-11 and Tables 1-2). However, GB-IL mice showed nearly 10-fold increase in total bile acid levels that were driven primarily by increased tauro-o-MCA (ToMCA) and tauro-b-MCA (TbMCA). CA content did not significantly differ among the groups. Relative to DIO controls, serum concentrations of most other taurine-conjugated bile acids tended to be higher in GB-IL but the increases were not significant (FIG. 2B). No significant increases in any individual bile acid or total bile acid species were detected after RYGB. Thus, biliary diversion to the ileum specifically increased the conjugated bile acid species, TωMCA and TβMCA—the latter being a potent FXR antagonist (Sayin, S. I. et al. Cell Metab. 17, 225-235 (2013); Li, F. et al. Nat. Commun. 4, 2384 (2013)).

TABLE 1

Analytical settings for detected bile acids.

| Species | m/z | R.T. | Internal Standard |
|---|---|---|---|
| TωMCA | 514.3 | 2.72 | TβMCA-d4 |
| ωMCA | 407.3 | 2.80 | CA-d4 |
| TαMCA | 514.3 | 3.01 | TβMCA-d4 |
| αMCA | 407.3 | 3.17 | CA-d4 |
| TβMCA | 514.3 | 3.17 | TβMCA-d4 |
| βMCA | 407.3 | 3.49 | CA-d4 |
| THCA | 514.3 | 5.80 | GCA-d4 |
| HCA | 407.3 | 6.22 | CA-d4 |
| TUDCA | 498.3 | 8.06 | GCDCA-d4 |
| UDCA | 391.3 | 8.37 | CDCA-d4 |
| THDCA | 498.3 | 8.70 | GCDCA-d4 |
| CA | 407.3 | 9.00 | CA-d4 |
| HDCA | 391.3 | 9.36 | CDCA-d4 |
| TCA | 514.3 | 9.50 | TCA-d4 |
| TCDCA | 498.3 | 16.19 | TCA-d4 |
| CDCA | 391.3 | 17.00 | CDCA-d4 |
| TDCA | 498.3 | 17.48 | TCA-d4 |
| DCA | 391.3 | 17.94 | CDCA-d4 |
| TLCA | 482.3 | 21.59 | CDCA-d4 |
| GCDCA-d4* | 452.3 | 14.50 | |
| CDCA-d4* | 395.3 | 17.00 | |
| TCA-d4* | 518.3 | 9.50 | |
| CA-d4* | 411.3 | 9.00 | |
| TβMCA-d4* | 518.3 | 3.17 | |
| GCA-d4* | 468.3 | 8.14 | |

*deuterated internal standards

TABLE 2

Mean ± SEM bile acid species levels in bile diverted and RYGB mouse serum.

| BA Species | Obese | GB-D | GB-J | GB-IL | RYGB |
|---|---|---|---|---|---|
| TωMCA | 291.1 ± 80.2 | 291.8 ± 157 | 376.9 ± 81.2 | 1609.6 ± 437.4 | 185.9 ± 74.8 |
| TβMCA | 1145.3 ± 273.6 | 662 ± 234.1 | 692.3 ± 257.9 | 9741.9 ± 2040.2 | 947.3 ± 515.9 |
| TαMCA | 179.7 ± 50.6 | 131.3 ± 77.6 | 128.3 ± 50.9 | 110.9 ± 34 | 89.3 ± 42.1 |
| CA | 191.6 ± 51.2 | 544 ± 356.9 | 199.4 ± 80.5 | 76.4 ± 13.5 | 485.5 ± 427.1 |
| TCDCA | 46.1 ± 11.3 | 18.7 ± 39.2 | 25.1 ± 9.4 | 29.9 ± 13 | 17 ± 2.3 |
| DCA | 51.6 ± 8.6 | 120.8 ± 77.2 | 24.4 ± 8.6 | 28.4 ± 14.3 | 76.5 ± 46.4 |
| TCA | 1216.9 ± 369.6 | 665.6 ± 163.6 | 740.5 ± 166.6 | 2202.1 ± 846.6 | 476.2 ± 245.4 |
| βMCA | 15.2 ± 0.6 | 30.8 ± 7.9 | 0 ± 0 | 42.5 ± 5.6 | 38.5 ± 14.9 |
| TUDCA | 42.5 ± 12.3 | 51 ± 20.2 | 41.1 ± 10.8 | 64.5 ± 11.6 | 0 ± 0 |
| TDCA | 11.1 ± 3.2 | 167.2 ± 77.3 | 40.2 ± 14.1 | 21.3 ± 5.4 | 31.7 ± 10.3 |
| THDCA | 10.8 ± 3.8 | 55.4 ± 11.7 | 24.7 ± 7.5 | 32.9 ± 13.4 | 62.1 ± 24.8 |
| CDCA | 5.8 ± 0 | 64 ± 45.3 | 22.4 ± 15.8 | 0 ± 0 | 38.2 ± 27 | n = 5 mice per group

Biliary Diversion to the Ileum Improves Metabolism.

Figure 12A:
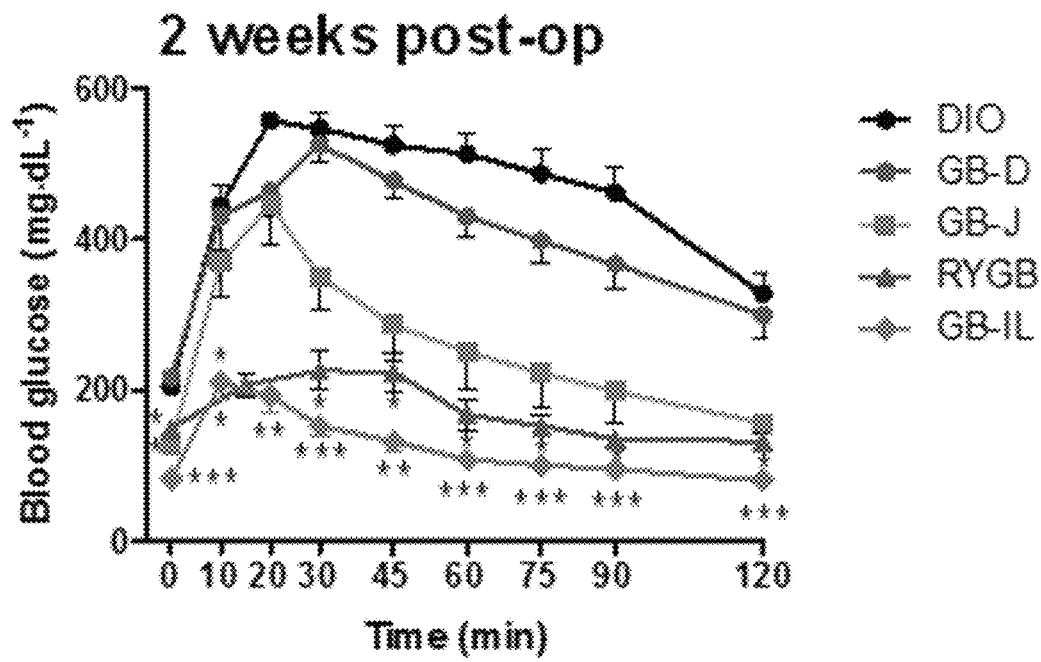
FIGS. 12A to 12C show glucose excursion curves in DIO WT, bile diversion and RYGB mice after Intraperitoneal glucose tolerance tests (IPGTT) at 2 weeks post-op (FIG. 12A), 4 weeks post-op (FIG. 12B), and 8 weeks post-op (FIG. 12C). Data are shown as mean±SEM. *P<0.05, P<0.01, *P<0.001 versus DIO by one-way ANOVA with post-test.
Figure 12B:
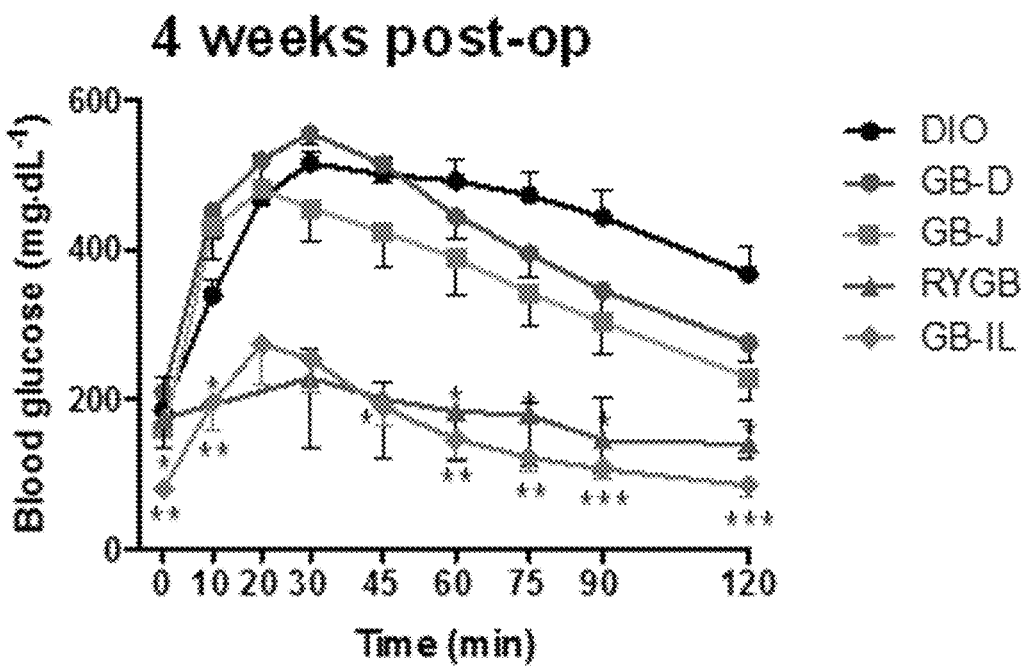
Figure 12C:
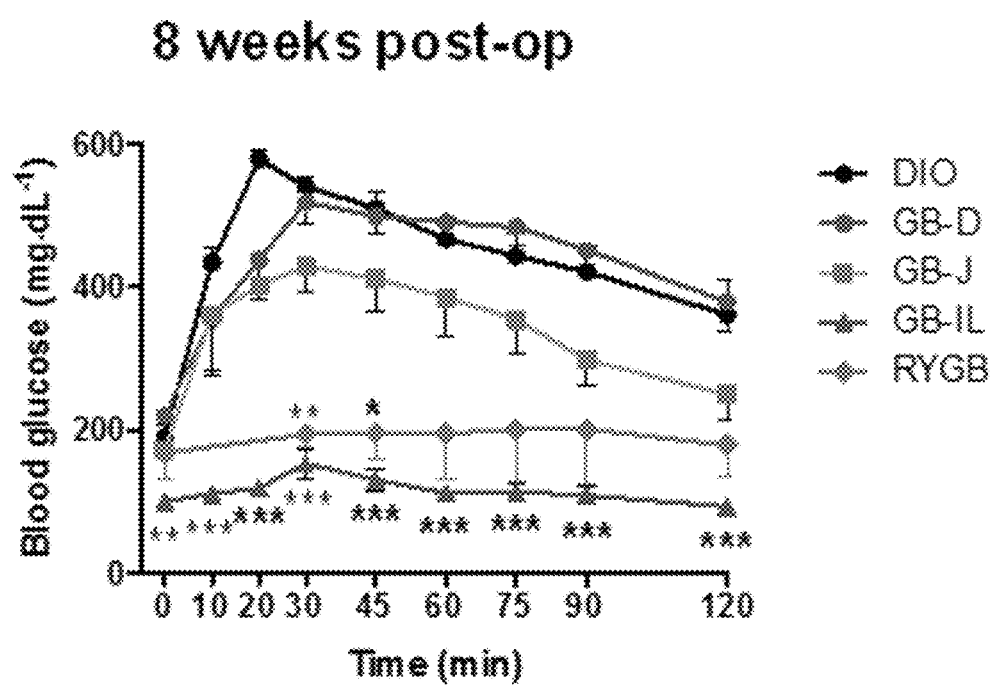

To explore the role of biliary diversion on glucose homeostasis, glucose tolerance tests were performed in all groups (FIG. 3). Fasting blood glucose levels measured at 4 weeks post-operatively were significantly lower in GB-IL and RYGB mice as compared with GB-D and GB-J mice (FIG. 3A). Blood glucose excursions following intraperitoneal glucose challenge at 2, 4 and 8 weeks post-operatively were all significantly lower with GB-IL and RYGB mice as compared with GB-D, GB-J or DIO controls, indicative of improved glucose tolerance. While the GB-J procedure elicited improved glucose tolerance at 2 weeks, the improvements were not sustained by 4 weeks post-operatively (FIGS. 3B, 12). Fasting plasma insulin (FIG. 3C) was decreased in the GB-IL group, approaching levels observed in RYGB mice. The changes in glucose and insulin levels corresponded to significantly decreased HOMA-IR, suggesting improved insulin sensitivity (FIG. 3D). Other circulating fasting metabolites also showed differences relative to DIO, with serum cholesterol being decreased in GB-IL but not RYGB, and serum free fatty acids (FFAs) significantly decreased in both GB-IL and RYGB (FIG. 3E,F). Fasting triglycerides did not differ among groups (FIG. 3G). To better define the potential changes in insulin sensitivity, separate cohorts of DIO, RYGB and GB-IL mice were subjected to hyperinsulinemic-euglycemic clamps. Consistent with improvements in whole-body insulin sensitivity, glucose infusion rates over time (FIG. 3H) and averaged during the steady state phase of the clamp (FIG. 3I) were significantly increased in RYGB and GB-IL mice compared with DIO. Thus, the effects of RYGB and GB-IL on whole-body glucose metabolism are a reflection of improvements in insulin action.

Figure 3A:
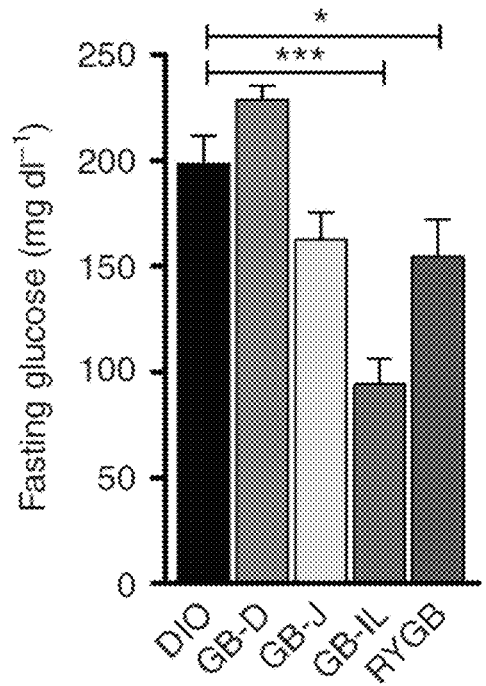
FIGS. 3A-3M show the effects of biliary diversion on glucose tolerance, insulin sensitivity and lipid metabolism.
Figure 3B:
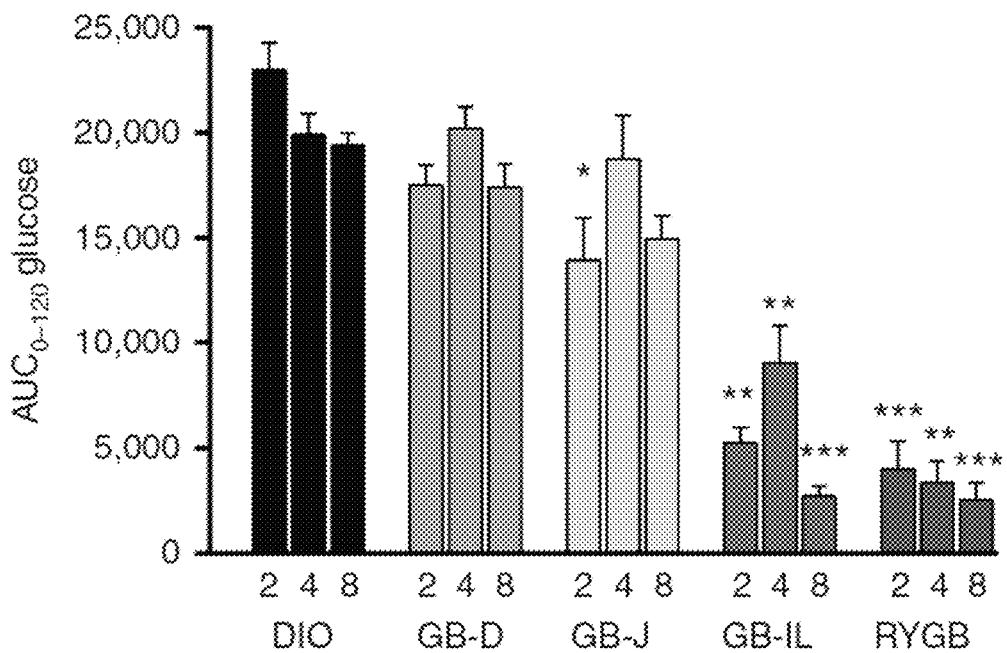
Figure 3C:
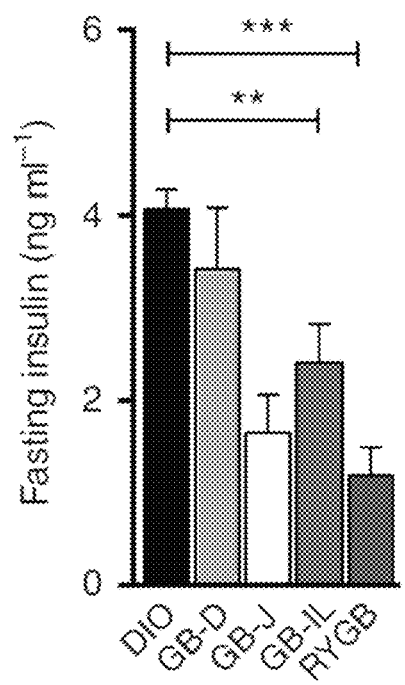
Figure 3D:
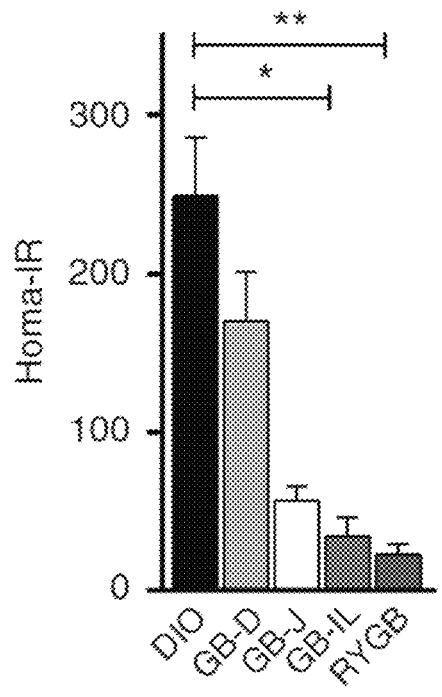
Figure 3E:
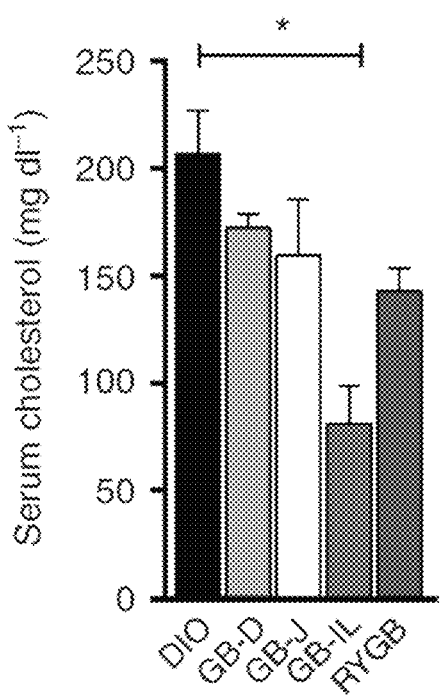
Figure 3F:
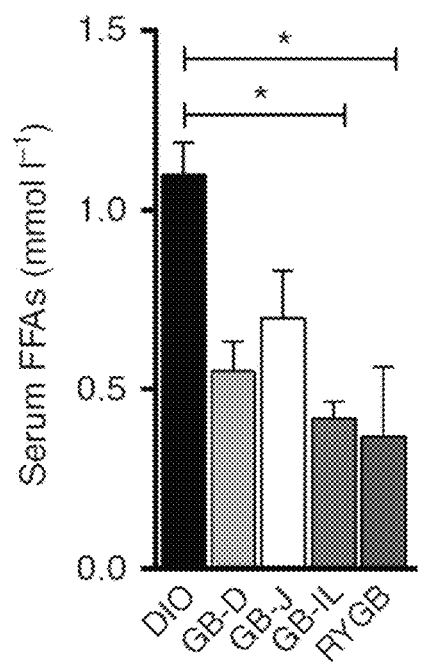
Figure 3G:
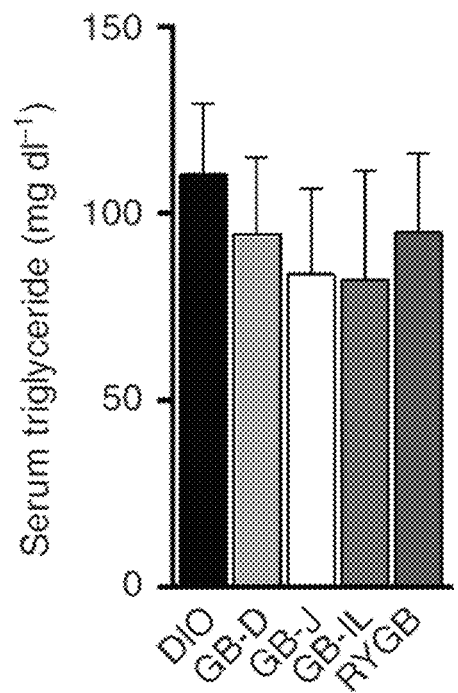
Figure 3I:
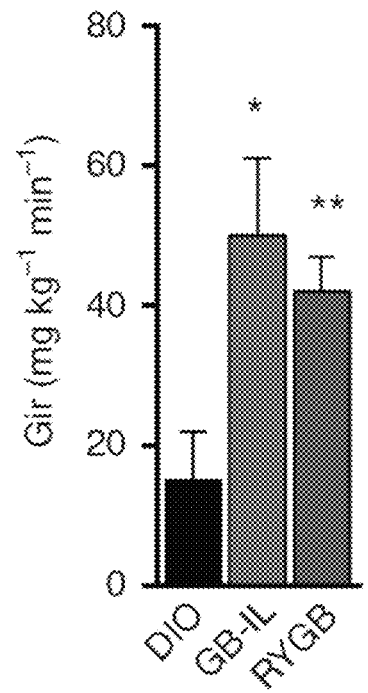
Figure 3H:
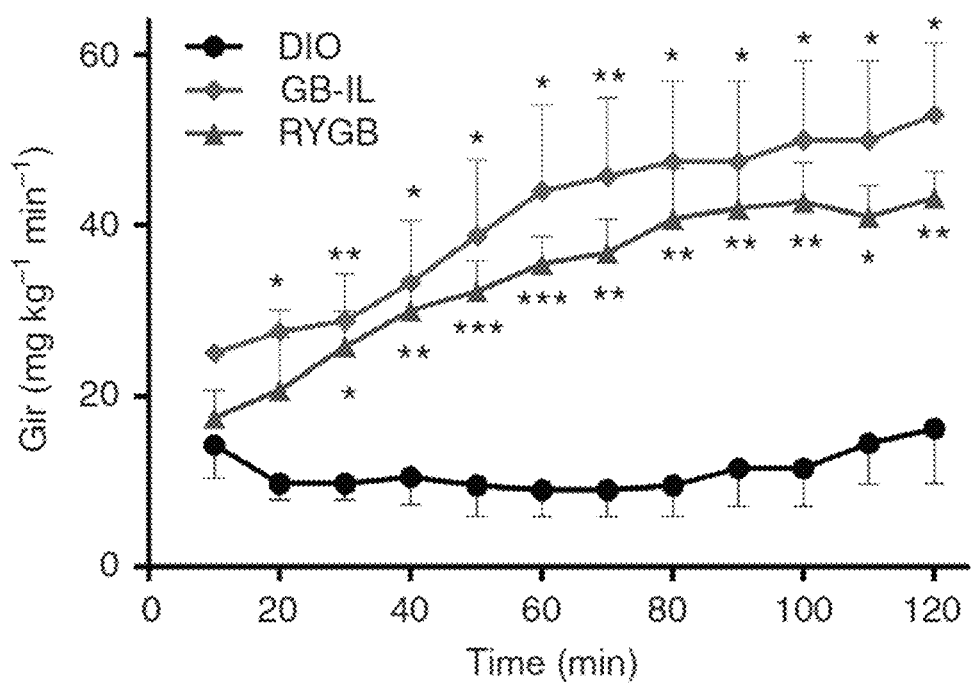
Figure 3J:
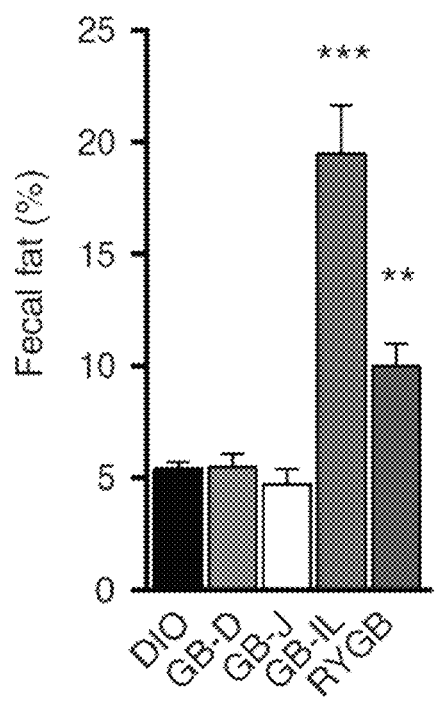
Figure 3K:
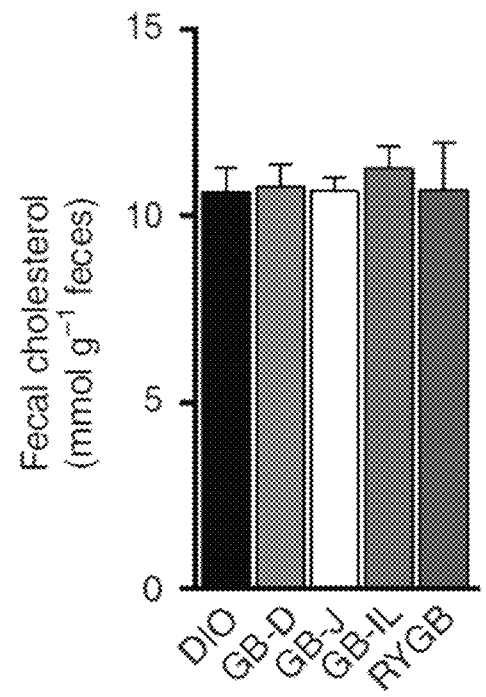
Figure 3L:
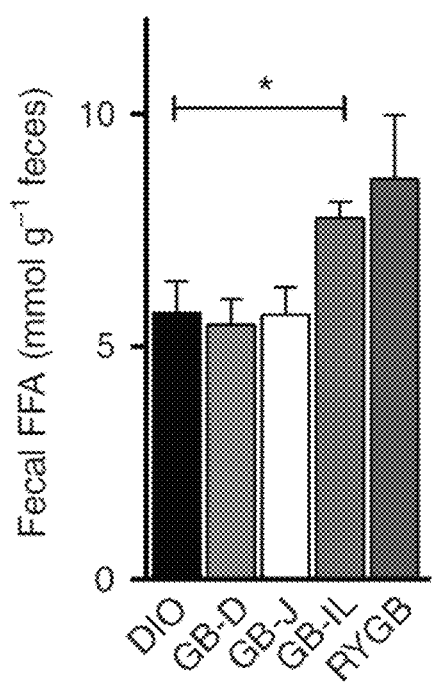
Figure 3M:
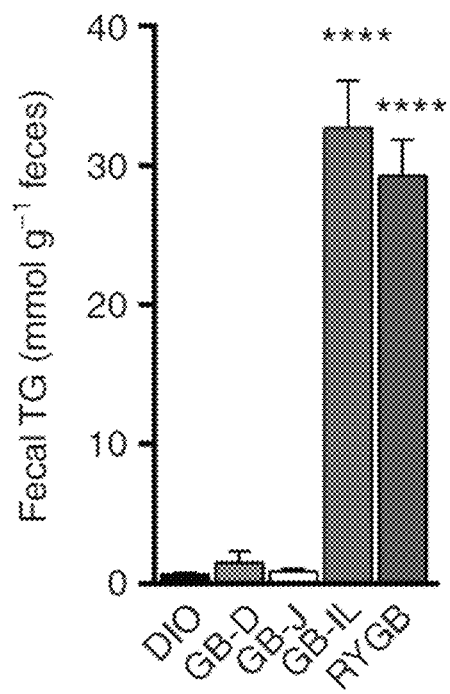

The observed decreased circulating FFAs may be reflective of either improved insulin sensitivity or incomplete absorption of fats from the gut. To assess for changes in dietary fat absorption, faeces were collected from these mice and extracted total lipid content, as well as measured faecal cholesterol, FFAs and triglycerides (FIG. 3J-M). GB-IL and RYGB had significant increases in total faecal lipids compared with DIO (FIG. 3J), which corresponded to significant increases in faecal FFAs (FIG. 3L) and triglycerides (FIG. 3M) without a change in faecal cholesterol (FIG. 3K). Overall, the data confirm that there is significant fat malabsorption in both the RYGB and GB-IL models.

Biliary Diversion to the Ileum Increases Energy Expenditure.

Figure 4A:
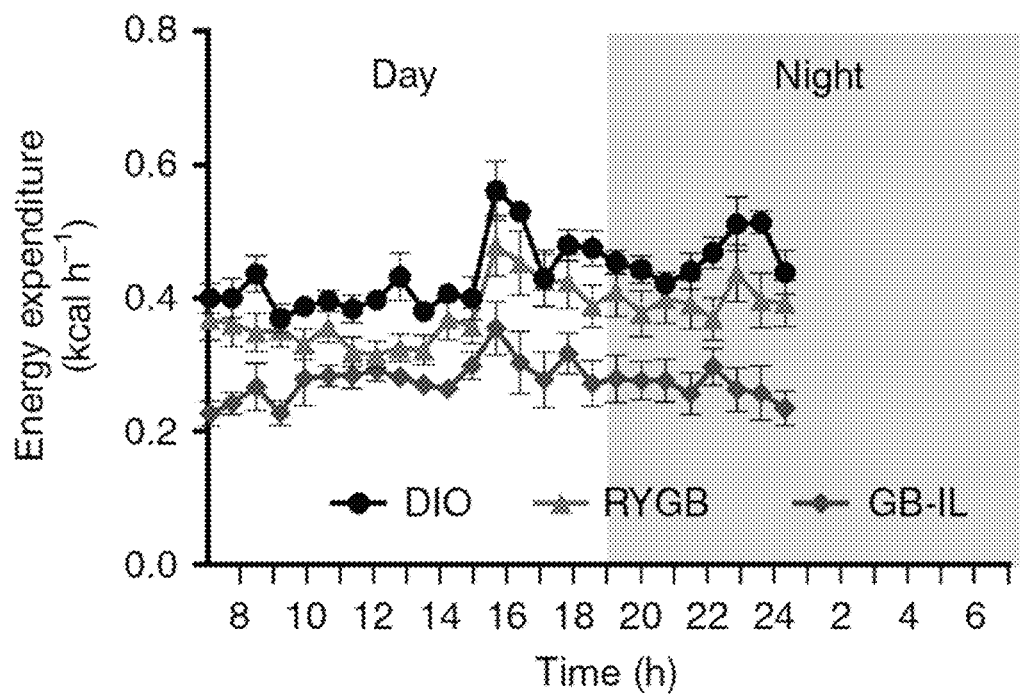
FIGS. 4A to 4E show energy expenditure in response to bariatric procedures.
Figure 4B:
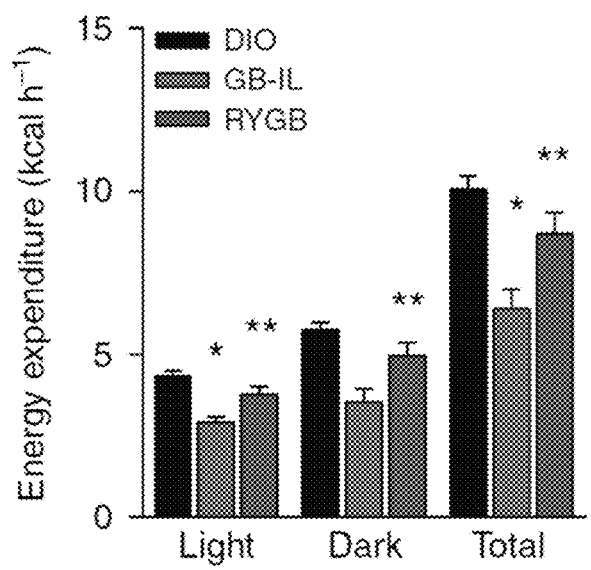
Figure 4C:
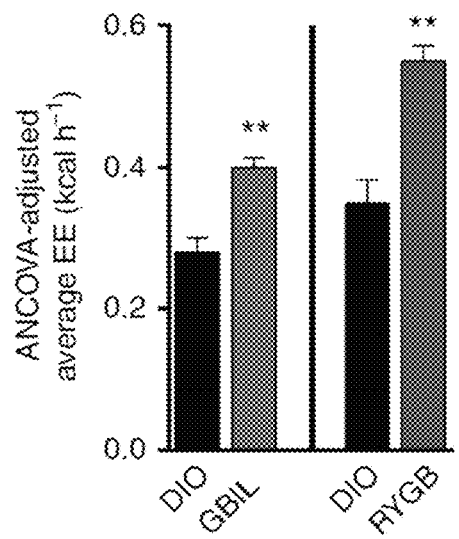
Figure 13B:
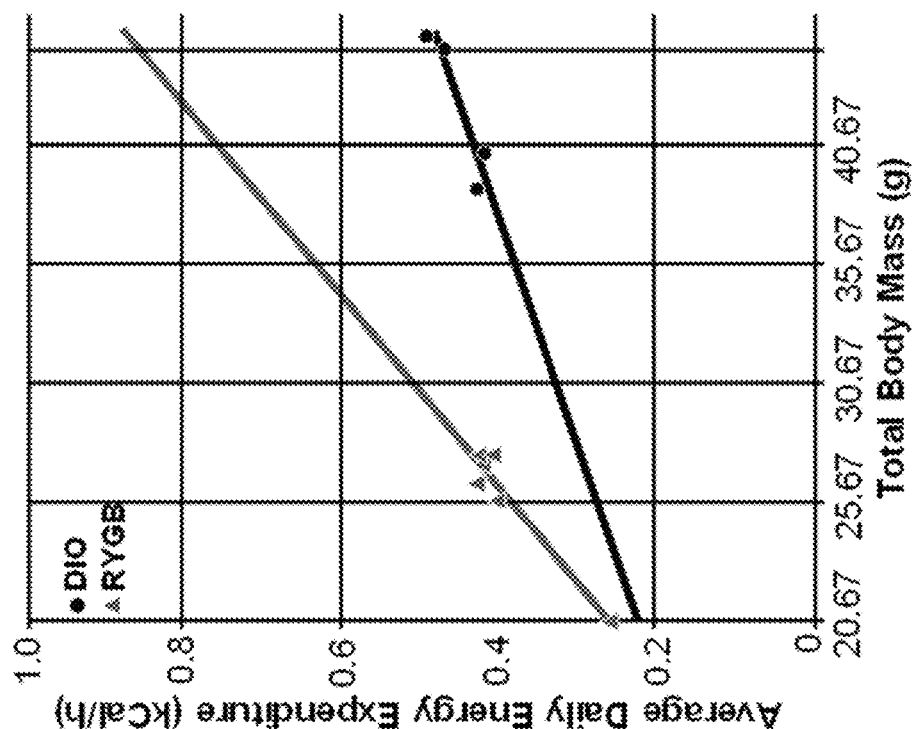
FIGS. 13A and 13B show regression lines for ANCOVA predicted energy expenditure adjusted for total body mass (TBM) when comparing GB-IL (N=6) versus DIO (N=4) (FIG. 13A) and RYGB (N=6) versus DIO (N=4) (FIG. 13B). Energy expenditure using indirect calorimetry was measured 4 weeks after surgical procedures on diet-induced obese (DIO) mice and analyzed by analysis of covariance using surgical procedure as main effects and testing for interactions as described in the Materials and Methods and on the Mouse Metabolic Phenotyping Center website (http://www.mmpc.org). GB-IL mice compared to DIO mice displayed parallel linear regression lines suggestive of an increased energy expenditure that was independent of a TBM interaction (FIG. 13A). In contrast, ANCOVA-adjusted comparisons of RYGB to DIO controlling for TBM indicated an increased energy expenditure in RYGB mice that was dependent on a TBM interaction (FIG. 13B).
Figure 13A:
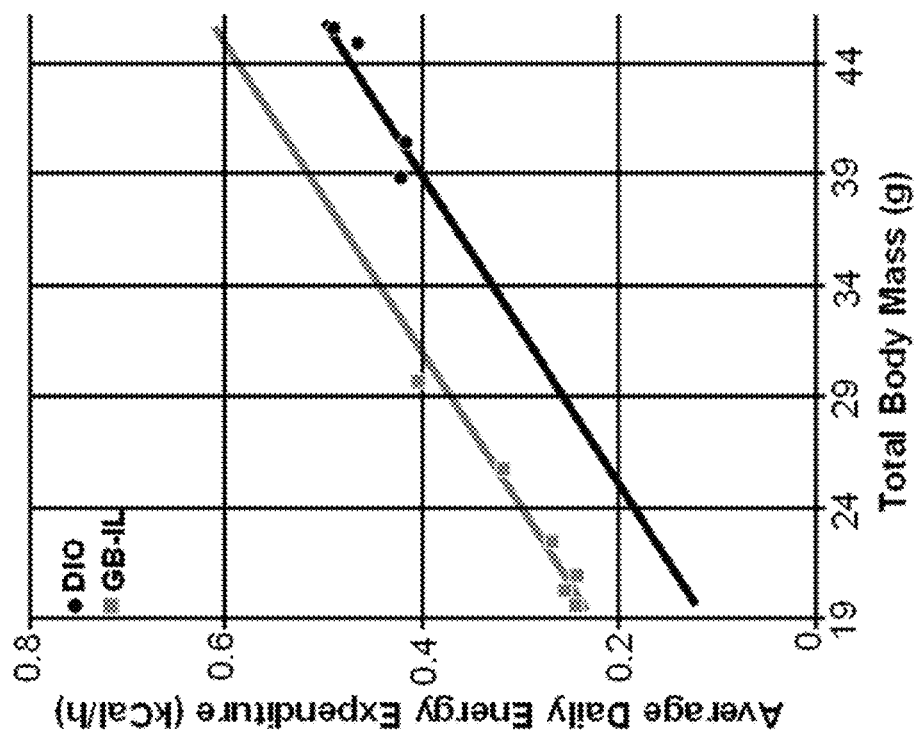

Bile acids are significantly elevated post bariatric surgery in humans (Kohli, R. et al. J. Clin. Endocrinol. Metab. 98, E708-E712 (2013); Ahmad, N. N., et al. Int. J. Obes. (Lond.) 37, 1553-1559 (2013); Patti, M. E. et al. Obesity (Silver Spring) 17, 1671-1677 (2009); Nakatani, H. et al. Metabolism 58, 1400-1407 (2009); Simonen, M. et al. Obes. Surg. 22, 1473-1480 (2012); Steinert, R. E. et al. Obesity (Silver Spring) 21, E660-E668 (2013)) and in the GB-IL model (FIG. 2) and have been shown to increase energy expenditure (EE) through TGR5-mediated processes in skeletal muscle and adipose tissue (Svensson, P. A. et al. Biochem. Biophys. Res. Commun. 433, 563-566 (2013); Thomas, C. et al. Cell Metab. 10, 167-177 (2009); Watanabe, M. et al. Nature 439, 484-489 (2006)). To explore whether changes in EE also contributed to the metabolic improvements in this model, cohorts of DIO, RYGB and GB-IL mice were subjected to 24 h indirect calorimetry under standard conditions at 4 weeks post-operative (FIG. 4A). Analysis of covariance (ANCOVA) was used to adjust EE variables for the group differences in body weight. Measurements of activity, lean mass, fat mass, food intake and locomotor activity were also made concurrently. At the time of calorimetry, RYGB and GB-IL groups weighed significantly less than DIO controls (26.6±1.1 g for RYGB; 26.2±2.4 g for GB-IL and 45.3±2.3 g for DIO; mean±s.e.m., n=4). On a per mouse basis, EE (kcal h⁻¹) in GB-IL mice (0.29±0.057) and RYGB mice (0.39±0.064) was less than DIO controls (0.45±0.031) (FIG. 4B). ANCOVA was used to assess the impact of bariatric procedures after adjusting for total body mass (TBM) or fat-free mass (FFM) (FIG. 13, Table 3). Both GB-IL and RYGB mice, relative to DIO controls, displayed increased, ANCOVA model-predicted EEs values (FIG. 4C).

Figure 4D:
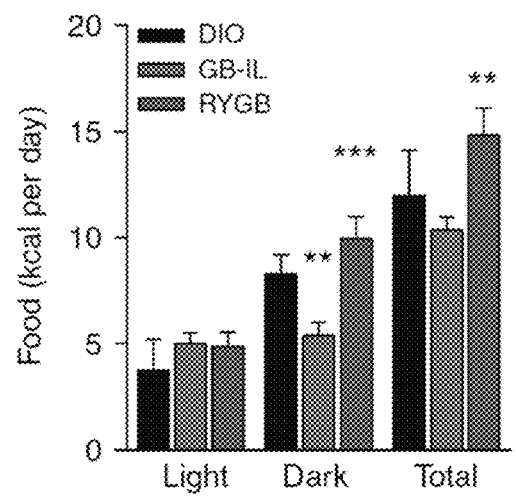
Figure 4E:
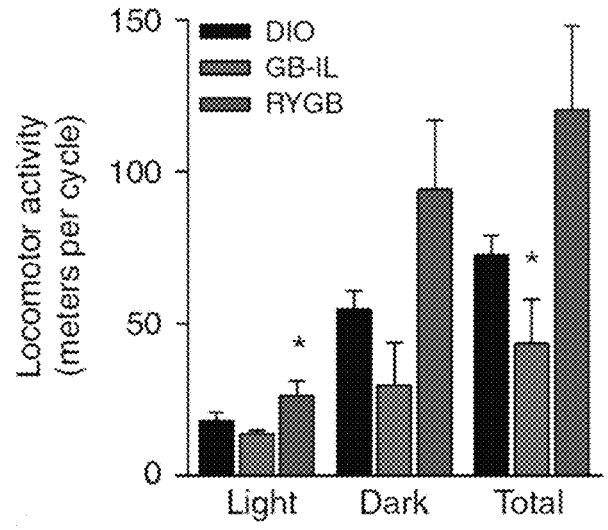

Daily food intake (FIG. 4D) was significantly lower during the dark cycle in GB-IL, but was significantly higher in RYGB in both the dark cycle and during the total 24 h period. The frequency of locomotor activity showed a similar differential trend with mice receiving GB-IL displaying a lower number of pedestrian meters travelled compared with DIO or RYGB (FIG. 4E). Locomotor activity in RYGB mice tended to be greater than that in DIO controls.

TABLE 3

Basic mean and two-way ANOVA contrasts adjusted for total body mass (TBM) and fat-free mass (FFM).

| | | | Basic Stats | | | | Model Overall | | | | | |
|---|---|---|---|---|---|---|---|---|---|---|---|---|
| Covariate | Phase | Variable | DIO | GBIL | DIO | RYGB | DIO | GBIL | p-value | DIO | RYGB | p value |
| TBM | Light | Avg_EE | 0.42 (0.031) | 0.28 (0.037) | 0.42 (0.031) | 0.36 (0.052) | 0.3 (0.013) | 0.36 (0.009) | 0.016 | 0.32 (0.03) | 0.5 (0.019) | 0.003 |
| FFM | Light | Avg_EE | 0.42 (0.031) | 0.28 (0.037) | 0.42 (0.031) | 0.36 (0.052) | 0.36 (0.012) | 0.32 (0.009) | 0.050 | 0.37 (0.017) | 0.4 (0.013) | 0.241 |
| TBM | Light | Tot_EE | 4.32 (0.321) | 2.9 (0.391) | 4.32 (0.321) | 3.75 (0.547) | 3.07 (0.135) | 3.73 (0.093) | 0.019 | 3.31 (0.32) | 5.13 (0.203) | 0.003 |
| FFM | Light | Tot_EE | 4.32 (0.321) | 2.9 (0.391) | 4.32 (0.321) | 3.75 (0.547) | 3.74 (0.122) | 3.28 (0.09) | 0.040 | 3.78 (0.169) | 4.11 (0.129) | 0.227 |
| TBM | Light | Avg_VO2 | 1.45 (0.108) | 0.98 (0.134) | 1.45 (0.108) | 1.26 (0.18) | 1.03 (0.047) | 1.26 (0.033) | 0.018 | 0.93 (0.099) | 1.61 (0.068) | 0.004 |
| FFM | Light | Avg_VO2 | 1.45 (0.108) | 0.98 (0.134) | 1.45 (0.108) | 1.26 (0.18) | 1.26 (0.044) | 1.1 (0.033) | 0.055 | 1.28 (0.058) | 1.38 (0.044) | 0.269 |
| TBM | Light | Avg_VCO2 | 1.13 (0.087) | 0.79 (0.087) | 1.13 (0.087) | 0.99 (0.145) | 0.83 (0.037) | 0.99 (0.025) | 0.035 | 0.85 (0.079) | 1.36 (0.05) | 0.002 |
| FFM | Light | Avg_VCO2 | 1.13 (0.087) | 0.79 (0.087) | 1.13 (0.087) | 0.99 (0.145) | 0.99 (0.032) | 0.88 (0.023) | 0.051 | 0.98 (0.045) | 1.09 (0.034) | 0.143 |
| TBM | Light | Avg_RQ | 0.77 (0.007) | 0.81 (0.028) | 0.77 (0.007) | 0.79 (0.008) | 0.81 (0.03) | 0.78 (0.021) | 0.639 | 0.76 (0.011) | 0.79 (0.008) | 0.107 |
| FFM | Light | Avg_RQ | 0.77 (0.007) | 0.81 (0.028) | 0.77 (0.007) | 0.79 (0.008) | 0.79 (0.018) | 0.8 (0.014) | 0.747 | 0.77 (0.005) | 0.79 (0.004) | 0.031 |
| TBM | Dark | Avg_EE | 0.48 (0.032) | 0.29 (0.078) | 0.48 (0.032) | 0.41 (0.078) | 0.36 (0.044) | 0.46 (0.021) | 0.081 | 0.38 (0.044) | 0.61 (0.028) | 0.004 |
| FFM | Dark | Avg_EE | 0.48 (0.032) | 0.29 (0.078) | 0.48 (0.032) | 0.41 (0.078) | 0.38 (0.022) | 0.36 (0.016) | 0.599 | 0.41 (0.021) | 0.46 (0.016) | 0.108 |
| TBM | Dark | Tot_EE | 5.76 (0.383) | 3.51 (0.941) | 5.76 (0.383) | 4.95 (0.93) | 4.28 (0.534) | 5.52 (0.25) | 0.081 | 4.5 (0.524) | 7.28 (0.332) | 0.004 |
| FFM | Dark | Tot_EE | 5.76 (0.383) | 3.51 (0.941) | 5.76 (0.383) | 4.95 (0.93) | 4.54 (0.261) | 4.33 (0.193) | 0.599 | 4.87 (0.253) | 5.54 (0.192) | 0.108 |
| TBM | Dark | Avg_VO2 | 1.66 (0.11) | 1.01 (0.274) | 1.66 (0.11) | 1.42 (0.263) | 0.92 (0.121) | 1.51 (0.084) | 0.020 | 1.3 (0.154) | 2.08 (0.098) | 0.005 |
| FFM | Dark | Avg_VO2 | 1.66 (0.11) | 1.01 (0.274) | 1.66 (0.11) | 1.42 (0.263) | 1.31 (0.077) | 1.25 (0.057) | 0.629 | 1.41 (0.072) | 1.59 (0.055) | 0.131 |
| TBM | Dark | Avg_VCO2 | 1.32 (0.092) | 0.8 (0.206) | 1.32 (0.092) | 1.16 (0.233) | 0.75 (0.087) | 1.18 (0.06) | 0.018 | 1.02 (0.119) | 1.75 (0.076) | 0.002 |
| FFM | Dark | Avg_VCO2 | 1.32 (0.092) | 0.8 (0.206) | 1.32 (0.092) | 1.16 (0.233) | 1.04 (0.055) | 0.98 (0.04) | 0.469 | 1.09 (0.063) | 1.3 (0.048) | 0.056 |
| TBM | Dark | Avg_RQ | 0.79 (0.01) | 0.79 (0.024) | 0.79 (0.01) | 0.81 (0.027) | 0.8 (0.028) | 0.78 (0.02) | 0.744 | 0.75 (0.028) | 0.84 (0.02) | 0.087 |
| FFM | Dark | Avg_RQ | 0.79 (0.01) | 0.79 (0.024) | 0.79 (0.01) | 0.81 (0.027) | 0.79 (0.017) | 0.79 (0.013) | 0.860 | 0.77 (0.014) | 0.82 (0.011) | 0.059 |
| TBM | Total | Avg_EE | 0.45 (0.031) | 0.29 (0.057) | 0.45 (0.031) | 0.39 (0.064) | 0.28 (0.02) | 0.4 (0.014) | 0.010 | 0.35 (0.033) | 0.55 (0.021) | 0.002 |
| FFM | Total | Avg_EE | 0.45 (0.031) | 0.29 (0.057) | 0.45 (0.031) | 0.39 (0.064) | 0.37 (0.015) | 0.34 (0.011) | 0.221 | 0.39 (0.018) | 0.43 (0.014) | 0.137 |
| TBM | Total | Tot_EE | 10.08 (0.699) | 6.41 (1.325) | 10.08 (0.699) | 8.7 (1.467) | 6.29 (0.48) | 8.94 (0.333) | 0.011 | 7.81 (0.763) | 12.41 (0.484) | 0.002 |
| FFM | Total | Tot_EE | 10.08 (0.699) | 6.41 (1.325) | 10.08 (0.699) | 8.7 (1.467) | 8.29 (0.346) | 7.61 (0.256) | 0.234 | 8.65 (0.403) | 9.65 (0.306) | 0.131 |
| TBM | Total | Avg_VO2 | 1.56 (0.108) | 0.99 (0.203) | 1.56 (0.108) | 1.34 (0.219) | 0.98 (0.074) | 1.38 (0.051) | 0.011 | 1.21 (0.116) | 1.9 (0.073) | 0.002 |
| FFM | Total | Avg_VO2 | 1.56 (0.108) | 0.99 (0.203) | 1.56 (0.108) | 1.34 (0.219) | 1.28 (0.055) | 1.18 (0.041) | 0.243 | 1.34 (0.062) | 1.48 (0.047) | 0.162 |
| TBM | Total | Avg_VCO2 | 1.22 (0.089) | 0.79 (0.145) | 1.22 (0.089) | 1.08 (0.187) | 0.79 (0.047) | 1.08 (0.033) | 0.007 | 0.94 (0.086) | 1.55 (0.054) | 0.001 |
| FFM | Total | Avg_VCO2 | 1.22 (0.089) | 0.79 (0.145) | 1.22 (0.089) | 1.08 (0.187) | 1.02 (0.036) | 0.93 (0.027) | 0.150 | 1.04 (0.051) | 1.2 (0.039) | 0.069 |

TABLE 3-continued

Basic mean and two-way ANOVA contrasts adjusted for total body mass (TBM) and fat-free mass (FFM).

| | | | Basic Stats | | | | Model Overall | | | | | |
|---|---|---|---|---|---|---|---|---|---|---|---|---|
| Covariate | Phase | Variable | DIO | GBIL | DIO | RYGB | DIO | GBIL | p-value | DIO | RYGB | p value |
| TBM | Total | Avg_RQ | 0.78 (0.009) | 0.8 (0.025) | 0.78 (0.009) | 0.8 (0.015) | 0.8 (0.029) | 0.78 (0.02) | 0.685 | 0.75 (0.016) | 0.82 (0.011) | 0.046 |
| *FFM* | *Total* | *Avg_RQ* | *0.78 (0.009)* | *0.8 (0.025)* | *0.78 (0.009)* | *0.8 (0.015)* | *0.79 (0.017)* | *0.79 (0.013)* | *0.934* | *0.77 (0.008)* | *0.8 (0.006)* | *0.020* |

Indirect calorimetry parameters were compared by a 3-way analysis of variances using surgical procedure (GB-IL or RYGB) as main effects and testing for interactions with covariates being either total body mass (TBM) or fat-free mass (FFM; italics).
Least squares means were compared using residual variance as the error term and presented as mean ± SEM.
Abbreviations:
Avg EE, mean energy expenditure in kcal/hr;
Tot_EE, Summed energy expenditure for entire cycle;
Avg_VO2, mean volume of $O_2$ ml/min;
Avg_VCO2, mean volume of $CO_2$ ml/min;
Avg_RQ, mean respiratory quotient).

Effects of Surgical Procedures on Hepatic Gene Expression.

Figure 5A:
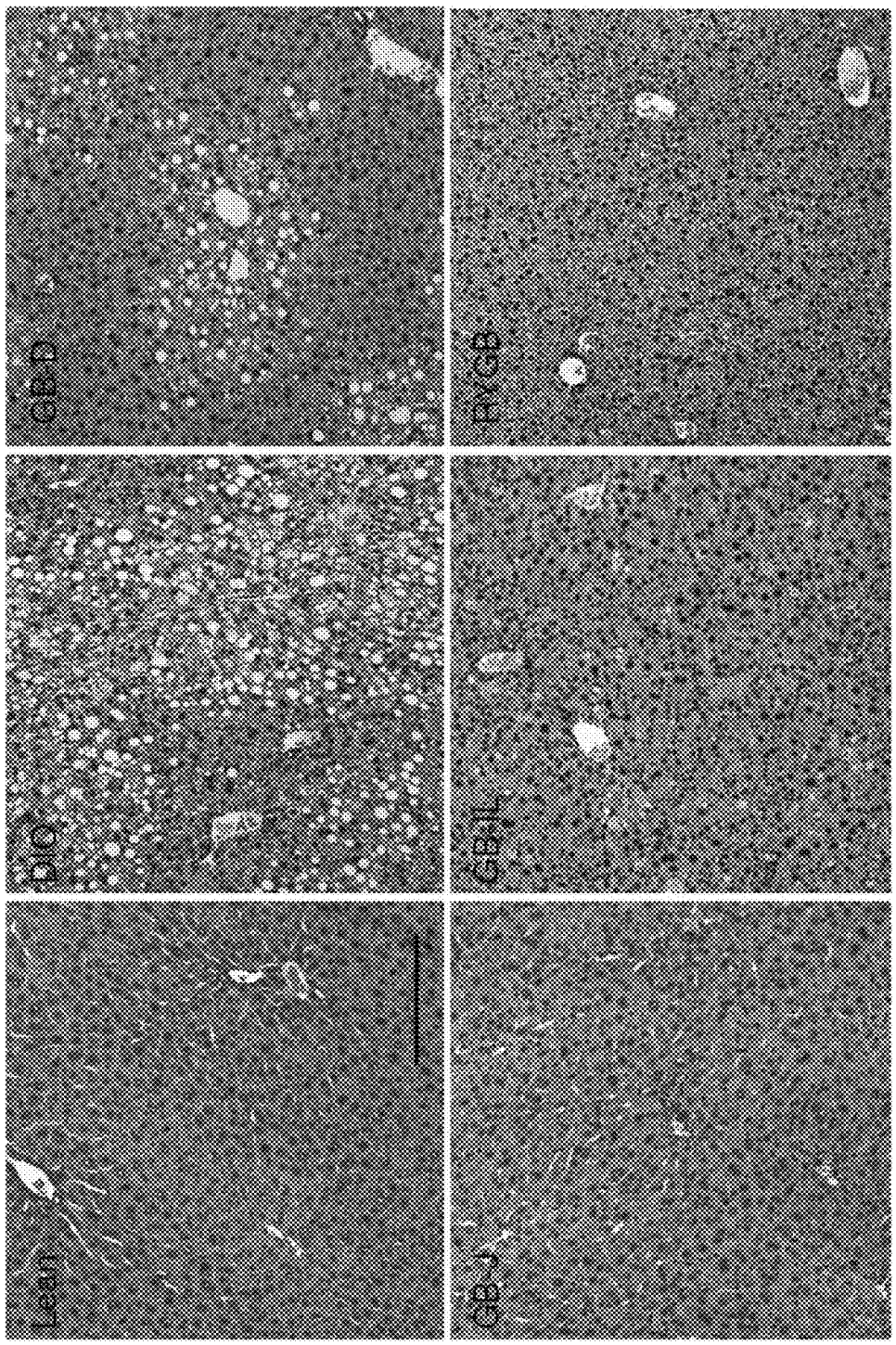
FIGS. 5A to 5L show effects of biliary diversion on liver histology and hepatic gene expression.
Figure 5B:
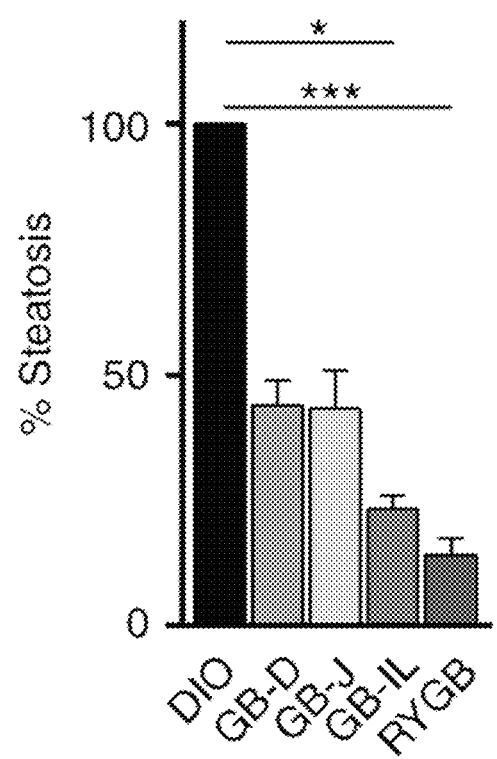

Hepatic steatosis is a frequent comorbidity of obesity and high fat feeding. Livers were harvested from all mice groups 8 weeks postoperatively for histologic analyses (FIG. 5A). The comparison included age- and gender-matched high fat or chow fed controls. HFD resulted in severe hepatic steatosis compared with the chow control diet. GB-J or GB-D mice displayed significant reductions in hepatic steatosis relative to DIO mice. However, more marked reductions in hepatic steatosis were observed after GB-IL and RYGB (FIG. 5B).

Figure 5C:
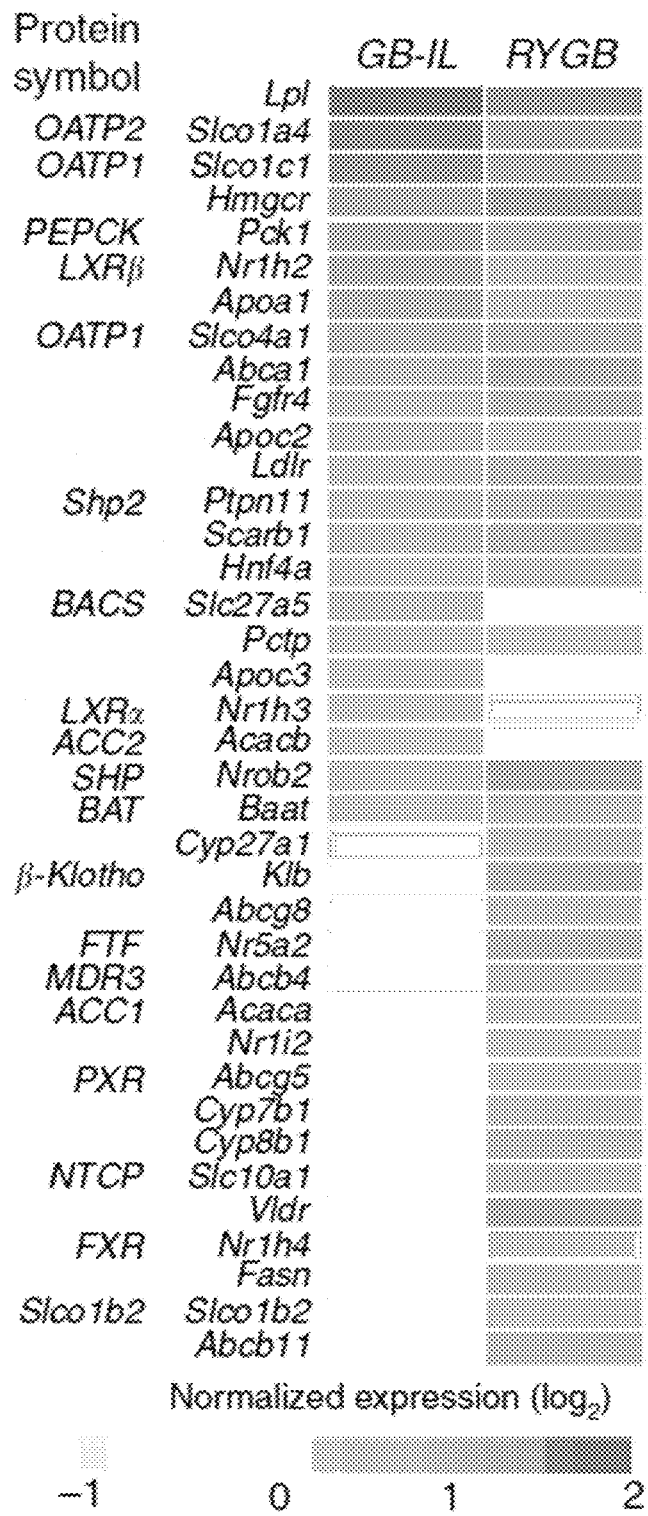
Figure 5D:
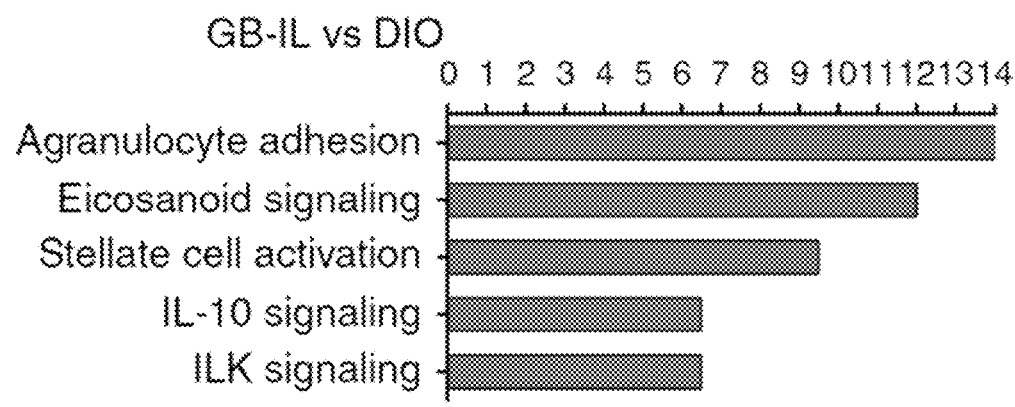
Figure 5E:
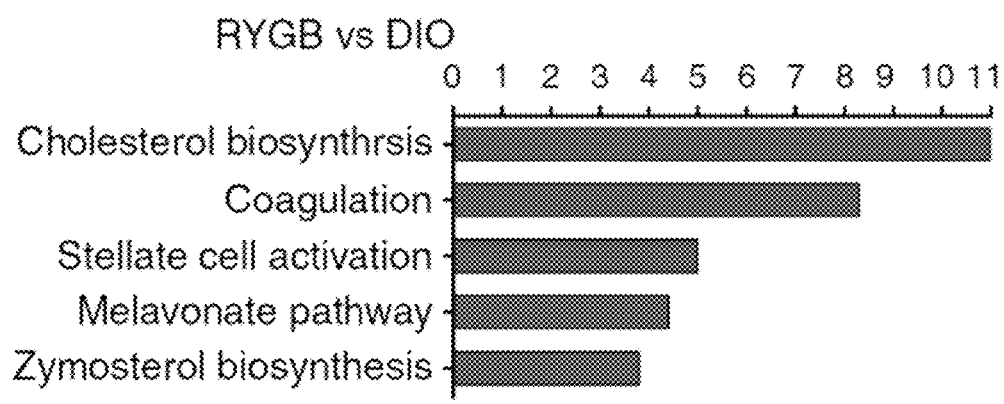
Figure 5F:
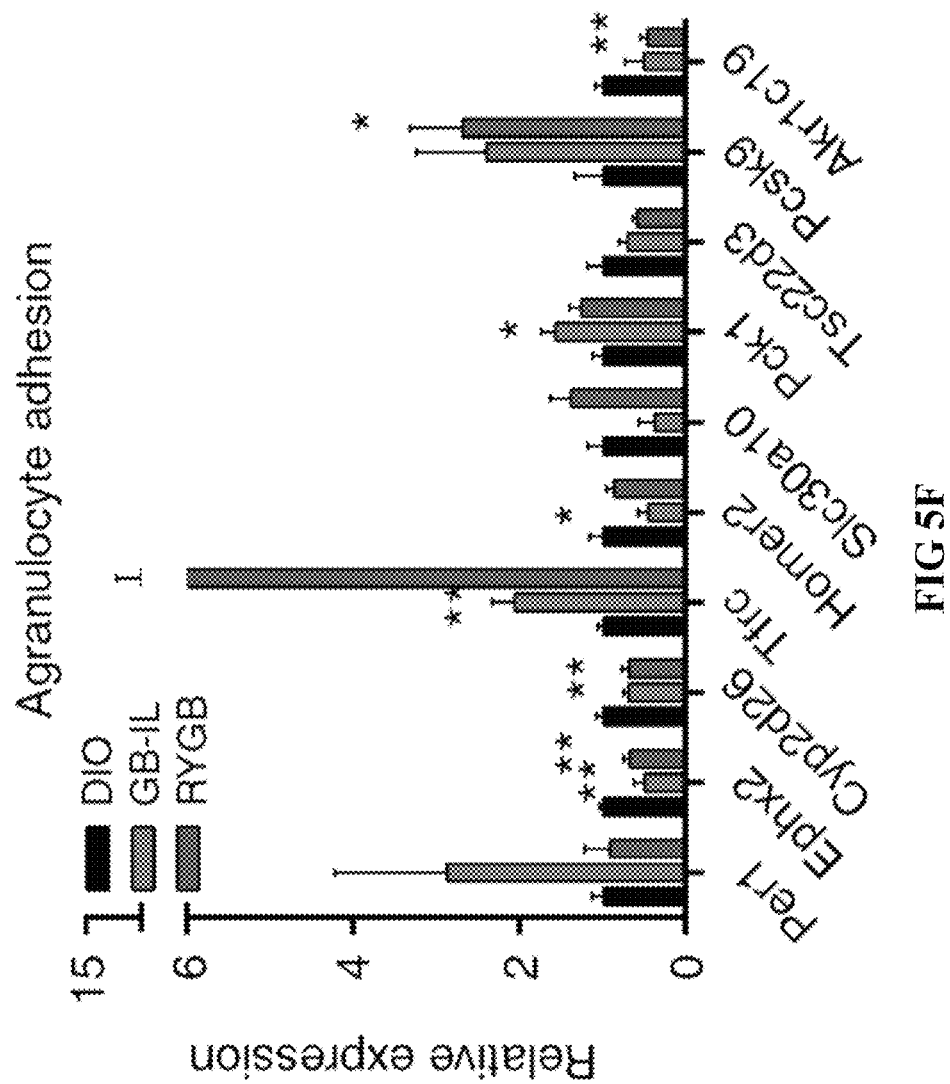
Figure 5G:
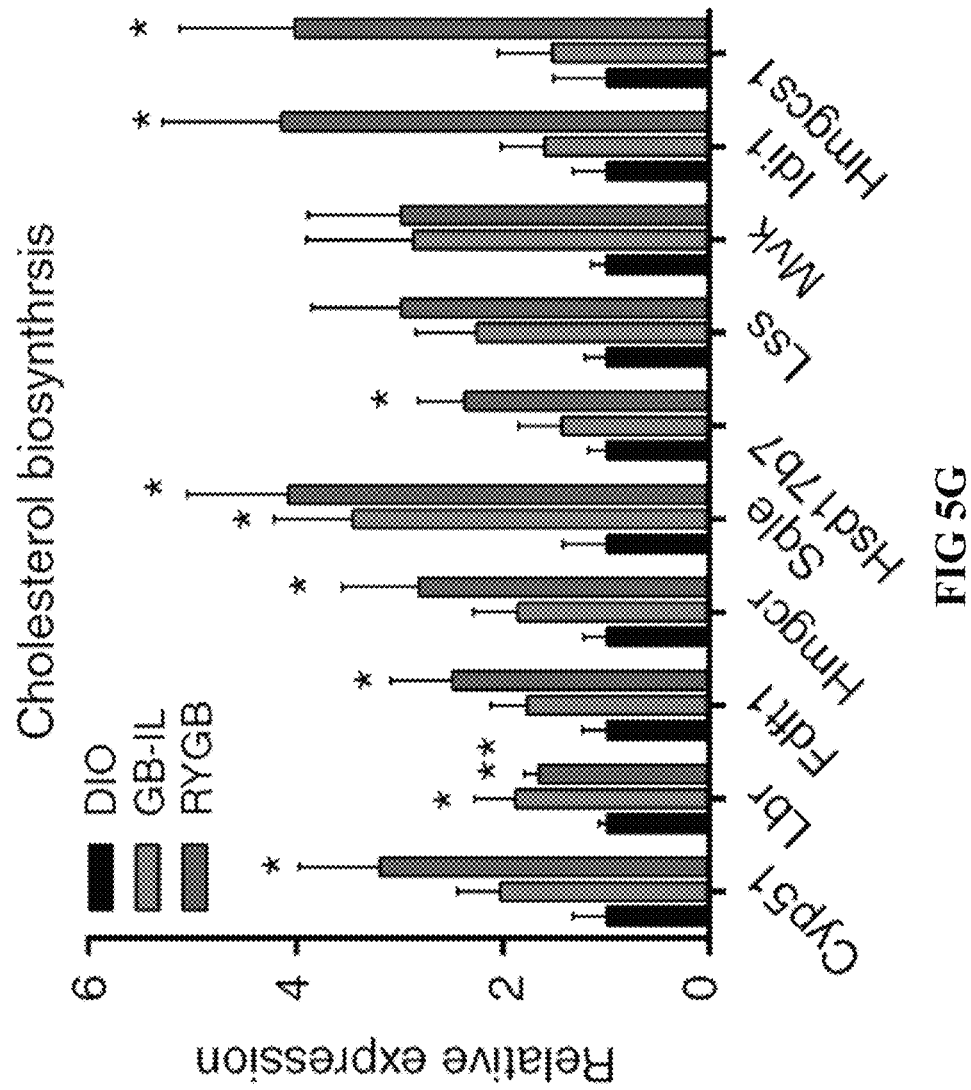
Figure 5H:
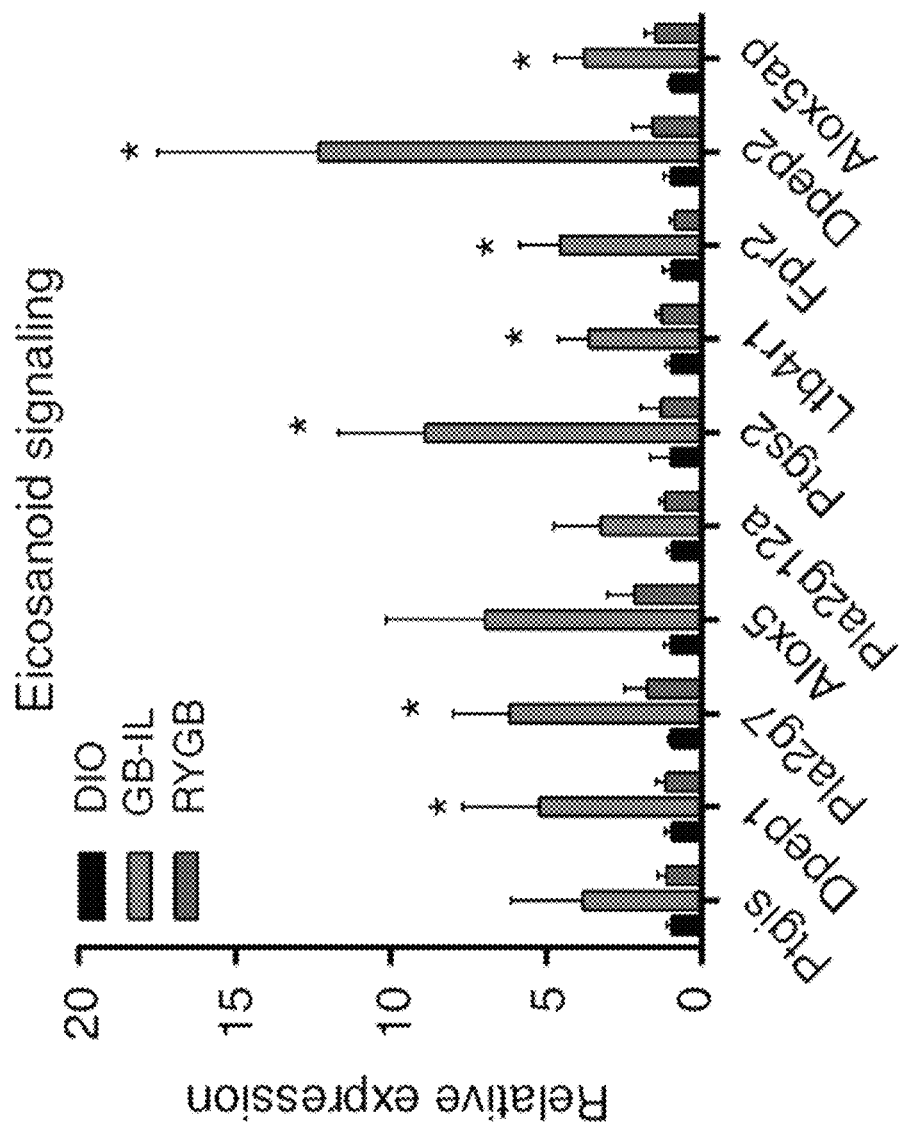
Figure 5I:
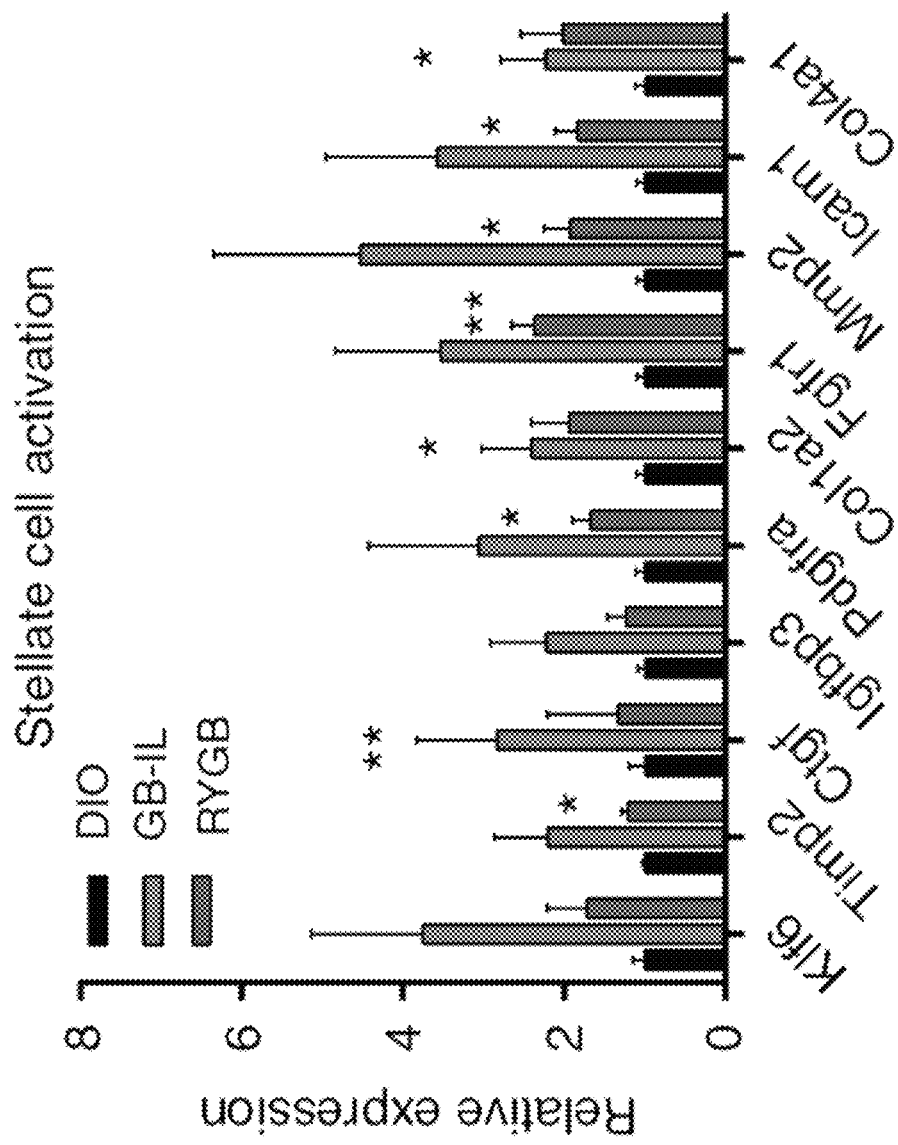
Figures 5J, 5K, 5L:
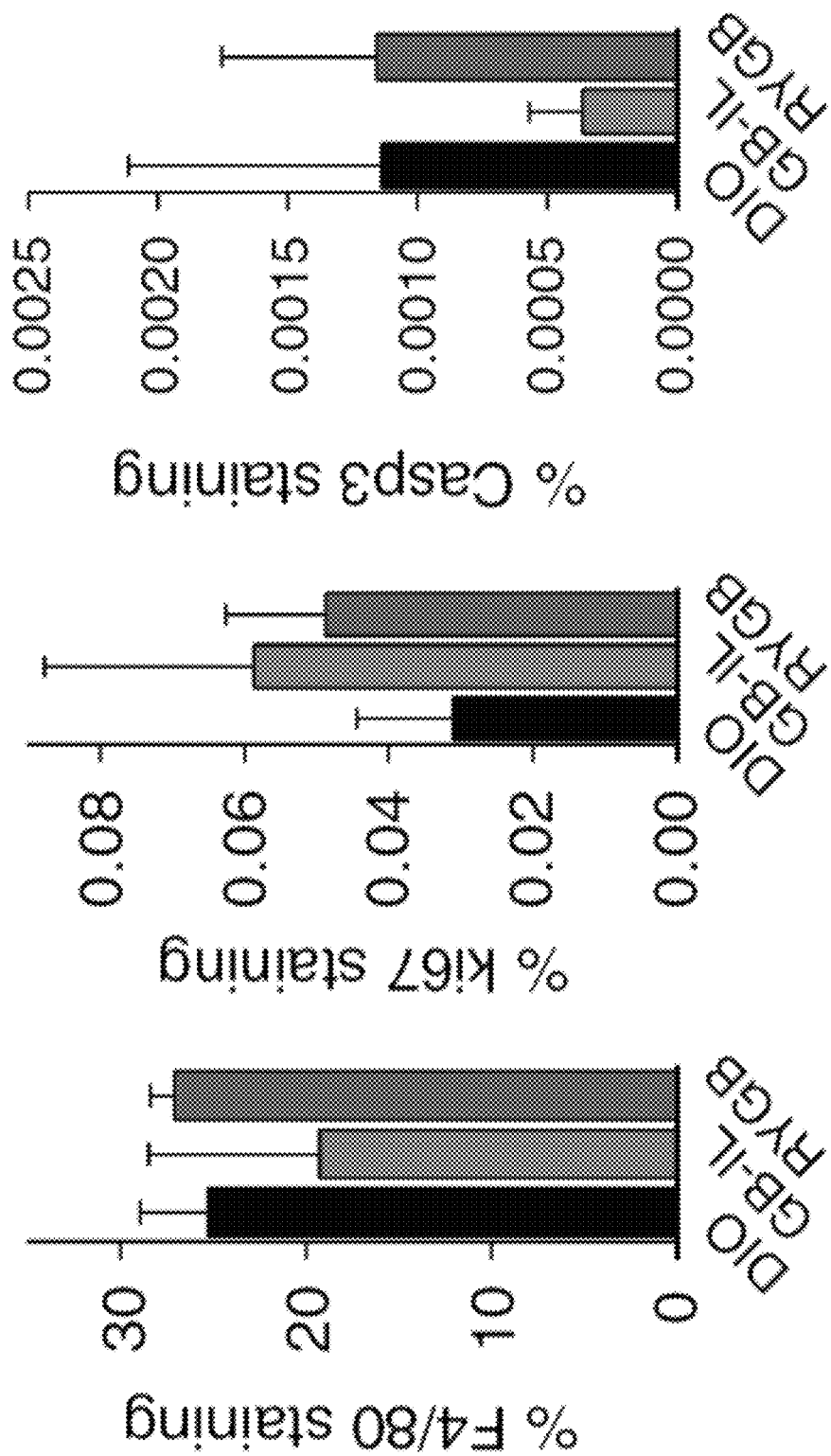
Figure 14D:
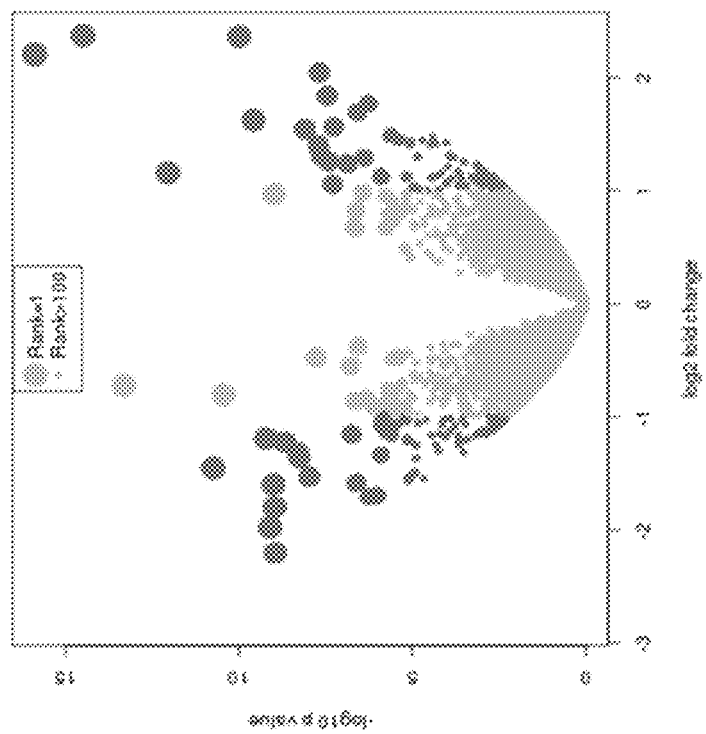
Figure 14C:
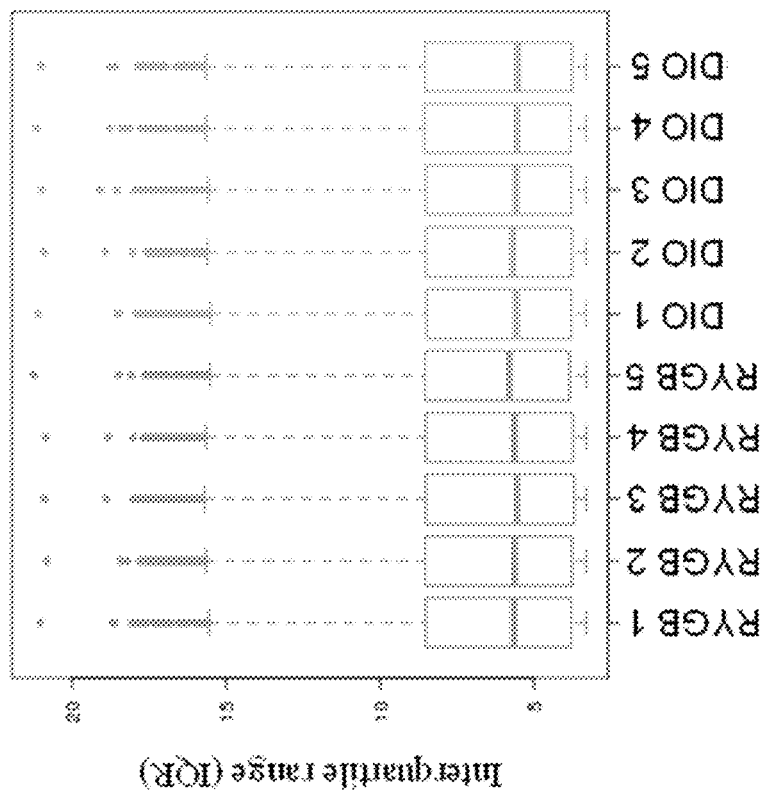
Figure 15A:
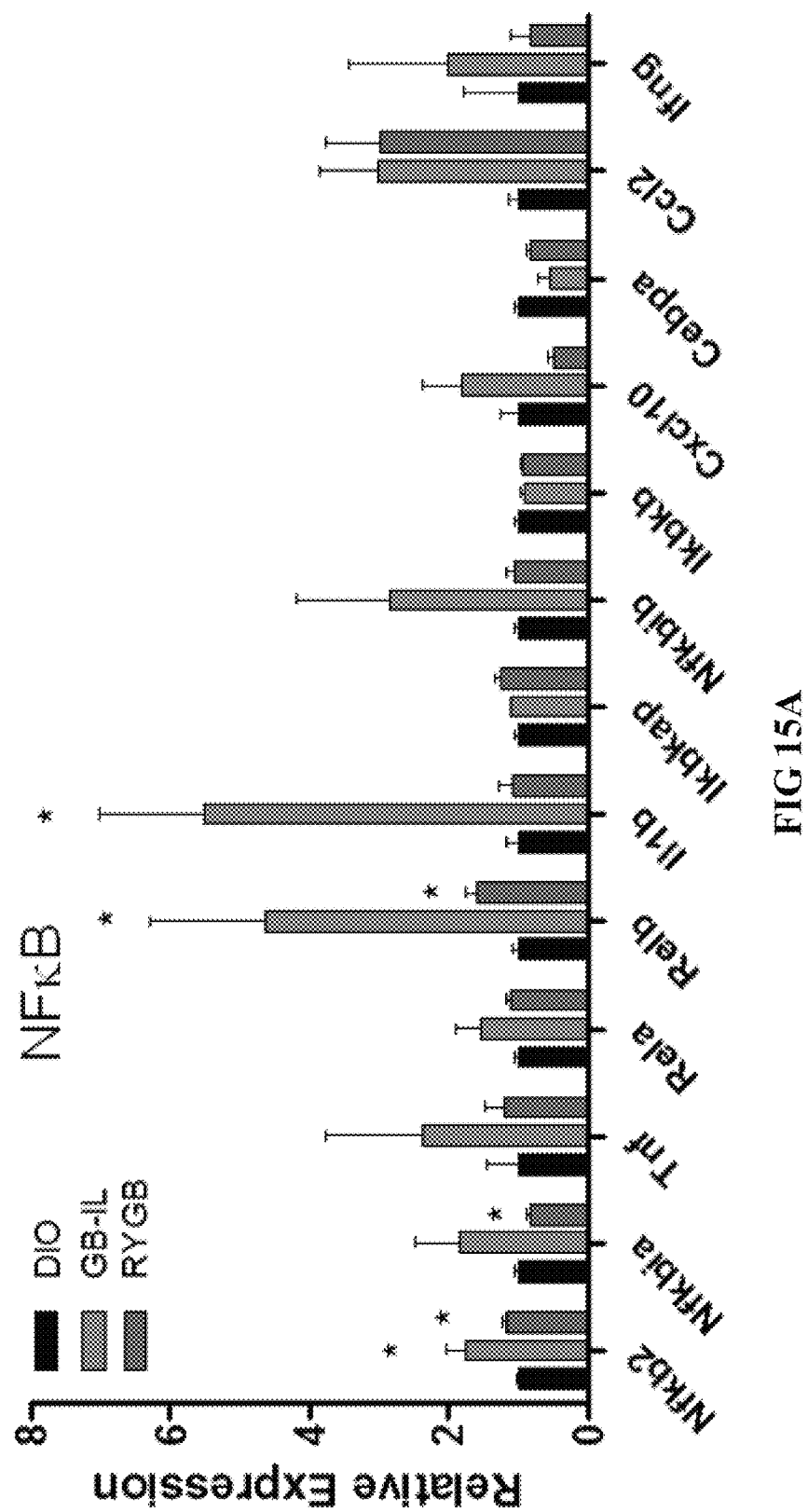
FIGS. 15A to 15D show bile diversion to the ileum (GB-IL) and RYGB have differential effects on hepatic gene expression. RNA-seq analysis of (a) NFκB-related genes (FIG. 15A), lipogenesis genes (FIG. 15B), apoptosis genes (FIG. 15C), and inflammatory genes (FIG. 15D) in the livers of DIO, GB-IL and RYGB mice as assigned to canonical pathways curated by Ingenuity Pathway Analysis. Expression was normalized. N=4-5 mice per group. Data are presented as mean±SEM, unpaired two-tailed Student's t-test. *P<0.05, *P<0.01 compared with DIO controls.
Figure 15B:
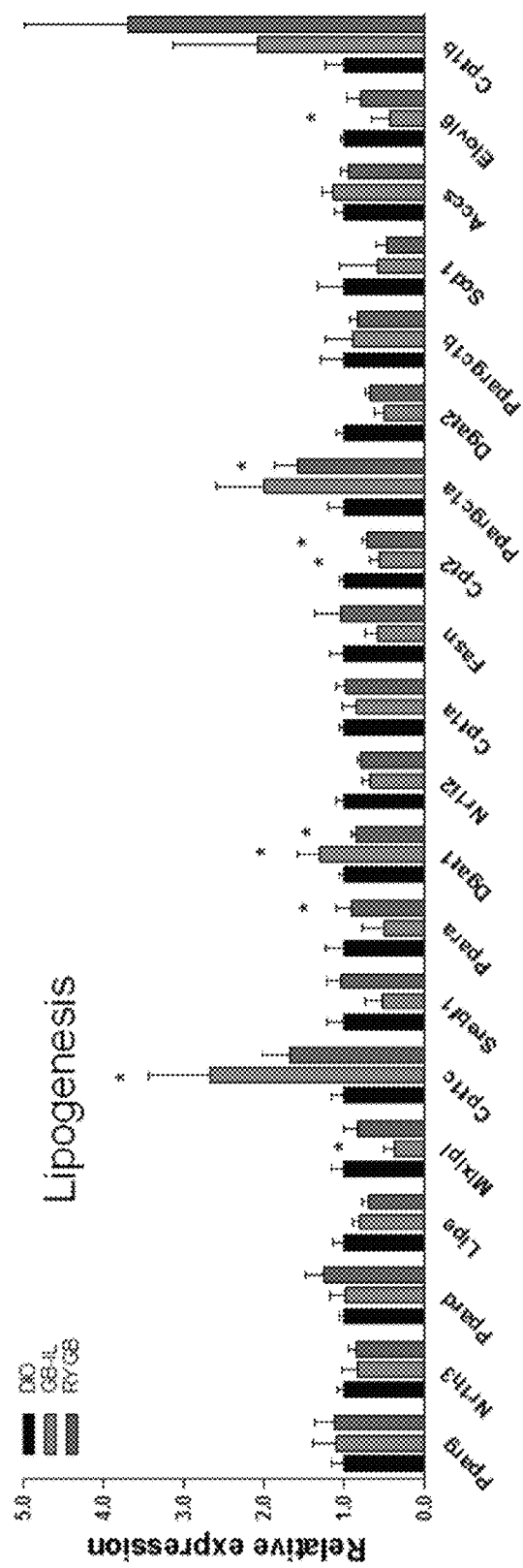
Figure 15C:
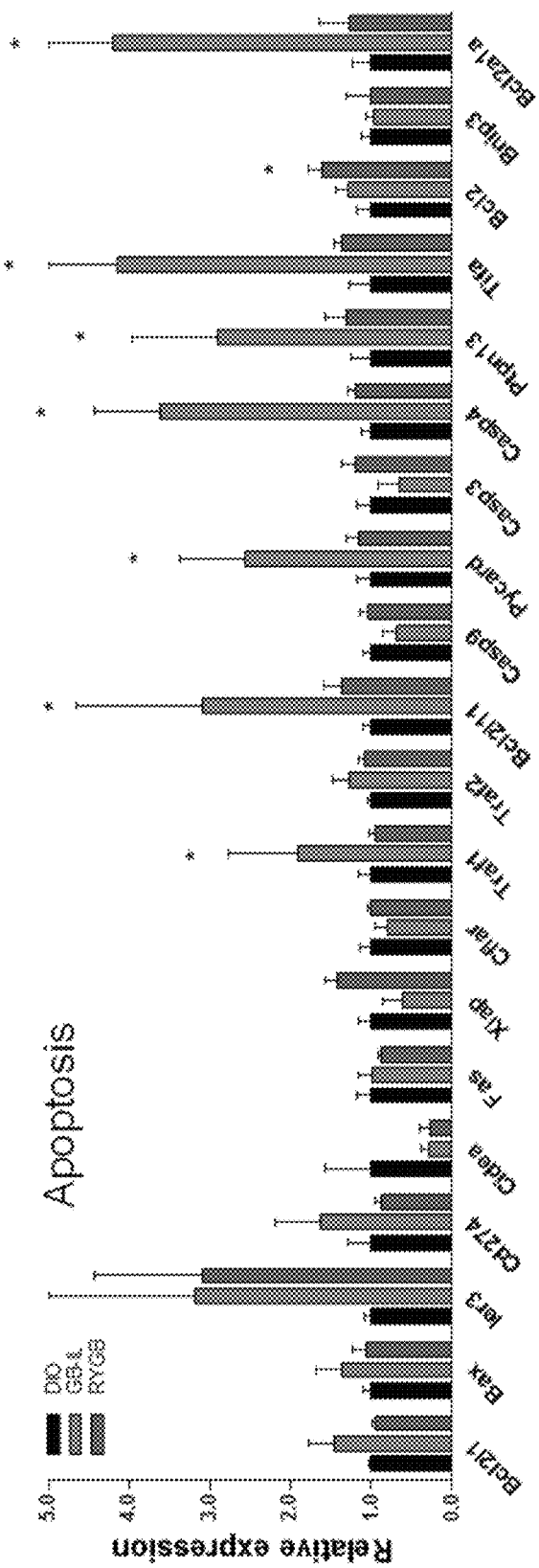
Figure 15D:
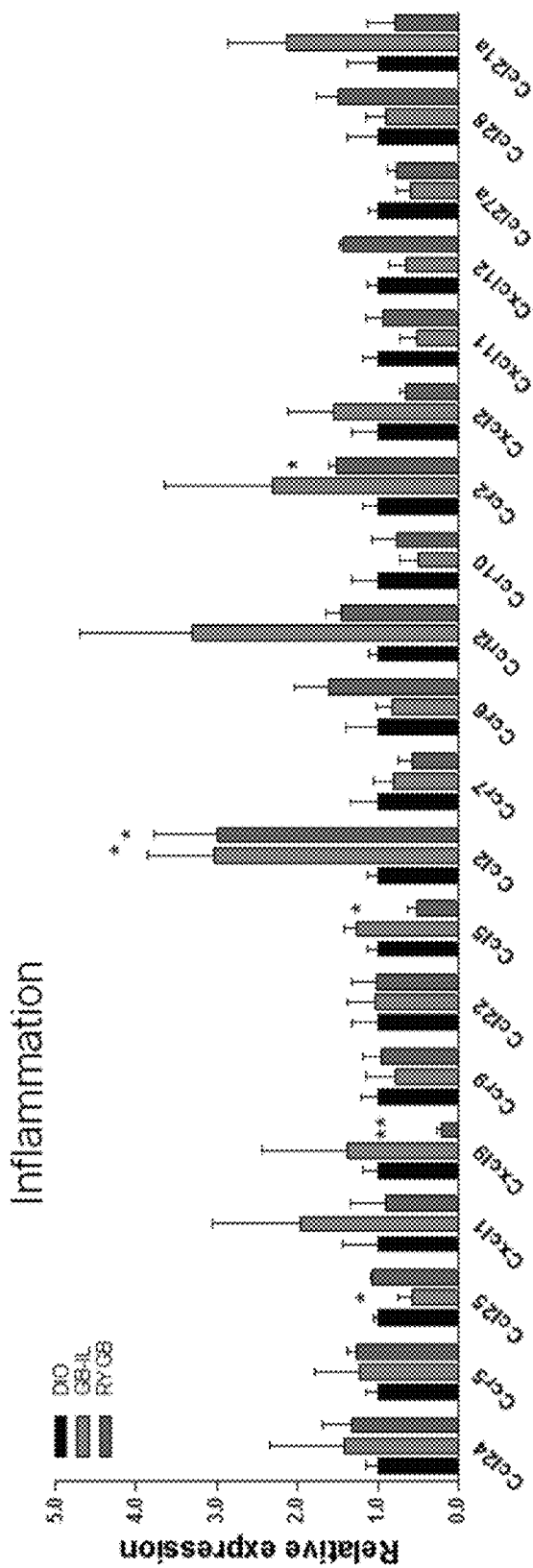
Figure 16:
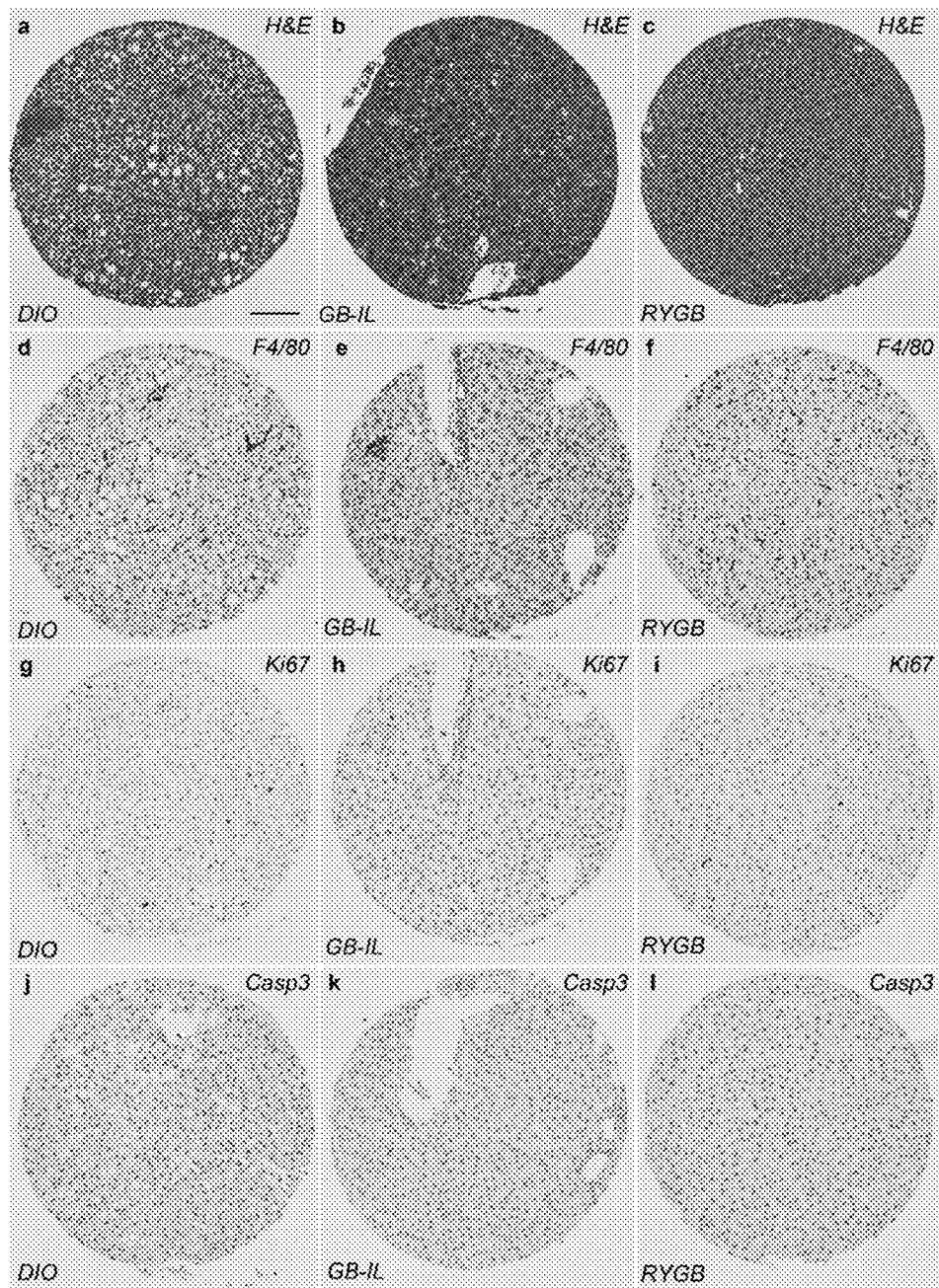
FIG. 16 shows representative micrographs of DIO, GB-IL and RYGB mouse livers at 4 weeks post-operative stained for hematoxylin and eosin (panels a-c) and F4/80 (panels d-f), Ki-67 (panels g-i) and caspase 3 (panels j-l) revealed by DAB reactivity and counter-stained for eosin. Mag bar=100 μm.

To more closely examine the hepatic changes associated with by the whole-body metabolic improvements and the apparent hepatic resistance to steatosis, changes in hepatic gene expression were examined by RNA-seq (FIG. 5C-I; FIG. 14). Genes potentially regulated by bile acids were manually interrogated for expression changes with GB-IL or RYGB (FIG. 5C). Lipoprotein lipase (Lpl) was most significantly upregulated (increased 2.4-fold relative) in mice treated with a gut-restricted FXR agonist, fexaramine, relative to DIO controls. The bile acid transporters, Slco1a4 (Oatp2) and Slco1c1 (Oatp1) were similarly upregulated in both GB-IL and RYGB groups. Such increases were in the context of relatively unchanged FXR expression. An unbiased interrogation of the mRNA transcriptome (Ingenuity Pathway Analysis, Qiagen) was conducted (FIG. 5D-I). The top three canonical pathways most increased in GB-IL versus DIO livers (FIG. 5D) included agranulocyte adhesion (FIG. 5F), eicosanoid signaling (FIG. 5H) and stellate cell activation (FIG. 5I). Those pathways that changed the greatest in RYGB versus DIO included cholesterol biosynthesis (FIG. 5G), coagulation and stellate cell activation (FIG. 5I). Some markers of NF-kB were significantly increased in GB-IL and/or RYGB mice (FIG. 15A). Interleukin-1β was only increased in GB-IL. Lipogenic targets were marginally affected in either GB-IL or RYGB (FIG. 15B). Several apoptotic and inflammatory genes also trended upward in GB-IL more so than RYGB (FIGS. 15C,D). To determine whether such gene expression changes translated into phenotypic differences, immunohistochemistry markers of inflammation were also surveyed by F4/80 (FIG. 5J, 16D-F), proliferation by Ki-67 (FIGS. 5K, 16G-I), and apoptosis was surveyed by caspase 3 staining (FIGS. 5L, 16J-L). The significant individual gene expression profiles did not appear to translate into effects on histologic phenotypes. Overall the data suggest that both RYGB and GB-IL do not result in substantially improved inflammatory markers as compared with DIO despite the complete reversal of hepatic steatosis; however, there were trends toward increased apoptotic and inflammatory responses.

Effects of Surgical Procedures of BA Transporters.

Figure 6A:
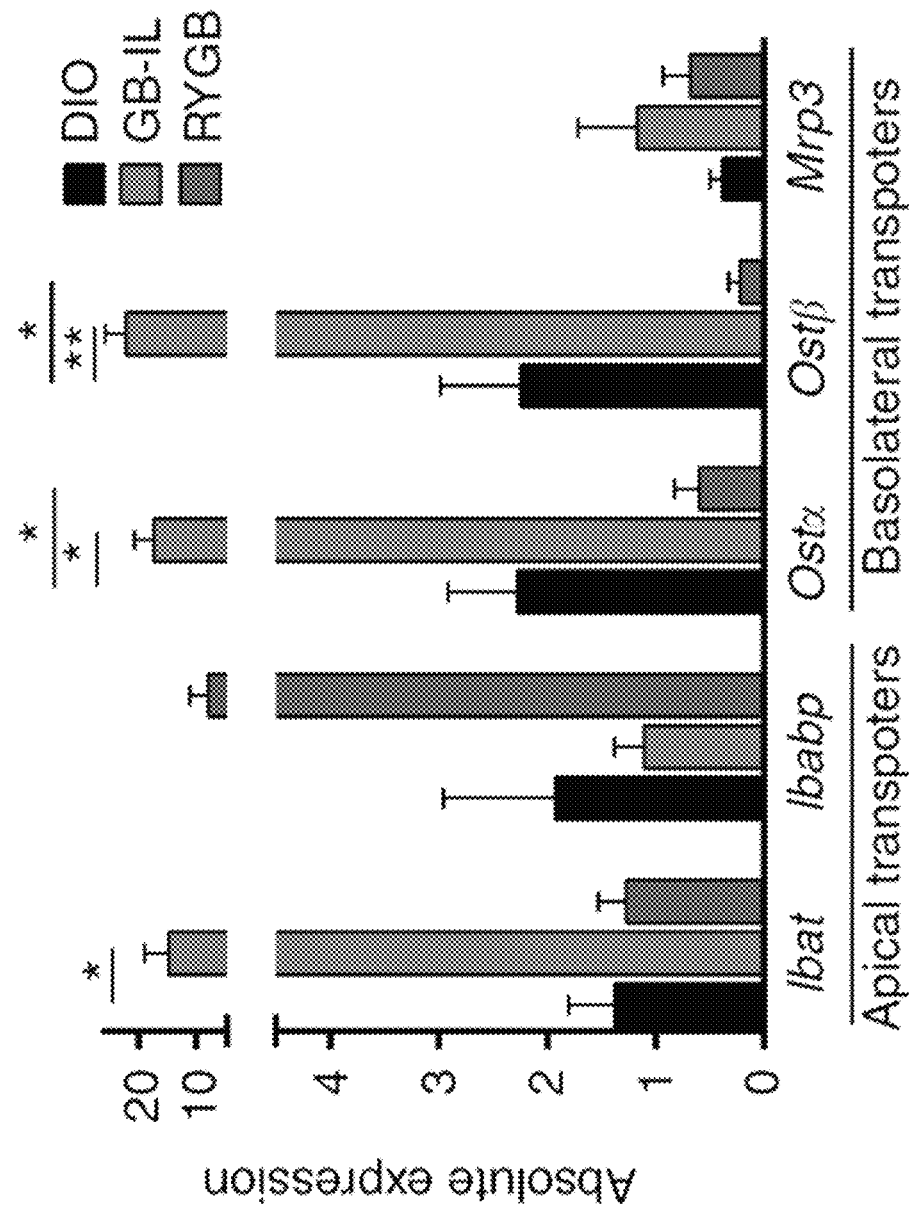
FIGS. 6A and 6B show effects of biliary diversion on ileal and hepatic gene expression. Ileum (FIG. 6A) and liver (FIG. 6B) tissues 8 weeks post-operative were harvested for gene expression analysis using RT-PCR. *P<0.05, **P<0.01 versus DIO by one-way analysis of variance followed by two-tailed Students t-test. Values shown are mean±s.e.m. N of 3-5 per group. Bacs, bile-acid-CoA synthetase; Bat, bile acid transporter; Bsep, bile sale effluent pump; Ibabp, ileal bile acid binding protein; Ibat, Ileal bile acid transporter; Mrp3, multi-drug resistance protein 3; Ntcp, Na-taurocholate cotransporting polypeptide; Ostα and Ostβ, organic solute transporter α and β.
Figure 6B:
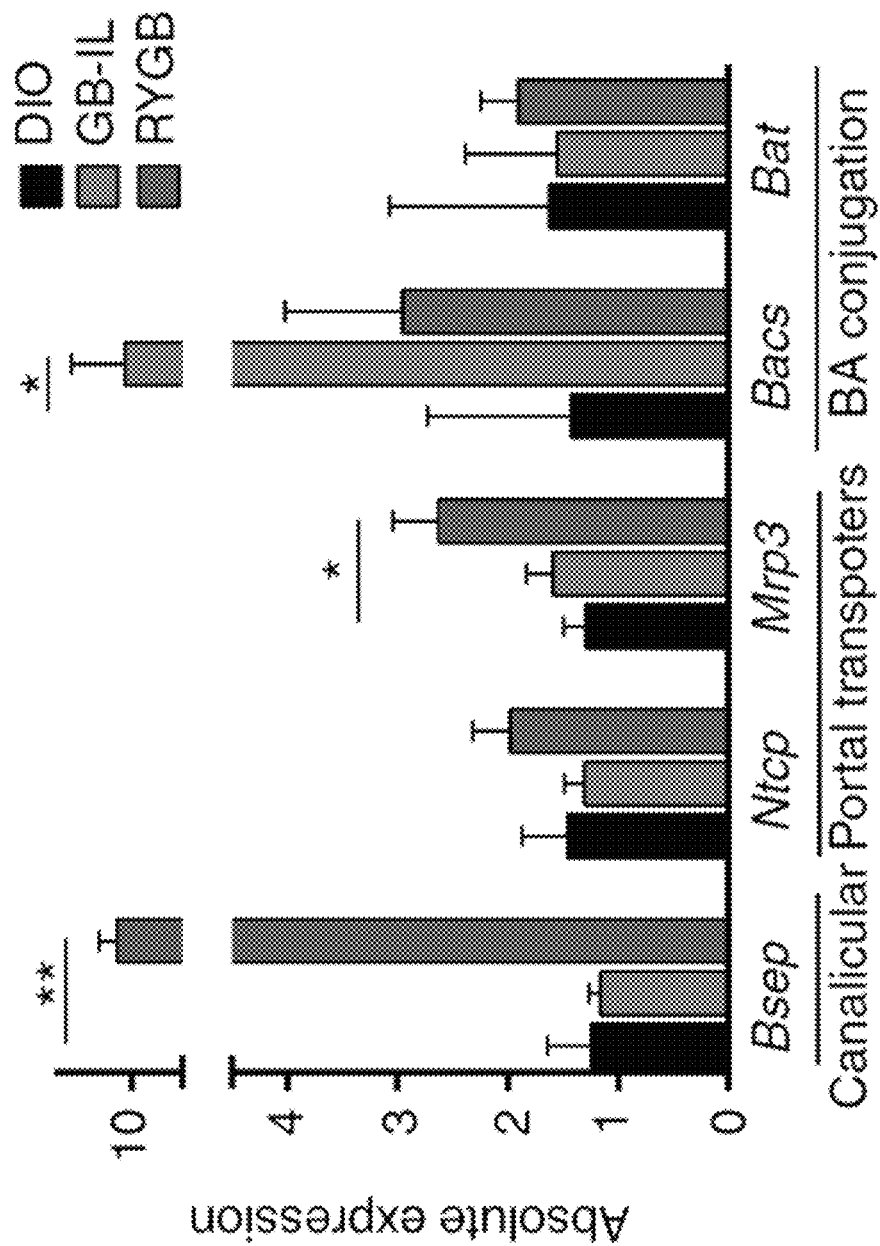

To gain insight into the mechanisms underlying the metabolic adaptations observed after GB-IL and RYGB mice as compared with DIO controls, expression of bile acid transporters was measured in the ileum and liver with additional measurements of conjugation enzymes in the liver. In the ileum (FIG. 6A), GB-IL but not RYGB markedly increased the apical ileal bile acid transporter (Ibat, up 10-fold) and the basolateral bile acid transporters Osta and Ostb (organic solute transporter α and β). GB-IL only increased the apical bile acid-binding protein. In contrast, in the liver, RYGB but not GB-IL strongly increased expression of the canalicular bile salt export pump and the portal multi-specific organic ion transporter 3 (FIG. 6B). Thus, the effect of GB-IL is predominantly on ileal bile acid transport, while RYGB enhances expression of liver bile acid transporters. RYGB, and to a greater extent GB-IL, tended to increase hepatic expression of bile-acid-CoA synthetase, the enzyme facilitating conjugation of CA with taurine, but these increases were not significant. These data are consistent with the enhanced circulation of bile acids with GB-IL.

Altered Hepatic FXR/FGF15 Signaling.

Figure 7A:
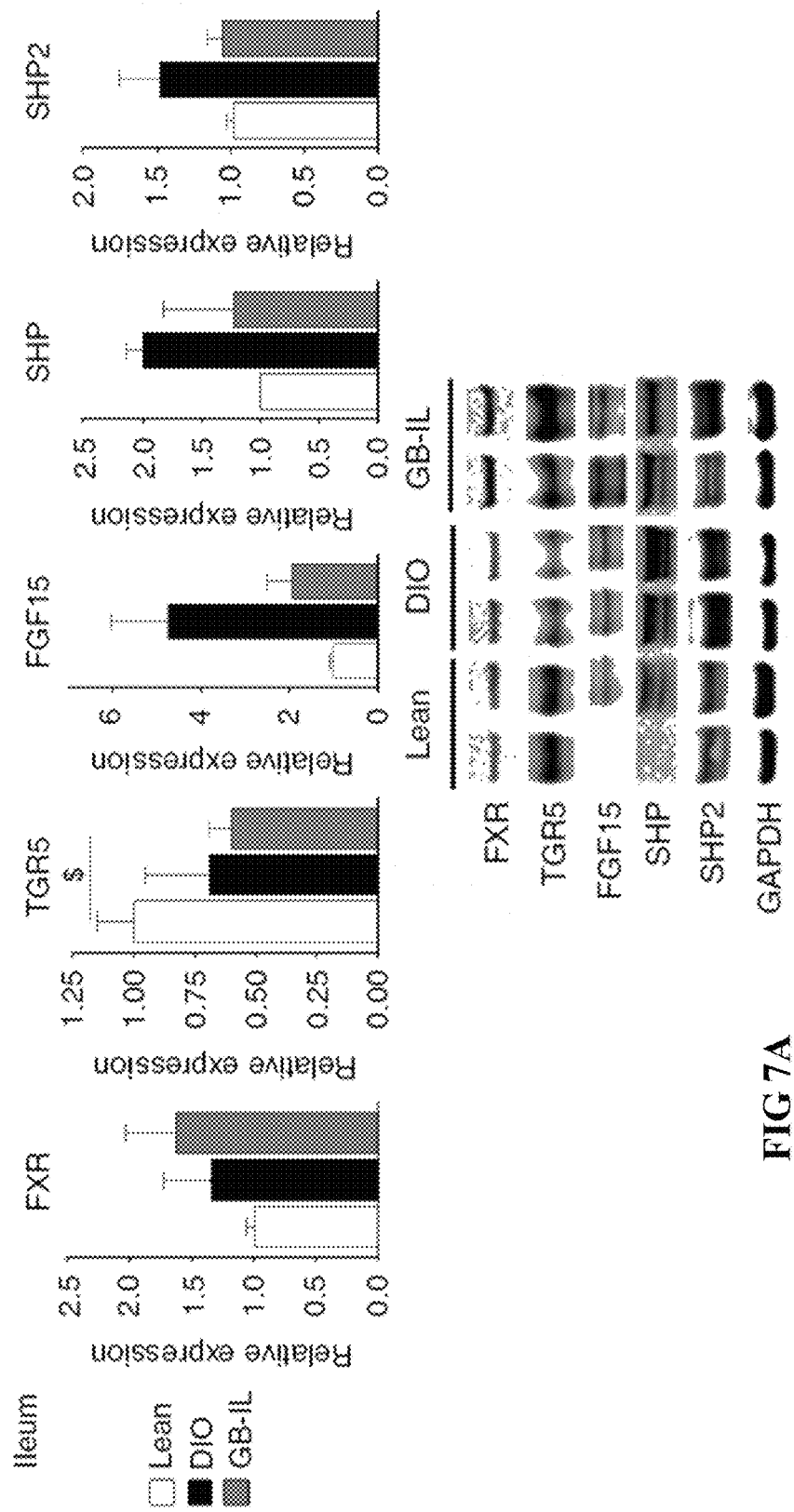
FIGS. 7A and 7B show signaling in the ileum and liver is altered after biliary diversion. Immunoblots of ileum (FIG. 7A) and liver (FIG. 7B) protein were obtained from lean, DIO and GB-IL mice 8 weeks after surgery. Expression was normalized to GAPDH. *P<0.05, **P<0.01 by one-way analysis of variance with Dunn's post-test. $^$P<0.05, $^{$$}$P<0.01, $^{$$$}$P<0.001 by two-tailed Students t-test. Values shown are mean±s.e.m. N of 3-8 per group.

Given that GB-IL procedure alone was associated with increased circulating bile acids and with increased mRNA expression of bile acid transporters (FIG. 6), next examined was the effect of GB-IL compared with lean and DIO controls with respect to bile acid signaling proteins in the ileum and liver (FIG. 7). FXR expression in the ileum trended upward after GB-IL, while that of TGR5 trended downward (FIG. 7A). GB-IL mice displayed reduced levels of FGF15, a postprandial hormone induced by bile acid and released from the small intestine into the portal circulation where it acts to repress hepatic bile acid synthesis. Expression of the small heterodimer partner (SHP) and the non-receptor tyrosine phosphatase (Shp2) in ileums of GB-IL mice was restored towards levels observed in lean chow fed mice.

It is well established that ileal reabsorption and enterohepatic circulation of bile acids negatively regulate hepatic bile acid synthesis by repressing expression of the rate-limiting enzyme cholesterol 7a-hydroxylase 1 (Cyp7a1) (Watanabe, M. et al. Nature 439, 484-489 (2006)). This effect is likely mediated by increased levels of FGF15 that bind to FGF receptor 4, leading to transactivation of SHP and Shp2 (Lu, T. T. et al. Mol. Cell 6, 507-515 (2000); Li, S. et al. Cell Metab. 20, 320-332 (2014)). Alternatively, bile acids, acting through FXR, can directly inhibit hepatic Cyp7a1 expression. Thus, under conditions of absent or low bile acids, Cyp7a1 drives bile acid synthesis via the classical pathway to restore bile acid levels; thus, high bile acid availability should decrease the expression of Cyp7a1 leading to repressed bile acid synthesis46.

Figure 7B:
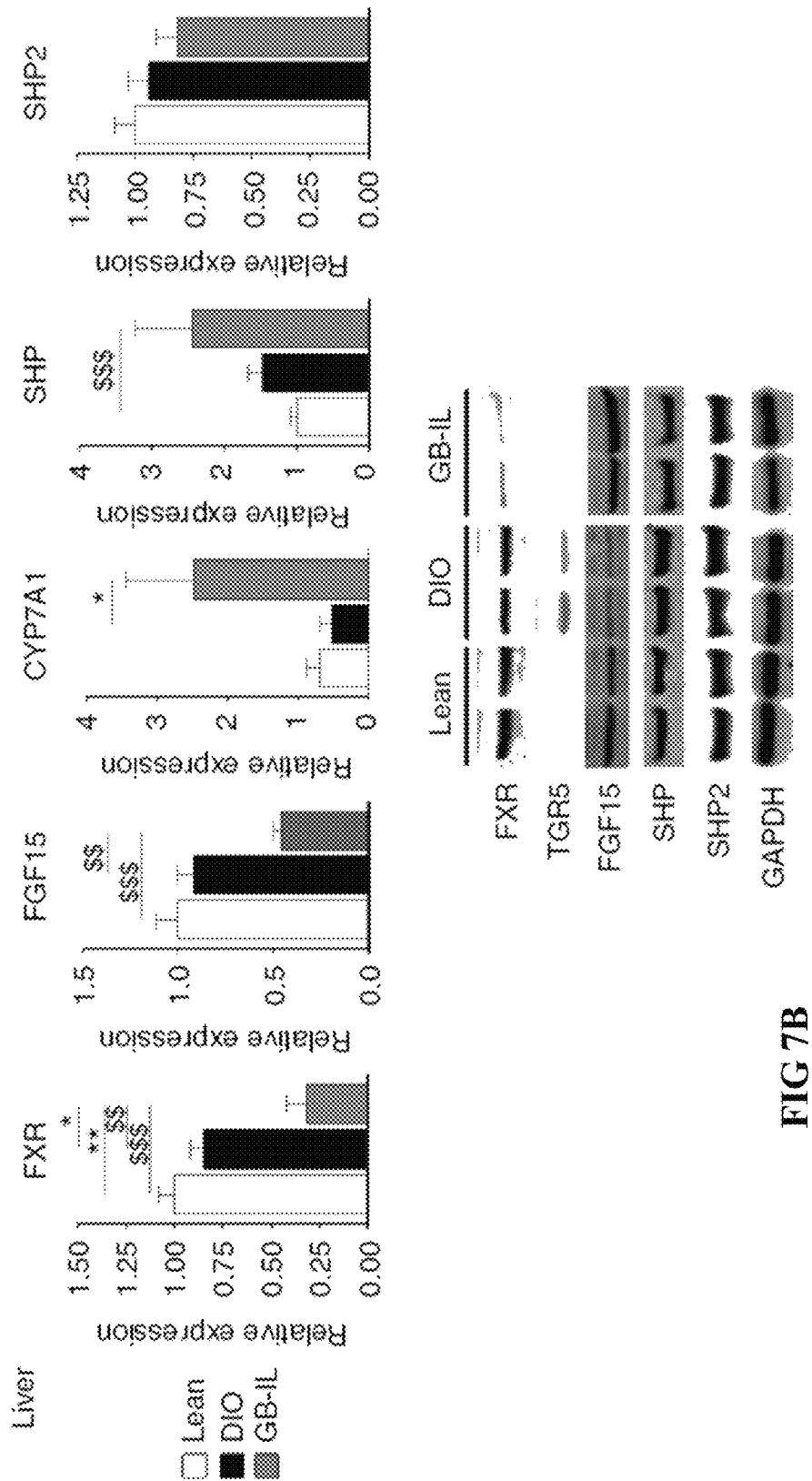

Eight weeks after surgery, GB-IL displayed significantly reduced levels of hepatic FXR relative to lean and DIO controls (FIG. 7B). Consistent with the suppression of FGF15, hepatic expression of Cyp7a1 was dramatically increased in GB-IL mice. The downstream FXR target SHP was slightly increased while the differential expression of Shp2 was not observed across the groups. This pattern of protein expression and the associated decreased FGF15 would be expected with low bile acid availability, in contrast with the increased circulating bile acids observed with GB-IL (FIG. 2).

Adaptations of the Gut Microbiome to Bariatric Procedures.

Figure 8:
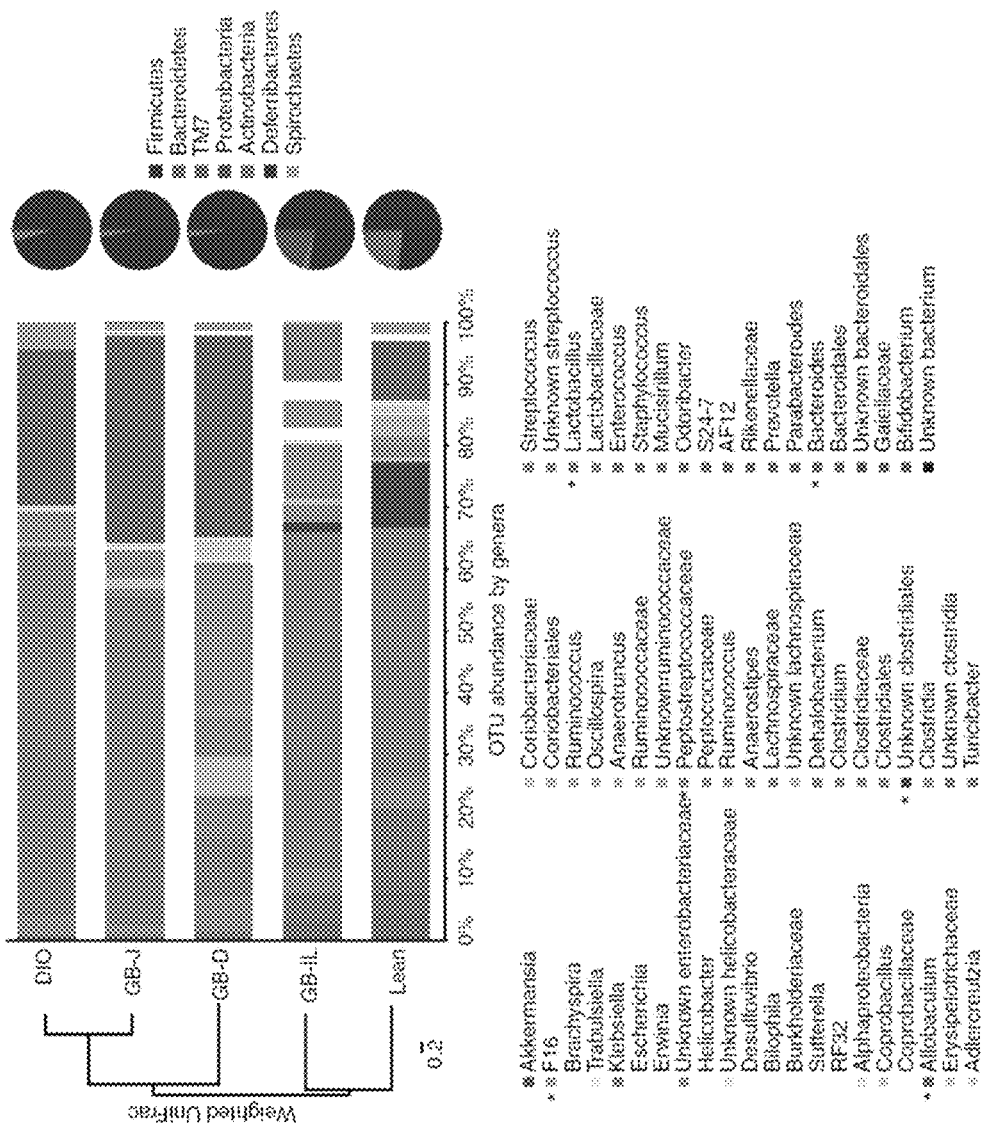
FIG. 8 shows biliary diversion procedures differentially alter the gut microbiome. Caecal contents from DIO, GB-D, GB-J and GB-IL mice 8 weeks after surgery were subjected to 16S rRNA gene sequence analysis. Relative abundance of bacterial genera (bar chart) and phyla (pie chart) with each surgical procedure is shown. The y-axis is a weighted Unifrac analysis of the microbiota for the pooled treatment group. '*' indicates reference points for a given taxa (n of 5 mice per group).
Figure 17A:
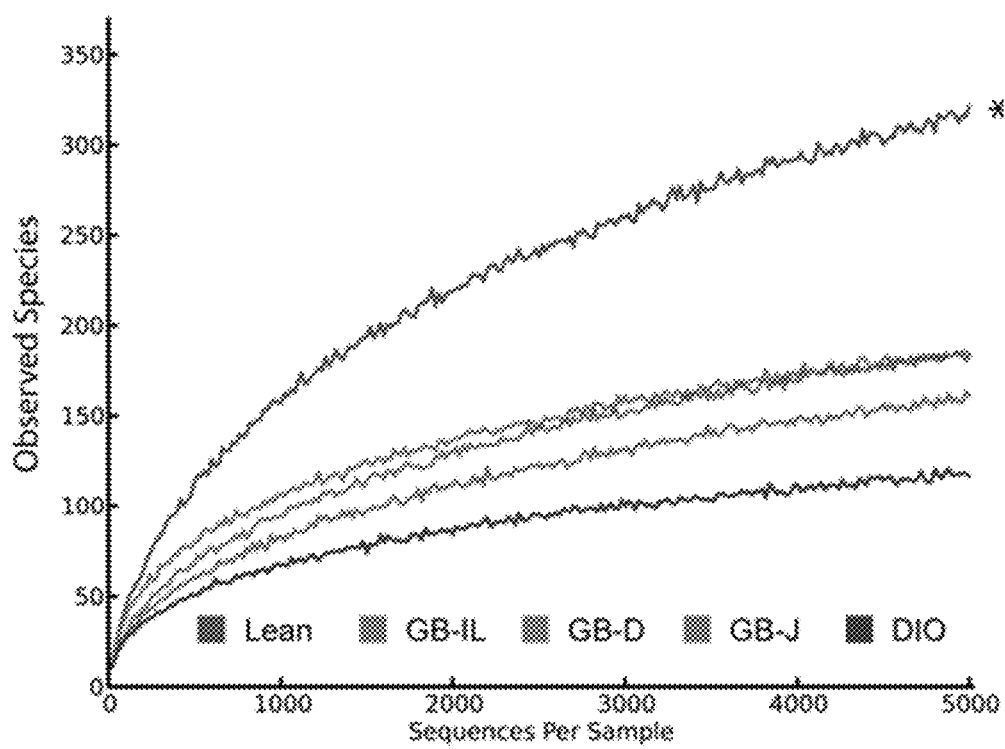
FIGS. 17A to 17C show high fat diet decreases gut microbial diversity. Cecal contents were obtained 8 weeks after surgery. Microbial diversity was analyzed by bacterial tag encoded FLX amplicon pyrosequencing (bTEFAP) using a Roche 454 pyrosequencer and titanium reagents, and 3-5 k nominal sequences per sample of high quality extracted DNA.
Figure 17B:
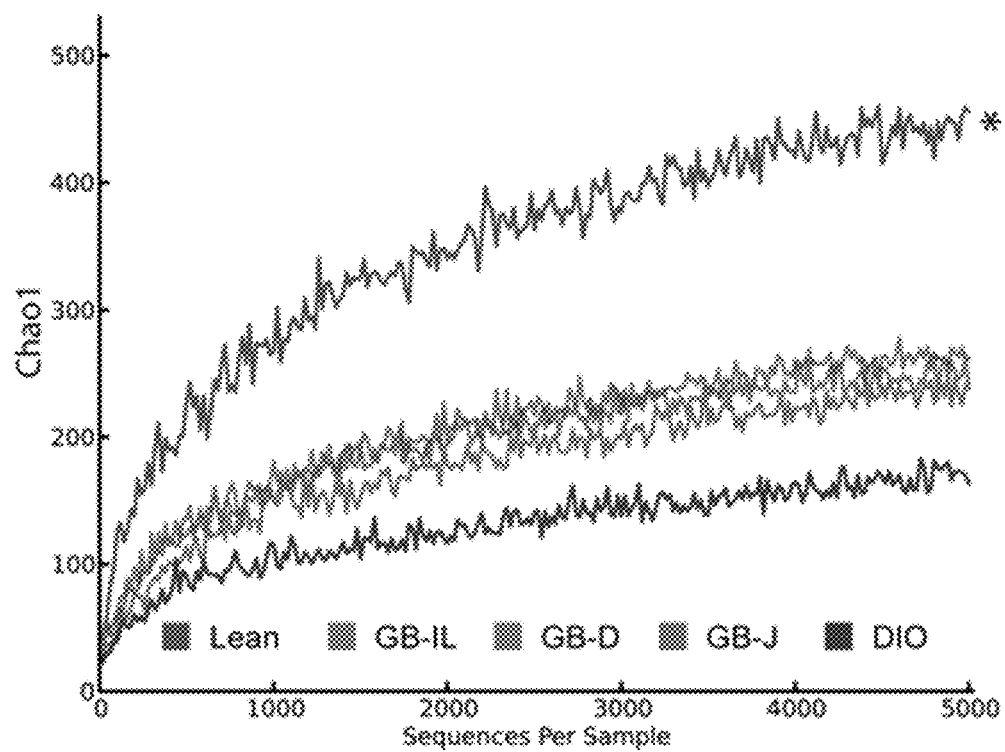
Figure 17C:
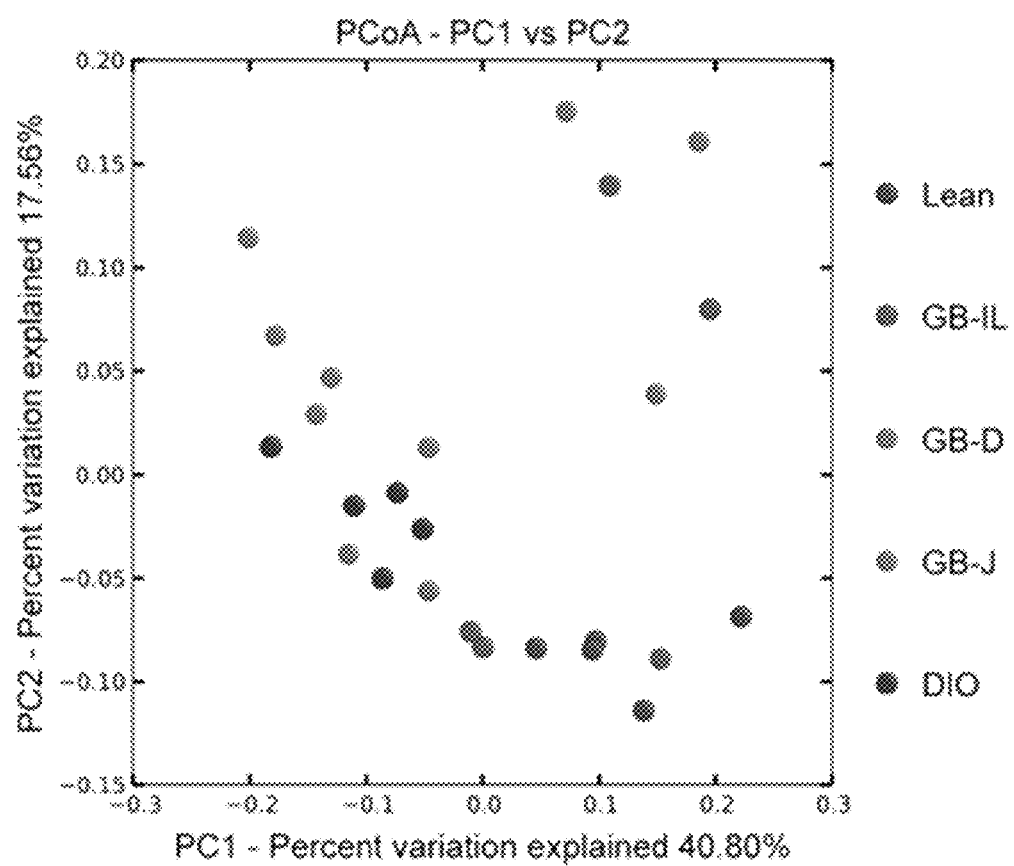

The microbiota influence bile acid metabolism and excretion (Degirolamo, C., et al. Cell Rep. 7, 12-18 (2014)), which raises the question whether the change in microbiota is causing the altered bile acid pool in GB-IL. Next examined was whether significant changes in the microbiota occur with bile diversion and if they might explain some of the observed changes. Caecal contents from mice 8 weeks after the biliary diversion procedures were subjected to pyrosequencing, targeting the V3-V4 region of the 16S ribosomal RNA (rRNA) gene (Turnbaugh, P. J. et al. Nature 487, 47-48 (2012)). FIG. 8 illustrates the breakdown of the bacterial taxonomy at the genera and phyla level. The dominant phylum, Firmicutes, represented 95.5-97.1% of the sequences observed in the DIO, GB-D and GB-J mice, while they only represented 76.0-77.3% of the sequences for the lean and GB-IL mice. The DIO, GB-D and GB-J mice were nearly void of Bacteroidetes, consistent with previous reports that Bacteroidetes bacteria are lower in obese mice and people than in lean controls (Furet, J. P. et al. Diabetes 59, 3049-3057 (2010)). In contrast, GB-IL mice had a significant increase in Bacteroidetes thus decreasing the ratio of Firmicutes/Bacteroidetes in a manner similar to that described for bariatric procedures (Liou, A. P. et al. Sci. Transl. Med. 5, 178ra141 (2013)). DIO, GB-D and GB-J mice had marked increases in the relative abundance of the TM7 phyla that was not present in GB-IL mice. GB-IL also had a significant increase in Proteobacteria relative to other groups. Pairwise analysis of the weighted UniFrac (sensitive to the abundances of taxa) indicates that there was a significant difference between the microbiota of GB-IL and the GB-D or GB-J mice (Table 4). Each surgical procedure resulted in similar levels of microbial diversity (FIG. 17A,B and Table 5) but lean mice had the most diverse microbiome overall ($P<0.05$). The individual mice tended to cluster within the treatment groups, with regard to their weighted beta diversity (FIG. 17C). To further investigate more specific bacterial strains that might be at work, the abundance of *Christensenella minuta* in DIO, bile diverted and RYGB mice caecal DNA was probed by 16 rRNA gene reverse transcription (RT-PCR). This leptogenic bacterial species, recently identified as being strongly associated with the lean phenotype in humans (Goodrich, J. K. et al. Cell 159, 789-799 (2014)), was not detectable in any caecal DNA sample in contrast to *C. minuta* genomic DNA positive controls, therefore these findings relegate this species as minimally relevant to the metabolic improvements observed in this model.

TABLE 4

Weighted Unifrac significance test

| Group | | P value |
|---|---|---|
| DIO | Lean | 0.03 |
| GB-D | GB-IL | 0.05 |
| | GB-J | 0.62 |
| | HFD | 0.39 |
| | Lean | 0.04 |
| GB-J | DIO | 0.87 |
| | Lean | 0.00 |
| GB-IL | GB-J | 0.03 |
| | DIO | 0.06 |
| | Lean | 0.06 |

TABLE 5

OTU table.

| Taxon | Lean | GB-IL | GB-D | GB-J | DIO |
|---|---|---|---|---|---|
| None; Other; Other; Other; Other; Other | 7159 | 7186 | 4041 | 5991 | 6392 |
| k_Bacteria; Other; Other; Other; Other; Other | 2 | 0 | 0 | 1 | 0 |
| k_Bacteria; p_Actinobacteria; c_Actinobacteria; o_Bifidobacteriales; f_Bifidobacteriaceae; g_*Bifidobacterium* | 25 | 103 | 8 | 54 | 38 |
| k_Bacteria; p_Actinobacteria; c_Thermoleophilia; o_Gaiellales; f_Gaiellaceae; g_ | 2 | 0 | 2 | 0 | 0 |
| k_Bacteria; p_Bacteroidetes; c_Bacteroidia; o_Bacteroidales; Other; Other | 4 | 0 | 0 | 0 | 0 |
| k_Bacteria; p_Bacteroidetes; c_Bacteroidia; o_Bacteroidales; f_; g_ | 36 | 0 | 0 | 11 | 0 |
| k_Bacteria; p_Bacteroidetes; c_Bacteroidia; o_Bacteroidales; f_Bacteroidaceae; g_*Bacteroides* | 2329 | 1338 | 7 | 18 | 5 |
| k_Bacteria; p_Bacteroidetes; c_Bacteroidia; o_Bacteroidales; f_Porphyromonadaceae; g_*Parabacteroides* | 250 | 404 | 0 | 26 | 0 |
| k_Bacteria; p_Bacteroidetes; c_Bacteroidia; o_Bacteroidales; f_Prevotellaceae; g_*Prevotella* | 276 | 0 | 0 | 1 | 0 |
| k_Bacteria; p_Bacteroidetes; c_Bacteroidia; o_Bacteroidales; f_Rikenellaceae; g_ | 2607 | 80 | 258 | 125 | 27 |
| k_Bacteria; p_Bacteroidetes; c_Bacteroidia; o_Bacteroidales; f_Rikenellaceae; g_AF12 | 38 | 1 | 0 | 27 | 2 |
| k_Bacteria; p_Bacteroidetes; c_Bacteroidia; o_Bacteroidales; f_S24-7; g_ | 10038 | 117 | 85 | 87 | 5 |
| k_Bacteria; p_Bacteroidetes; c_Bacteroidia; o_Bacteroidales; f_[Odoribacteraceae]; g_*Odoribacter* | 64 | 1 | 6 | 44 | 0 |
| k_Bacteria; p_Deferribacteres; c_Deferribacteres; o_Deferribacterales; f_Deferribacteraceae; g_*Mucispirillum* | 14 | 3 | 1 | 24 | 0 |
| k_Bacteria; p_Firmicutes; c_Bacilli; o_Bacillales; f_Staphylococcaceae; g_*Staphylococcus* | 0 | 7 | 0 | 0 | 0 |
| k_Bacteria; p_Firmicutes; c_Bacilli; o_Lactobacillales; f_Enterococcaceae; g_*Enterococcus* | 185 | 2431 | 301 | 293 | 364 |

TABLE 5-continued

OTU table.

| Taxon | Lean | GB-IL | GB-D | GB-J | DIO |
|---|---|---|---|---|---|
| k__Bacteria; p__Firmicutes; c__Bacilli; o__Lactobacillales; f__Lactobacillaceae; g__ | 4002 | 2366 | 2819 | 955 | 1577 |
| k__Bacteria; p__Firmicutes; c__Bacilli; o__Lactobacillales; f__Lactobacillaceae; g__Lactobacillus | 29938 | 31835 | 4571 | 32303 | 28501 |
| k__Bacteria; p__Firmicutes; c__Bacilli; o__Lactobacillales; f__Streptococcaceae; Other | 4 | 75 | 42 | 6 | 11 |
| k__Bacteria; p__Firmicutes; c__Bacilli; o__Lactobacillales; f__Streptococcaceae; g__Streptococcus | 0 | 2 | 2 | 2 | 0 |
| k__Bacteria; p__Firmicutes; c__Bacilli; o__Turicibacterales; f__Turicibacteraceae; g__Turicibacter | 0 | 3 | 50 | 22 | 440 |
| k__Bacteria; p__Firmicutes; c__Clostridia; Other; Other; Other | 20 | 6 | 25 | 10 | 0 |
| k__Bacteria; p__Firmicutes; c__Clostridia; o__; f__; g__ | 54 | 18 | 5 | 9 | 2 |
| k__Bacteria; p__Firmicutes; c__Clostridia; o__Clostridiales; Other; Other | 7869 | 888 | 1 | 3 | 21 |
| k__Bacteria; p__Firmicutes; c__Clostridia; o__Clostridiales; f__; g__ | 37 | 0 | 7 | 5 | 0 |
| k__Bacteria; p__Firmicutes; c__Clostridia; o__Clostridiales; f__Clostridiaceae; g__ | 96 | 32 | 39 | 21 | 12 |
| k__Bacteria; p__Firmicutes; c__Clostridia; o__Clostridiales; f__Clostridiaceae; g__Clostridium | 0 | 1548 | 3172 | 1019 | 629 |
| k__Bacteria; p__Firmicutes; c__Clostridia; o__Clostridiales; f__Dehalobacteriaceae; g__Dehalobacterium | 48 | 3 | 2 | 1 | 1 |
| k__Bacteria; p__Firmicutes; c__Clostridia; o__Clostridiales; f__Lachnospiraceae; Other | 354 | 578 | 3144 | 990 | 221 |
| k__Bacteria; p__Firmicutes; c__Clostridia; o__Clostridiales; f__Lachnospiraceae; g__ | 1639 | 616 | 3015 | 1391 | 235 |
| k__Bacteria; p__Firmicutes; c__Clostridia; o__Clostridiales; f__Lachnospiraceae; g__Anaerostipes | 36 | 0 | 0 | 0 | 0 |
| k__Bacteria; p__Firmicutes; c__Clostridia; o__Clostridiales; f__Lachnospiraceae; g__[Ruminococcus] | 272 | 128 | 1022 | 13 | 54 |
| k__Bacteria; p__Firmicutes; c__Clostridia; o__Clostridiales; f__Peptococcaceae; g__ | 3 | 0 | 1 | 0 | 0 |
| k__Bacteria; p__Firmicutes; c__Clostridia; o__Clostridiales; f__Peptostreptococcaceae; g__ | 552 | 4394 | 11249 | 1433 | 2100 |
| k__Bacteria; p__Firmicutes; c__Clostridia; o__Clostridiales; f__Ruminococcaceae; Other | 271 | 41 | 42 | 38 | 17 |
| k__Bacteria; p__Firmicutes; c__Clostridia; o__Clostridiales; f__Ruminococcaceae; g__ | 1602 | 12 | 26 | 16 | 143 |
| k__Bacteria; p__Firmicutes; c__Clostridia; o__Clostridiales; f__Ruminococcaceae; g__Anaerotruncus | 7 | 25 | 5 | 0 | 0 |
| k__Bacteria; p__Firmicutes; c__Clostridia; o__Clostridiales; f__Ruminococcaceae; g__Oscillospira | 812 | 89 | 62 | 105 | 18 |
| k__Bacteria; p__Firmicutes; c__Clostridia; o__Clostridiales; f__Ruminococcaceae; g__Ruminococcus | 132 | 6 | 13 | 9 | 0 |
| k__Bacteria; p__Firmicutes; c__Clostridia; o__Coriobacteriales; f__; g__ | 5 | 0 | 0 | 0 | 0 |
| k__Bacteria; p__Firmicutes; c__Clostridia; o__Coriobacteriales; f__Coriobacteriaceae; g__ | 45 | 0 | 0 | 0 | 0 |
| k__Bacteria; p__Firmicutes; c__Clostridia; o__Coriobacteriales; f__Coriobacteriaceae; g__Adlercreutzia | 1475 | 198 | 1895 | 552 | 362 |
| k__Bacteria; p__Firmicutes; c__Erysipelotrichi; o__Erysipelotrichales; f__Erysipelotrichaceae; g__ | 105 | 2 | 4 | 2 | 4 |
| k__Bacteria; p__Firmicutes; c__Erysipelotrichi; o__Erysipelotrichales; f__Erysipelotrichaceae; g__Allobaculum | 7075 | 55 | 16044 | 20682 | 12585 |
| k__Bacteria; p__Firmicutes; c__Erysipelotrichi; o__Erysipelotrichales; f__[Coprobacillaceae]; g__ | 0 | 4 | 0 | 0 | 0 |
| k__Bacteria; p__Firmicutes; c__Erysipelotrichi; o__Erysipelotrichales; f__[Coprobacillaceae]; g__Coprobacillus | 156 | 0 | 0 | 0 | 0 |
| k__Bacteria; p__Proteobacteria; c__Alphaproteobacteria; o__; f__; g__ | 6 | 0 | 0 | 0 | 0 |
| k__Bacteria; p__Proteobacteria; c__Alphaproteobacteria; o__RF32; f__; g__ | 8 | 0 | 0 | 0 | 0 |
| k__Bacteria; p__Proteobacteria; c__Betaproteobacteria; o__Burkholderiales; f__Alcaligenaceae; g__Sutterella | 258 | 10 | 0 | 0 | 0 |
| k__Bacteria; p__Proteobacteria; c__Betaproteobacteria; o__Burkholderiales; f__Burkholderiaceae; g__ | 2 | 0 | 0 | 0 | 0 |
| k__Bacteria; p__Proteobacteria; c__Deltaproteobacteria; o__Desulfovibrionales; f__Desulfovibrionaceae; g__Bilophila | 0 | 0 | 0 | 1 | 1 |
| k__Bacteria; p__Proteobacteria; c__Deltaproteobacteria; o__Desulfovibrionales; f__Desulfovibrionaceae; g__Desulfovibrio | 155 | 25 | 219 | 89 | 31 |
| k__Bacteria; p__Proteobacteria; c__Epsilonproteobacteria; o__Campylobacterales; f__Helicobacteraceae; Other | 38 | 2 | 0 | 0 | 0 |
| k__Bacteria; p__Proteobacteria; c__Epsilonproteobacteria; o__Campylobacterales; f__Helicobacteraceae; g__Helicobacter | 377 | 1143 | 0 | 23 | 2 |
| k__Bacteria; p__Proteobacteria; c__Gammaproteobacteria; o__Enterobacteriales; f__Enterobacteriaceae; Other | 0 | 2611 | 26 | 233 | 0 |
| k__Bacteria; p__Proteobacteria; c__Gammaproteobacteria; o__Enterobacteriales; f__Enterobacteriaceae; g__Erwinia | 0 | 0 | 0 | 2 | 0 |
| k__Bacteria; p__Proteobacteria; c__Gammaproteobacteria; o__Enterobacteriales; f__Enterobacteriaceae; g__Escherichia | 0 | 1784 | 46 | 107 | 0 |
| k__Bacteria; p__Proteobacteria; c__Gammaproteobacteria; o__Enterobacteriales; f__Enterobacteriaceae; g__Klebsiella | 0 | 5507 | 0 | 0 | 0 |
| k__Bacteria; p__Proteobacteria; c__Gammaproteobacteria; o__Enterobacteriales; f__Enterobacteriaceae; g__Trabulsiella | 0 | 113 | 1 | 0 | 0 |
| k__Bacteria; p__Spirochaetes; c__[Brachyspirae]; o__[Brachyspirales]; f__Brachyspiraceae; g__Brachyspira | 5 | 0 | 0 | 0 | 0 |
| k__Bacteria; p__TM7; c__TM7-3; o__CW040; f__F16; g__ | 1333 | 0 | 726 | 851 | 2108 |
| k__Bacteria; p__Verrucomicrobia; c__Verrucomicrobiae; o__Verrucomicrobiales; f__Verrucomicrobiaceae; g__Akkermansia | 0 | 32 | 0 | 19 | 0 |

Methods

Mice and Operations.

All experiments and surgical preparations were performed according to protocols approved by the Vanderbilt University Medical Center Institutional Animal Care and Use Committee (IACUC). The mice remained under the care of the Division of Animal Care (DAC) at Vanderbilt University in compliance with NIH guidelines and the Principles of Laboratory Animal Care, and the Guide for the Care and Use of Laboratory Animals. Male C57BL/6 mice were housed at 23° C. on a 0700-1900-hour light cycle and were fed a HFD (60% kcal from fat; Bio-Serv, Frenchtown, N.J.), starting at 6 weeks of age for 12 weeks prior to being randomly allocated to a surgical group. Biliary diversion was performed under isoflurane anaesthesia using a 12-15× microsurgical scope. In the biliary diversion operation, a side-to-side, running-continuous, GB to small bowel anastomosis was created on the anti-mesenteric surface of the small bowel using 9-0 nylon suture. The anastomosis was created on the undersurface of the GB, away from the fundus and from the delicate vasculature supplying the GB. The length of the anastomosis was approximately 2-3 mm. Bile flow was diverted from the GB to either the duodenum (via a GB-D at the level of the ampulla of Vater, labelled) or the jejunum (via a GB-J, 4 cm distal to the ligament of Treitz) or the ileum (via GB-IL, 4 cm proximal to the ileo-caecal valve). The GB-D model was nearly identical to the natural physiologic bile flow and does not change pancreatic flow; hence the GB-D is considered the sham procedure. RYGB was performed as reported (Furet, J. P. et al. Diabetes 59, 3049-3057 (2010)). The common bile duct was ligated using 9-0 nylon as far proximal to the pancreatic duct as possible as not to alter pancreatic secretory flow. Abdominal fascia and skin were closed using simple, interrupted sutures of 5-0 polyglactin and 6-0 polypropylene sutures, respectively. Mice were maintained on the HFD and water ad libitum after surgery up to the endpoint measurements. Early surgical mortality (<1 week post-operatively) was approximately 15%, being almost entirely due to leakage of the GB-to-bowel anastomosis regardless of its location. In earlier studies this rate was higher (approximately 50%), though as the surgeons became more experienced with the GB-to-bowel anastomosis (>6-9 months of experience) this improved greatly. Surgical success rate, defined as mouse survival for 41 week without surgical complications, was 80% for GB-D, 85% for GB-J, 90% for GB-IL and 75% for RYGB. Surgical complications included obstruction at the site of the GB anastomosis to the jejunum or ileum (<5%) and occurred within 1-4 weeks post-surgery. 40% of mice subjected to RYGB mice and 80% of those that undergo BPD have a reduced haematocrit (Furet, J. P. et al. Diabetes 59, 3049-3057 (2010)). GB-intestinal anastomosis was not associated with anaemia, as previously reported for RYGB (Yin, D. P. et al. Ann. Surg. 254, 73-82 (2011)).

Whole-Body Tissue Composition.

Body mass was measured weekly for 8 weeks using mq10 NMR analyzer (Bruker Optics Inc., Billerica, Mass.) following 2 h of fasting (Furet, J. P. et al. Diabetes 59, 3049-3057 (2010)). Fat and muscle mass were calculated in grams.

Intraperitoneal Glucose Tolerance Tests (IPGTT).

Mice were fasted for 4 h prior to IPGTT at 2, 4 or 8 weeks after surgery. Blood was sampled from the tail vein before and 10, 20, 30, 45, 60, 75, 90 and 120 min after an intraperitoneal injection of dextrose (20%) at 2.0 mg g$^{-1}$ body weight. Blood glucose levels (mg dl$^{-1}$) were measured using a blood glucose meter (SureStep, LifeScan, Inc.).

Indirect Calorimetry.

EE was assessed by indirect calorimetry using a system comprised of 16 identical, yet separate, metabolic cages equipped for the continual monitoring of ambulatory activity and ad libitum access to HFD and water (Promethion, Sable Systems, Las Vegas, Nev.). Oxygen ($O_2$), carbon dioxide ($CO_2$) and water vapor levels were constantly monitored while temperature and humidity levels were tightly regulated (GA3, Sable Systems). The in current air flow rate was set at 3000 ml min$^{-1}$ (FR8, Sable Systems). $CO_2$ consumption and $O_2$ production were measured for each mouse at 10-min intervals for 1 min. Respiratory quotients were calculated as the ratio of $CO_2$ production over $O_2$ consumption. EE is calculated using the Weir equation (1):

$$Kcal\ h^{-1} = 60 \times (0.003941 \times WO_2 + 0.001106 \times VCO_2)$$

Data acquisition and instrument control were coordinated by MetaScreen v. 2.2.18 and the obtained raw data was processed using ExpeData v. 1.7.30 (Sable Systems) using an analysis script detailing all aspects of data transformation (Weir, J. B. J. Physiol. 109, 1-9 (1949)). The script is available on request from the corresponding author. Data was analysed by ANCOVA using scripts available at the National Mouse Metabolic Phenotyping Centers (MMPC, Nashville, Tenn., USA) Energy Expenditure Analysis Page (www.mmpc.org/shared/regression.aspx; accessed March 2015). Such methods consider EE differences when adjusting for differences in body mass/composition.

Chemicals.

CA (5β-cholanic acid-3α,7α,12α-triol), α-MCA (5β-cholanic acid-3α,6β,7α-triol), β-MCA (5β-cholanic acid-3α,6β,7β-triol), chenodeoxycholic acid (5β-cholanic acid-3α,7α-diol, CDCA), deoxycholic acid (5β-cholanic acid-3α,12α-diol, DCA), hyodeoxycholic acid (5β-cholanic acid-3α,6α-diol, HDCA), ursodeoxycholic acid (5β-cholanic acid-3α,7β-diol, UDCA), taurocholic acid (5β-cholanic acid-3α,7α,12α-triol-N-[2-sulphoethyl]-amide, TCA), tauro-α-MCA (5β-cholanic acid-3α, 6β3,7α-triol-N-[2-sulphoethyl]-amide), TbMCA (5β-cholanic acid-3α,6β,7β-triol-N-[2-sulphoethyl]-amide), ToMCA (5β-cholanic acid-3α,6α,7β-triol-N-[2-sulphoethyl]-amide), taurochenodeoxycholic acid (5β-cholanic acid-3α,7α-diol-N-[2-sulphoethyl]-amide, TCDCA), taurodeoxycholic acid (5β-cholanic acid-3α, 12α-diol-N-[2-sulphoethyl]-amide, TDCA), taurohyodeoxycholic acid (5β-cholanic acid-3α, 6α-diol-N-[2-sulphoethyl]-amidel, THDCA), and taurolithocholic acid (5β-cholanic acid-3α-ol-N-[2-sulphoethyl]-amide, TLCA) were purchased from Steraloids, Inc. (Newport, R.I.). Cholic-2,2,4,4-d4 acid (5β-cholanic acid-3α,7α,12α-triol-2,2,4,4-d4, d4-CA), taurocholic-2,2,4,4-d4 acid (5β-cholanic acid-3α,7α,12α-triol-N-[2-sulphoethyl]-amide, TCA-d4), chenodeoxycholic-2,2,4,4-d4 acid (5β-cholanic acid-3α,7α-diol-2,2,4,4-d4, CDCA-d4); glycocholic-2,2,4,4-d4, (5β-cholanic acid-3α,7α,12α-triol-N-[2carboxymethyl]-amide-2,2,4,4-d4, GCA-d4), glycochenodeoxycholic-2,2,4,4-d4 acid (5β-cholanic acid-3α,7α-diol-N-[carboxymethyl]-amide-2,2,4,4-d4, GCDCA-d4) were purchased from C.D.N. Isotopes Inc. (Pointe Claire, Montreal, PQ, CA). TbMCA (5β-cholanic acid-3α, 6β,7β-triol-N-[2-sulphoethyl]-amide-2,2,4,4-d4, TbMCA-d4), was purchased from United States Biological Corp., Swampscott, Mass.). HPLC grade water, acetonitrile, ethanol, methanol, ammonium acetate and ammonia were purchased from Sigma Chemicals (St. Louis, Mo.). Formic acid was purchased from Thermo Scientific (Rockford, Ill.).

Calibrators and Controls.

Stock solutions of 2.5 mmol $l^{-1}$ of all bile acids (THCA, HCA, TαMCA, TβMCA, TωMCA, HDCA, THDCA: 10 µmol $l^{-1}$) were used to prepare calibrators with concentrations of 100 µmol $l^{-1}$ in methanol. For the preparation of calibrators, bile acids were mixed to achieve final concentrations of 20, 2.5, 0.75, 0.25, 0.05, 0.015 and 0.005 µmol $l^{-1}$. To prepare 20 ml of a 2.0 nmol $l^{-1}$ internal standard, 250 µl each of d4-CDCA, d4-TCA, d4-GCDCA and 500 µl d4-CA, d4-TrβMCA and d4-GCA were added to 20% (v/v) acetonitrile.

Sample Preparation for UPLC/ESI-MS.

To 50 µl of plasma were added 200 µl of 100 mM aqueous sodium hydroxide and 50 µl of internal standard. The sample was heated at 64° C. for 30 min, centrifuged for 10 min at 14,400 g and the supernatant acidified to pH 7.0 with 50 µl of 0.1M hydrochloric acid. The sample was brought to a final volume of 1 ml with water and applied to a 1 cc (30 mg) Oasis HLB cartridge (Waters, Milford, Mass.) previously equilibrated first with 1 ml of methanol, then 1 ml of water (Rodrigues, 1996). The column-bound bile acids were washed with 1 ml of 5% (v/v) aqueous methanol then 1ml of 2% (v/v) aqueous formic acid. Bile acids were eluted from the column with 1 ml of 2% (v/v) ammonia in methanol and the eluent evaporated to dryness using a rotary evaporator at 30° C. for 2 h. Samples were resuspended in 100 µl of 25% (v/v) acetonitrile in water.

Liquid Chromatography.

An Acquity ultra performance liquid chromatography system (UPLC; Waters) employing a Luna C18(2) 50×2.0 mm, 3 mm column, C18 4×2.0 mm pre-column, both from Phenomenex (Torrance, Calif.), was heated to 50° C., and a binary solvent system of 20% (v/v) acetonitrile in water (mobile phase A) and 80% (v/v) acetonitrile in water (mobile phase B) both containing 1 mM ammonium acetate were used to resolve plasma bile acids. The injection volume onto the column was 15 µl. The flow rate was 400 µl $min^{-1}$ into the mass spectrometry (MS). Chromatography was similar to a published method and started with a solvent mixture of 95% A that decreased to 85% A at 15 min, to 75% at 20 min, then to 25% at 22 min where after it increased to 95% A at 24 min for 3 min (Hagio, M., et al. J. Lipid Res. 50, 173-180 (2009)).

Mass Spectrometry.

MS analysis was performed using a TSQ Quantum mass spectrometer (ThermoFinnigan, Sunnydale, Calif.) equipped with an ESI probe in negative-ion mode. Quantitation was done in a multiple reaction monitoring mode with collision energy of 10 V. The following (optimized) parameters were used for the detection of the analytes and the internal standard; N2 sheath gas, 49 p.s.i.; N2 auxiliary gas, 25 p.s.i.; spray voltage, 3.0 kV; source CID, 25 V; capillary temperature, 300° C.; capillary offset, −35 V; tube lens voltage, 160 V; Q2 gas pressure, 1.5 mtor; Q3 scan width 1 m/z; Q1/Q3 peak widths at half-maximum, 0.7 m/z. Calibration curves and concentration of individual bile acids were calculated by LCQuan 2.5.5 software (ThermoFinnigan). Concentrations of individual bile acids were calculated from peak area in the chromatogram detected with SRM relative to the appropriate internal standard. The composition and amount of bile acids in serum are reported in Tables 1 and 2 and FIGS. 14 and 15.

Liver Tissue Macroarray Assembly and Immunohistochemistry.

For assessments of steatosis, Image J was used to quantify the amount of steatosis in 5-6 liver images for each surgical group and control. Tissue microarray (TMA) construction and biomarker staining was performed by the Vanderbilt Translational Pathology Shared Resource. One millimeter cores were sampled, in duplicate, from each of 70 liver specimens donor blocks using TMA Grand Master Tissue Microarrayer (Perkin Elmer, Waltham, Mass.) and randomly arranged on the TMA. Liver micrograph images were captured using a high throughput Leica SCN400 Slide Scanner automated digital image system from Leica Microsystems (Buffalo Grove, Ill.). Whole slides were imaged at ×20 magnification to a resolution of 0.5 µm per pixel. Tissue cores were mapped using Ariol Review software. The numbers of positive (brown) and negative (blue) nuclei were determined by analysis of the high-resolution images in the Ariol software. Immunostained TMA slides were imaged on a Leica SCN400 Slide Scanner (Leica Biosystems). Tissue cores were imaged at ×20 magnification to a resolution of 0.5 µm per pixel. Cells were identified utilizing standard Ariol analysis scripts (Leica). Upper and lower thresholds for colour, saturation, intensity, size, roundness and axis length were set for both blue haematoxylin staining of nuclei and for brown DAB reaction products (anti-mouse F4/80, ab6640, Abcam, Cambridge, Mass.). Thus, brown (DAB) positive cells can be distinguished from blue (haematoxylin only) negative cells. The area of positive staining per core was calculated as a percent of the total analysed area divided by area of brown (DAB positive) pixels.

RNA Sequencing, Data Processing and Analysis.

The transcriptional sequencing was implemented with modifications of the standard Illumina methods (Bentley, D. R. et al. Nature 456, 53-59 (2008)). Sequencing reactions were performed using the Illumina HiSeq (v3 chemistry). Initial QC quantification of the extracted total RNA was done by using Qubit Fluorometer (Invitrogen). Agilent 2100 Bioanalyzer was used to check the quality of the extracted RNA from both the samples. About 30 ng of total RNA was amplified using the NuGEN Technologies Ovation RNA amplification kit optimized for RNA sequencing. The output is double-stranded complementary DNA (cDNA) that was sheared using the Covaris instrument to an average insert size of 300 bp. The sheared DNA entered the standard Illumina TruSeq library preparation protocol at the standard end-repair step. Following end polishing, a single 'A'-base was added to the 30-end of the DNA fragments. This prepared the DNA fragments for ligation to specialized adaptors that have a 'T'-base overhang at their 30-ends. The Illumina protocol relies on the ligation of the TruSeq adaptor sequences to each end of the DNA molecules to facilitate ligation-mediated PCR (LM-PCR) amplification of the resulting material. The end-repaired DNA with a single 'A'-base overhang was ligated to the adaptors in a standard ligation reaction using T4 DNA ligase and 2-4 µM final adaptor concentration, depending on the DNA yield following purification after the addition of the 'A'-base (a 10-fold molar excess of adaptors was used in each reaction). Following ligation, the samples were purified and amplified with 12 cycles of LM-PCR to amplify the ligated material in preparation for cluster generation. Following LM-PCR, the samples were purified and assessed for quality using the Agilent Bioanalyzer. Final quantitation was performed using the KAPA Biosystems Kapa Library Quant kit. Based on the RT-PCR data, final 10 nM library dilutions were generated and sequenced at a cluster density of 950,000 clusters·per $mm^2$.

Multiple stages of quality control (QC) on sequencing data was carried out. Raw data and alignment QC were performed using QC3 (Guo, Y. et al. Genomics 103, 323-328 (2014)), and expression analyses were carried out using MultiRankSeq (Guo, Y., et al. Biomed. Res. Int. 2014, 248090 (2014)). All data passed QC. Raw data were aligned with TopHat 2 against mouse MM10 genome, and read count data were obtained using HTSeq, DESeq (Anders, S. & Huber, W. Genome Biol. 11, R106 (2010)), edgeR (Robinson, M. D., et al. Bioinformatics 26, 139-140 (2010)) and baySeq (Hardcastle, T. J. & Kelly, K. A. BMC Bioinformatics 11, 422 (2010)). All software are available on request. False discovery rate <0.05 was used to correct for multiple testing. The resulting ranked canonical pathways (as shown in FIG. 3) were subjected to gene associated feature enrichment analysis using Ingenuity Pathway Analysis.

Euglycemic-Hyperinsulinemic Clamps.

Insulin sensitivity assessments were conducted on DIO, GB-IL and RYGB mice (n of 4-5) at 4 weeks post-operative by the Vanderbilt MMPC. Mice were provided diets and water ad libitum and housed at standard room temperature of (23° C.) on a 12 h light cycle. One week before the clamp procedure, catheters were surgically placed in the carotid artery and jugular vein for sampling and infusions, respectively. Mice were withheld food for 5 h prior to the clamp procedure. Erythrocytes were replaced to prevent a decline in haematocrit that occurs with repeated blood sampling. A primed (1.5 µCi) continuous (0.075 µCi min$^{-1}$) [3-$^3$H] glucose infusion was started at −20 min. The clamp was initiated at 0 min with a continuous insulin infusion (2.5 mUkg$^{-1}$ min$^{-1}$) that was maintained for 145 min. Arterial glucose was measured at 10 min intervals to provide feedback to adjust the glucose infusion rate as needed to clamp glucose concentration.

Lipid Analyses.

Sera were collected from untreated lean, DIO, biliary diverted and RYGB mice after 4 h fasting and stored at −80° C. Feces were collected over a 24-h period. Feces (100 mg) was extracted 3:1 with chloroform:methanol, and the resulting lipid extract evaporated to dryness and weighed. FFAs were analyzed by the NEFAs analysis kit (Wako Life Sciences, Richmond Va.). Serum TG and cholesterol were analyzed using Infinity reagents (Thermo Scientific, Middletown, Va.).

Immunoblot Analyses.

The liver and distal ileum was collected at 8 weeks post surgery, homogenized in lysis buffer and pelleted. Protein concentrations of the supernatant were analyzed, and equivalent amounts of protein were loaded onto a polyacrylamide gel. Primary antibodies raised against TGR5 (ab72608; 1:1,000), CYP7A1 (ab65596, 1:1,000) were purchased from Abcam (Cambridge, Mass.). Goat anti-FXR (sc-1204; 1:1,000), rabbit anti-OATPb (sc-135099; 1:500), was from Santa Cruz Biotechnology (Santa Cruz, Calif.). Sheep anti-FGF15 (1:1,000) was purchased from R&D Systems (Minneapolis, Minn.). Rabbit anti-SHP2 was a gift from Dr Gen-Sheng Feng, the University of California San Diego, Calif. The primary antibodies were diluted in Li-Cor blocking buffer and incubated at room temperature for 1 h. Goat anti-rabbit, donkey anti-goat, goat anti-mouse or donkey anti-sheep fluorescently labelled secondary antibodies (Li-Cor Inc., Lincoln, Nebr.) were diluted 1:10,000 and incubated in blocking buffer at room temperature for 1 h with shaking. After three rinses with PBS solution, the membrane was scanned with the Odyssey Infrared Imaging System (Li-Cor Inc.).

Cecal Content Sampling and Microbiota Analysis.

Cecal content samples were collected 8 weeks after surgery and stored at −80° C. when mice were killed. The DNA extractions, amplification, library prep and sequencing were done by the Gut Microbiome Core, at the University of California at Davis. The 16S universal Eubacteria primers (PCR primers 515/806) were used to amplify the V4 variable region. A single-step 30 cycle PCR using HotStarTaq Plus Master Mix Kit (Qiagen, Valencia, Calif.) was used under the following conditions: 94° C. for 3 min, followed by 28 cycles of 94° C. for 30 s; 53° C. for 40 s and 72° C. for 1 min; after which a final elongation step at 72° C. for 5 min was performed. Following PCR, all amplicon products from different samples were mixed in equal concentrations and purified using Agencourt Ampure beads (Agencourt Bioscience Corporation, Mass., USA). Microbial sequencing was analyzed by bacterial tag encoded FLX amplicon pyrosequencing (bTEFAP) using a Roche 454 pyrosequencer and titanium reagents and 3-5K nominal sequences per sample of high quality extracted DNA.

Sequences were depleted of barcodes and primers then short sequences <200 bp are removed, sequences with 41 ambiguous base calls removed and sequences with homopolymer runs exceeding 6 bp removed using the statistical software package Quantitative Insights Into Microbial Ecology (QIIME). A total number of 491,009 sequences passed a quality filter with a minimum score of 25 and an average length of 460 bp. Operational taxonomic units were defined after removal of chimeric and singleton sequences, clustering at 3% divergence (97% similarity) (Dowd, S. E., et al. Foodborne Pathog. Dis. 5, 459-472 (2008)). Operational taxonomic units were then taxonomically classified using BLASTn against a curated GreenGenes database.

For RT-PCR analyses, DNA was extracted from 50 mg of cecal contents on a QIAsymphony (Qiagen 9001297) following Qiagen guidelines using the Complex_200_V6_DSP protocol and the FIX labware. The optional lysozyme pretreatment was performed for each sample. For each fecal sample, 280 µl of Buffer ATL (Qiagen 939011) and 20 µl 10× Lysozyme (Sigma-Aldrich, St Louise, Mo.) was added. The samples were vortexed quick spin and then incubated at 37° C. for 30 min. After incubation, samples were spun briefly to remove condensation from the caps and 300 µl was transferred to 2.0 ml tube (Sarstedt 72.694). Default internal controls were used during the extraction, provided in QIAsymphony DSP Virus/Pathogen Mini Kit (Qiagen 937036). Samples were then eluted to 110 ml AVE. The absolute abundance of *C. minuta* was determined by 16S rRNA gene (Genbank Accession number AB490809) RT-PCR using genomic *C. minuta* (YIT 12065; DSMZ No. 22607, Leibniz-Institut DSMZ-Deutsche Sammlung von Mikroorganismen und Zellkulturen GmbH, Braunschweig, Germany) and primers in Table 6.

TABLE 6

Oligonucleotides used for quantitative RT-PCR.

| Target | Forward Primer | Reverse Primer |
|---|---|---|
| BACS | ACC CTG GAT CAG CTC CTG GAT (SEQ ID NO: 1) | GTT CTC AGC TAG CAG CTT GG (SEQ ID NO: 2) |
| BAT | GGA AAC CTG TTA GTT CTC AGG C (SEQ ID NO: 3) | GTG GAC CCC CAT ATA GTC TCC (SEQ ID NO: 4) |
| BSEP | CTG CCA AGG ATG CTA ATG CA (SEQ ID NO: 5) | CGA TGG CTA CCC TTT GCT TCT (SEQ ID NO: 6) |
| IBAT | ACC ACT TGC TCC ACA CTG CTT (SEQ ID NO: 7) | CGT TCC TGA GTC AAC CCA CAT (SEQ ID NO: 8) |

TABLE 6 -continued

Oligonucleotides used for quantitative RT-PCR.

| Target | Forward Primer | Reverse Primer |
|---|---|---|
| MRP3 | TCC CAC TTT TCG GAG ACA GTA AC (SEQ ID NO: 9) | ACT GAG GAC CTT GAA GTC TTG GA (SEQ ID NO: 10) |
| NTCP | ATG ACC ACC TGC TCC AGC TT (SEQ ID NO: 11) | GCC TTT GTA GGG CAC CTT GT (SEQ ID NO: 12) |
| OATP1 | CAG TCT TAC GAG TGT GCT CCA GAT (SEQ ID NO: 13) | ATG AGG AAT ACT GCC TCT GAA GTG (SEQ ID NO: 14) |
| OSTα | TGT TCC AGG TGC TTG TCA TCC (SEQ ID NO: 15) | CCA CTG TTA GCC AAG ATG GAG AA (SEQ ID NO: 16) |
| OSTβ | GAT GCG GCT CCT TGG AAT TA (SEQ ID NO: 17) | GGA GGA ACA TGC TTG TCA TGA C (SEQ ID NO: 18) |
| IBABP | CAG GAG ACG TGA TTG AAA GGG (SEQ ID NO: 19) | GCC CCC AGA GTA AGA CTG GG (SEQ ID NO: 20) |
| A. muciniphila | CAG CAC GTG AAG GTG GGG AC (SEQ ID NO: 21) | CAG CAC GTG AAG GTG GGG AC (SEQ ID NO: 22) |
| C. minuta | TTC GGG AGG AAC TGT GGG TAT (SEQ ID NO: 23) | GGT TGC TCA CGC GTT ACT CA (SEQ ID NO: 24) |

Real-Time PCR.

The liver and ileal samples obtained at 8 weeks post surgery and were subjected to total RNA extraction using Trizol reagent (Invitrogen). After RNA quantification, 2 μg of total RNA was digested with RNase-free DNase I (Roche Diagnostics, Indianapolis, Ind.), followed by reverse transcription using the High Capacity cDNA Reverse Transcription Kit (Applied Biosystems, Foster City, Calif.). Relative levels of amplicants were determined using SYBR Green qPCR Supermix (Invitrogen) on a Fast 7900HT Real-Time PCR System (Applied Biosystems) with Integrated DNA Technologies (Coralville, Iowa) primer pairs in Table 6. Standard curves for each target were generated and the efficiency of quantitative RT-PCR for each gene was calculated. All data were normalized to the house-keeping gene, 18S, and a comparative threshold cycle (Ct) method, $2^{-\Delta\Delta Ct}$, was used to compare the relative expression levels.

Statistics.

Sample size for this study was based on a prior sample size calculation guided by the outcome variable of weight loss achieved 4 weeks after RYGB was previously reported (Dekaney, C. M. et al. Surgery 144, 174-181 (2008)). This calculation indicated that, if using a repeated-measures model, a minimum of eight mice per treatment group was needed to detect statistical significance between groups. All data are expressed as mean±s.e.m. Unless otherwise indicated, one-way analysis of variance with Dunn's post-test was used to compare three or more groups while Student's t-test (unpaired, two tailed) was used for binary comparisons. All statistical analyses were performed using Prism version 5.0 d software (GraphPad, La Jolla, Calif.). Differences in microbiota richness were tested by analysis of variance. The threshold of statistical significance was set at $P<0.05$.

Figure 18D:
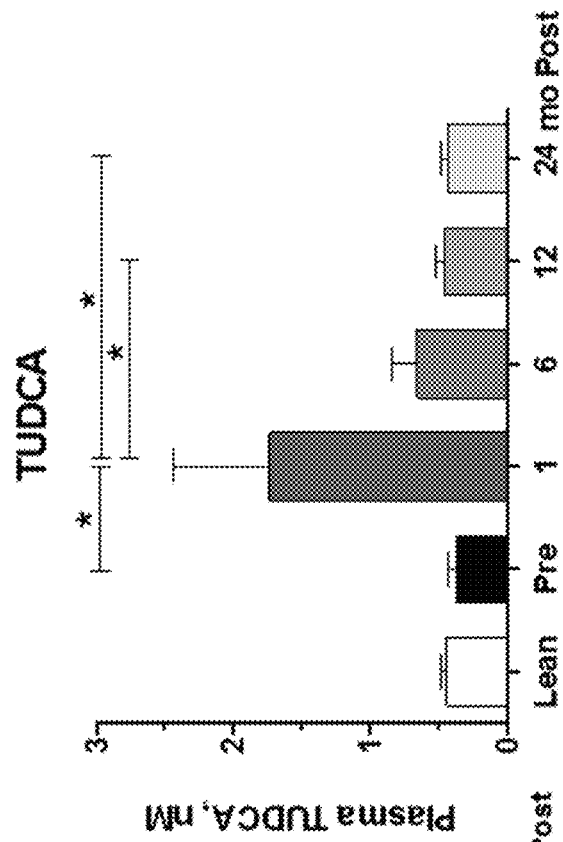
Figure 18C:
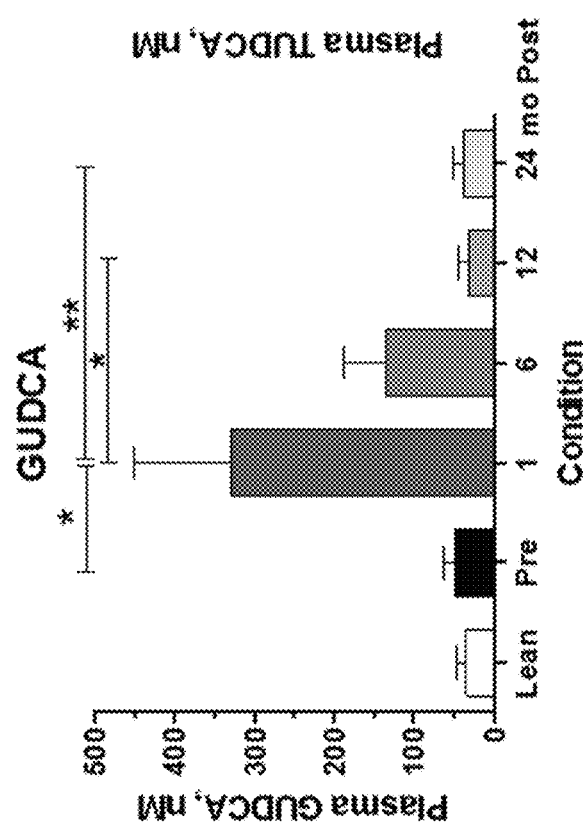

Example 2: Early Increases in Plasma Bile Acids Post Roux-en-Y Gastric Bypass are Driven by Insulin Sensitizing, Secondary Bile Acids Results A brief overview of the selected patient cohort (n=21) from this clinical study can be found in Table 7. All patients underwent RYGB with approximately half (9/21) of the patients having a diagnosis of type 2 diabetes at the time of surgery and approximately half (12/21) were non-diabetic, obese subjects. Using mixed-effects modeling to compare the changes in fasting plasma bile acid concentrations over time, total bile acid concentration (FIG. 18A) exhibited a biphasic rise, being significantly elevated at one month ($P<0.05$) and 24 months ($P<0.01$) postoperatively when compared to preoperative levels. Of the entire bile acid complement quantified, this increase was due to significant increases in only three bile acids at one month, ursodeoxycholic acid (UDCA), glycoursodeoxycholic acid (GUDCA), and tauroursodeoxycholic acid (TUDCA). UDCA is a secondary bile acid and stereoisomer of chenodeoxycholic acid (CDCA), which results from microbial isomerization of CDCA in the gastrointestinal tract. UDCA concentration (FIG. 18B) at one month was significantly different than every other time point and returned to near-baseline concentration by six months. GUDCA and TUDCA are the glycine- and taurine-conjugated forms of UDCA, respectively, that result from gastrointestinal reabsorption of UDCA via the enterohepatic circulation and subsequent hepatic conjugation. Similar to UDCA, GUDCA/TUDCA concentrations were also elevated at one month (FIG. 18C) and then trended down to baseline values by 12 months. No significant differences in GUDCA or TUDCA were detected between one and six months or between six or 12 months. As UDCA and its conjugates are non-12-alpha-hydroxylated bile acids, their significant increases at one month were associated with a trend for a decrease in the 12-alpha/non-12-alpha ratio, though this was not significantly different. No other bile acids concentrations were significantly changed at one month.

Figure 19B:
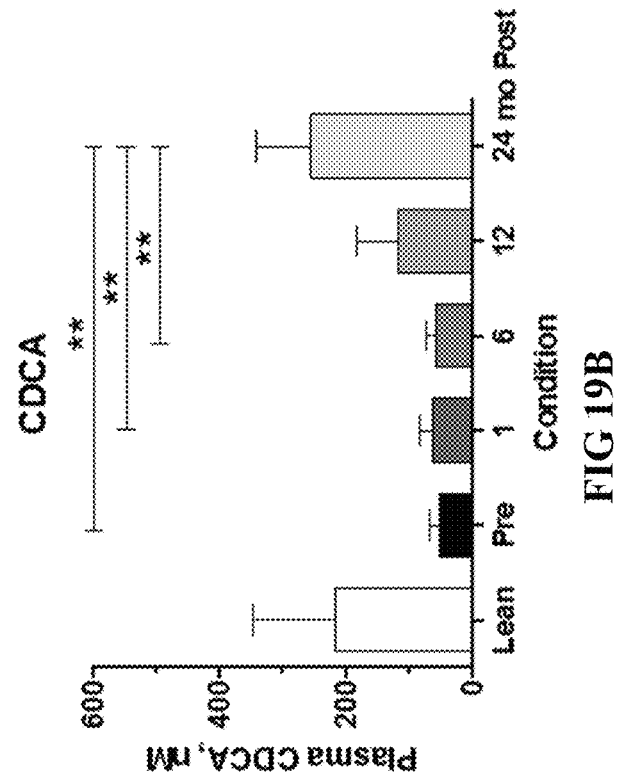
FIGS. 19A to 19E show plasma concentrations of selected primary and secondary bile acid concentrations preoperatively and following RYGB. Serial plasma samples were collected for bile acid measurements preoperatively and at 1, 6, 12 and 24 months postoperatively. Cholic acid (FIG. 19A) and Chenodeoxycholic acid (FIG. 19B) have increases observed at 24 months, while DCA (FIG. 19C) and its glyco-conjugate GDCA (FIG. 19D) have gradual increases at 24 months and 12 months compared to preoperative levels, respectively.
Figure 19A:
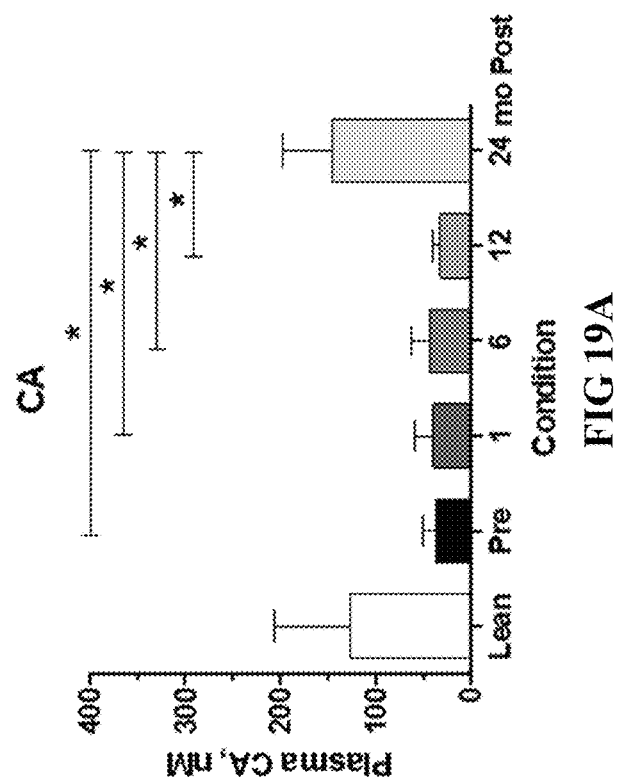
Figure 19D:
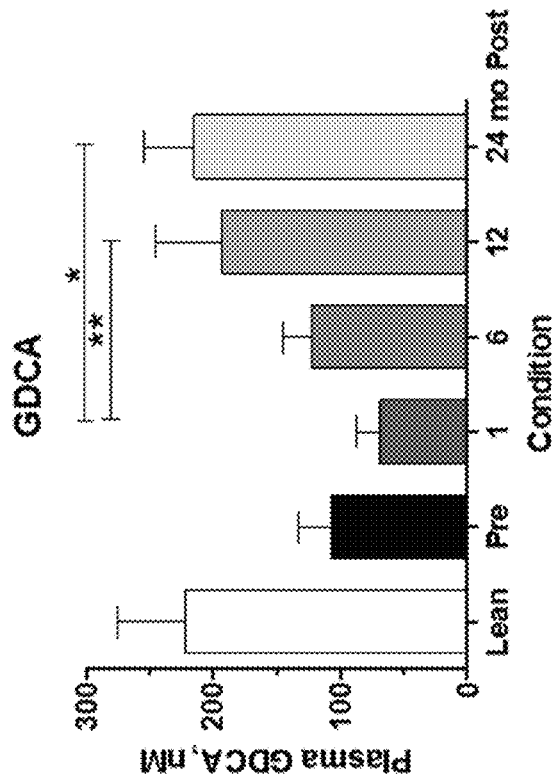
Figure 19C:
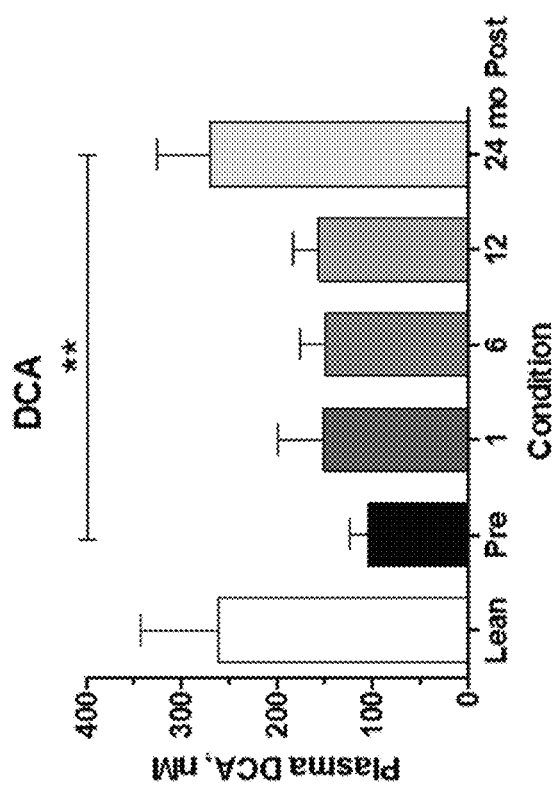
Figure 19E:
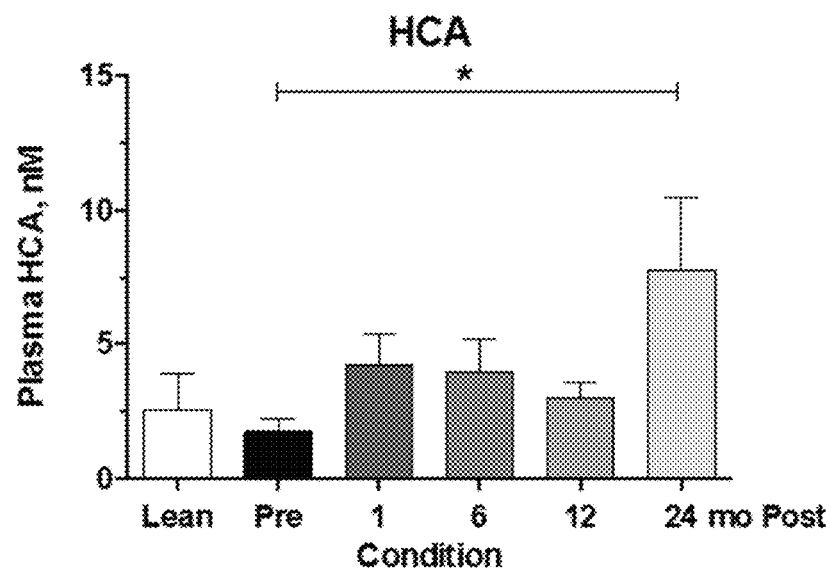

As the increases in UDCA and its conjugates waned to basal levels after one month, what bile acid species contributed to the significant increases at 24 months was further examined. Of the individual bile acids quantified, there was a trend for a gradual rise in four bile acids over time that resulted in significant elevations at 24 months compared to preoperative values. These were the primary bile acids, cholic acid (CA) and chenodeoxycholic acid (CDCA). CA (FIG. 19A) was significantly elevated at 24 months compared to every other time point ($P<0.05$) and CDCA (FIG. 19B) was significantly elevated at 24 months compared to every other time point ($P<0.01$). Besides the 24 month time points, no other pairwise differences were detected between the primary bile acids. Similarly, there was a trend for a gradual increase in the secondary bile acid deoxycholic acid (DCA), the dehydroxylated form of CA, with time. DCA concentration (FIG. 19C) was significantly elevated at 24 months when compared to preoperative concentration ($P<0.01$). There was also a significant increase in the glycine-conjugated form of DCA (FIG. 19D), glycodeoxycholic acid (GDCA), which was observed at 12 months ($P<0.01$) and 24 ($P<0.05$) months compared to the one-month postoperative concentrations. There were no significant differences between any of the other time points. The only other significant difference at the 24 month time point was a small but significant increase in hyocholic acid (FIG. 19E), which is a derivative of CDCA typically found in higher concentrations in murine species but also present in low concentrations in human plasma. Post-hoc dichotomization of the cohort on preoperative diabetes status (i.e. comparing diabetic vs. non-diabetic), however, did show that diabetic patients tended to have slight non-significant trends for higher mean bile acid concentrations overall.

Figure 20:
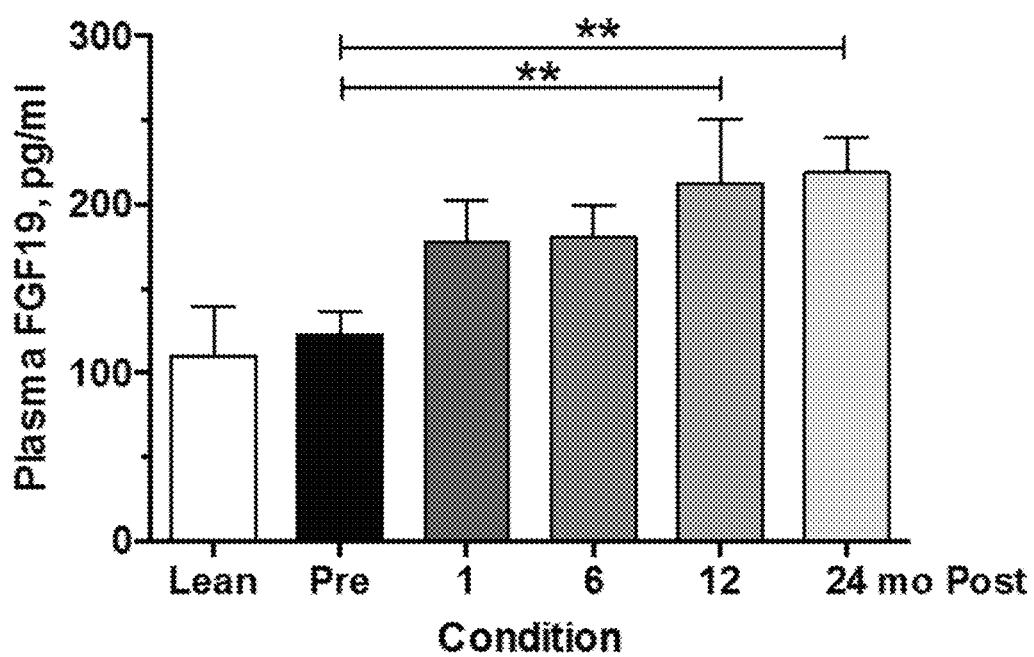
FIG. 20 is a bar graph showing circulating fibroblast growth factor 19 concentrations preoperatively and following RYGB. Serial plasma samples were analyzed for FGF19 concentrations preoperatively and at 1, 6, 12 and 24 months postoperatively. Sample size for each time point in the surgical cohort is 20-21 individuals. Lean individuals (n=8) are included for visual comparison only. Asterisks represent significant differences of indicated time points compared to preoperative levels, **P<0.01.

To determine if other variables might be associated with the changes in bile acids over time, circulating FGF19 levels were measured and examined for significant interactions between anthropomorphic and hormonal variables that were collected as part of the original study. FGF19 is secreted via the enteroendocrine cells of the distal ileum in response to bile acids, and it was posited that the increases seen in bile acids acutely and long-term may be associated with increased FGF19 levels. Compared to preoperative plasma concentrations, FGF19 increased over the study time course (FIG. 20), with gradual increases over time becoming significant in pairwise comparisons at 12 and 24 months relative to preoperative concentrations. However, the increase in FGF19 was not significantly associated with any other study variable that was examined over time (i.e. BMI, HOMA, HISI, EGP).

Within the linear effects model examined next was whether other anthropomorphic or hormonal variables were significantly associated with the changes individual bile acid concentrations or groups of structurally similar bile acids (e.g. conjugated vs. unconjugated, primary vs. secondary) over the time course of the study. All individual and grouped plasma bile acid concentrations were examined in the mixed effects model, and changes in BMI, HOMA, HISI, HbA1C and EGP were examined independently and for significant interactions with the changes in bile acid groups or individual species. However, none of these variables independently or in combination had significant associations with any of the bile acid changes over the course of the study.

Materials & Methods

Study Participants & Approvals.

The Vanderbilt University Institutional Review Board approved all study protocols, consent and study documents. Informed consent was obtained on all subjects prior to voluntary study participation. For full details of these subjects see the previous reports noted above (Dunn J P, et al. Diabetes Care 2012; 35:137-142; Fabbrini E, et al. Gastroenterology 2010; 139:448-455). Briefly, obese men or women 18-60 years old with or without type 2 diabetes were randomized to have a RYGB with omentectomy or not at the time of their operation. These individuals included subjects with a body mass index (BMI)>40 kg/m$^2$ or >35 kg/m$^2$ with one or more comorbid conditions.

Chemicals.

Cholic acid (5β-cholanic acid-3α,7α,12α-triol, CA), α-muricholic acid (5β-cholanic acid-3α,6β,7α-triol, αMCA), β-muricholic acid (5β-cholanic acid-3α,6β,7β-triol, βMCA), chenodeoxycholic acid (5β-cholanic acid-3α,7α-diol, CDCA), deoxycholic acid (5β-cholanic acid-3α,12α-diol, DCA), hyodeoxycholic acid (5β-cholanic acid-3α,6α-diol, HDCA), ursodeoxycholic acid (5β-cholanic acid-3α,7β-diol, UDCA), taurocholic acid (5β-cholanic acid-3α,7α,12α-triol-N-[2-sulphoethyl]-amide, TCA), tauro-α-muricholic acid (5β-cholanic acid-3α,6β,7α-triol-N-[2-sulphoethyl]-amide, TaMCA), lithocholic acid (5β-cholanic acid-3α-ol, LCA), tauro-β-muricholic acid (5β-cholanic acid-3α,6β,7β-triol-N-[2-sulphoethyl]-amide, TβMCA), tauro-ω-muricholic acid (5βcholanic acid-3α,6α, 7β-triol-N-[2-sulphoethyl]-amide, TωMCA), taurochenodeoxycholic acid (5β-cholanic acid-3α,7α-diol-N-[2-sulphoethyl]-amide, TCDCA), taurodeoxycholic acid (5β-cholanic acid-3α,12α-diol-N-[2-sulphoethyl]-amide, TDCA), taurohyodeoxycholic acid (5β-cholanic acid-3α,6α-diol-N-[2-sulphoethyl]-amide], THDCA), and taurolithocholic acid (5β-cholanic acid-3α-ol-N-[2-sulphoethyl]-amide, TLCA), tauroursodeoxycholic acid (5β-cholanic acid-3α,7β-diol-N-[2-sulphoethyl]-amide, TUDCA), glycocholic acid, (5β-cholanic acid-3α,7α,12α-triol-N-[carboxymethyl]-amide, GCA), glycochenodeoxycholic acid (5β-cholanic acid-3α, 7α-diol-N-[carboxymethyl]-amide, GCDCA), glycodeoxycholic acid (5β-cholanic acid-3α,12α-diol-N-(carboxymethyl)-amide, GDCA), glycohyodeoxycholic acid (5β-cholanic acid-3α,6α-diol-N-(carboxymethyl)-amide, GHCA), glycoursodeoxycholic acid (5β-cholanic acid-3α, 7β-diol-N-(carboxymethyl)-amide, GUDCA), and glycolithocholic acid (5β-cholanic acid-3α-ol-N-(carboxymethyl)-amide, GLCA) were purchased from Steraloids, Inc. (Newport, R.I.). cholic-2,2,4,4-d4 acid (5β-cholanic acid-3α,7α,12α-triol-2,2,4,4-d4, d4-CA), taurocholic-2,2,4,4-d4 acid (5β-cholanic acid-3α,7α,12α-triol-N-[2-sulphoethyl]-amide, TCA-d4), chenodeoxycholic-2,2,4,4-d4 acid (5β-cholanic acid-3α,7α-diol-2,2,4,4-d4, CDCA-d4); glycocholic-2,2,4,4-d4 acid, (5β-cholanic acid-3α,7α,12α-triol-N-[carboxymethyl]-amide-2,2,4,4-d4, GCA-d4), glycochenodeoxycholic-2,2,4,4-d4 acid (5β-cholanic acid-3α,7α-diol-N-[carboxymethyl]-amide-2,2,4,4-d4, GCDCA-d4), were purchased from C.D.N. isotopes Inc. (Pointe Claire, Montreal, Quebec, Calif.). Tauro-β-muricholic-2,2, 4,4-d4 acid (5β-cholanic acid-3α,6β,7β-triol-N-[2-sulphoethyl]-amide-2,2,4,4-d4, TβMCA-d4), was purchased from United States Biological Corp., Swampscott, Mass.). HPLC grade water, acetonitrile, ethanol, and methanol were used for analyses. Ammonium acetate and ammonia were purchased from Sigma Chemicals (St. Louis, Mo.). Formic acid was purchased from Thermo Scientific (Rockford, Ill.)

Hyperinsulinemic-Euglycemic Clamps.

To assess hepatic and peripheral insulin sensitivity, subjects underwent a hyperinsulinemic-euglycemic clamp (Dunn J P, et al. Diabetes Care 2012; 35:137-142; Fabbrini E, et al. Gastroenterology 2010; 139:448-455). Briefly, participants were admitted to the Vanderbilt Clinical Research Center the evening before the clamp, fed a standardized meal, and subsequently fasted overnight. The following morning catheters were placed for infusions and blood sampling as part of the clamp procedure.

Body Composition Analysis & Energy Expenditure.

Dual-energy X-ray absorptiometry was used to measure both fat mass and fat free mass at each of the study time points except for the one month visit (Tataranni P A, et al. Am J Clin Nutr 1995; 62:730-734). Energy expenditure was measured using whole-room indirect calorimeter as described (Fabbrini E, et al. Gastroenterology 2010; 139: 448-455).

Blood Collection & Hormone Measurements.

Blood was collected for bile acid and other hormone measurements were collected at the indicated time points before or after RYGB following a 12 h fast. Blood was centrifuged at 10,000×g for 10 minutes and plasma frozen at −80° C. for further analysis. Human fibroblast growth factor 19 (FGF19) plasma concentrations were measured using a quantitative sandwich ELISA (R&D Systems, Minneapolis, Minn.).

Calibrators & Controls.

Stock solutions of 2.5 mM of all bile acids (THCA, HCA, TαMCA, TβMCA, TωMCA, HDCA, THDCA: 10 mM) were used to prepare calibrators with concentrations of 100 µM in methanol. For the preparation of calibrators, bile acids were mixed to achieve final concentrations of 20, 2.5, 0.75, 0.25, 0.05, 0.015, 0.005 µM. To prepare 20 ml of a 2.0 nM internal standard, 250 µl each of d4-CDCA, d4-TCA, d4-GCDCA and 500 µL d4-CA, d4-TβMCA and d4-GCA were added to 20% (v/v) acetonitrile.

Sample Preparation for UPLC/ESI-MS.

To 50 µl of plasma the following was added: 200 µl of 100 mM aqueous sodium hydroxide and 50 µl of internal standard. The sample was heated at 64° C. for 30 min, centrifuged for 10 min at 14,400×g, and the supernatant acidified to pH 7.0 with 50 µL of 0.1M hydrochloric acid. The sample was brought to a final volume of 1 ml with water and applied to a 1 cc (30 mg) Oasis HLB cartridge (Waters, Milford, Mass.) previously equilibrated first with 1 ml of methanol, then 1 ml of water (Rodrigues C M, et al. Biomed Chromatogr 1996; 10:1-5). The column bound bile acids were washed with 1 ml of 5% (v/v) aqueous methanol then 1 ml of 2% (v/v) aqueous formic acid. Bile acids were eluted from the column with 1 ml of 2% (v/v) ammonia in methanol and the eluent evaporated to dryness using a rotary evaporator at 30° C. for 2 hr. Samples were resuspended in 100 µl of 25% (v/v) acetonitrile in water.

Liquid Chromatography.

An Acquity ultra performance liquid chromatography system (UPLC; Waters, Milford, Mass.) employing a Luna C18(2) 50×2.0 mm, 3 mm column, C18 4×2.0 mm precolumn, both from Phenomenex (Torrance, Calif.), was heated to 50° C., and a binary solvent system of 20% (v/v) acetonitrile in water (mobile phase A) and 80% (v/v) acetonitrile in water (mobile phase B) both containing 1 mM ammonium acetate were used to resolve plasma bile acids. The injection volume onto the column was 15 µL. The flow rate was 400 µl/min into the MS. Chromatography was similar to a published method and started with a solvent mixture of 95% A that decreased to 85% A at 15 min, to 75% at 20 min, then to 25% at 22 min where after it increased to 95% A at 24 min for 3 min (Hagio M, et al. J Lipid Res 2009; 50:173-180).

Mass Spectrometry.

MS analysis was performed using a TSQ Quantum mass spectrometer (ThermoFinnigan, Sunnydale, Calif.) equipped with an ESI probe in negative-ion mode. Quantitation was done in a multiple reaction monitoring mode with a collision energy of 10 V. The following (optimized) parameters were used for the detection of the analytes and the internal standard; N2 sheath gas, 49 p.s.i.; N2 auxiliary gas, 25 p.s.i.; spray voltage, 3.0 kV; source CID, 25 V; capillary temperature, 300° C.; capillary offset, −35 V; tube lens voltage, 160 V; Q2 gas pressure, 1.5 mtorr; Q3 scan width 1 m/z; Q1/Q3 peak widths at half-maximum, 0.7 m/z. Calibration curves and concentration of individual bile acids were calculated by LCQuan 2.5.5 software (ThermoFinnigan). Concentrations of individual bile acids were calculated from peak area in the chromatogram detected with SRM relative to the appropriate internal standard.

Statistical Analysis.

Data are reported as mean±standard error of the mean unless otherwise indicated. Repeated subject measurements and hormone concentrations over time were compared using mixed-effects modeling with Bonferroni corrections for pairwise comparisons. A priori determination of covariates to be independently examined for associations with changes in bile acids included: BMI, HOMA, HISI, HbAl C, EGP and energy expenditure. Data analysis and visualization was performed using IBM SPSS (version 22) and GraphPad Prism (version 6). As this was an exploratory study using previously collected patient samples, there was no specific power or sample size calculation for the data examined herein. In an attempt to increase statistical power it was aimed to have a sample size of at least 20 individuals at each time point, as most other studies examining similar endpoints have been published with fewer individuals (n=6-12). Differences were considered statistically significant using alpha=0.05.

Figure 21A:
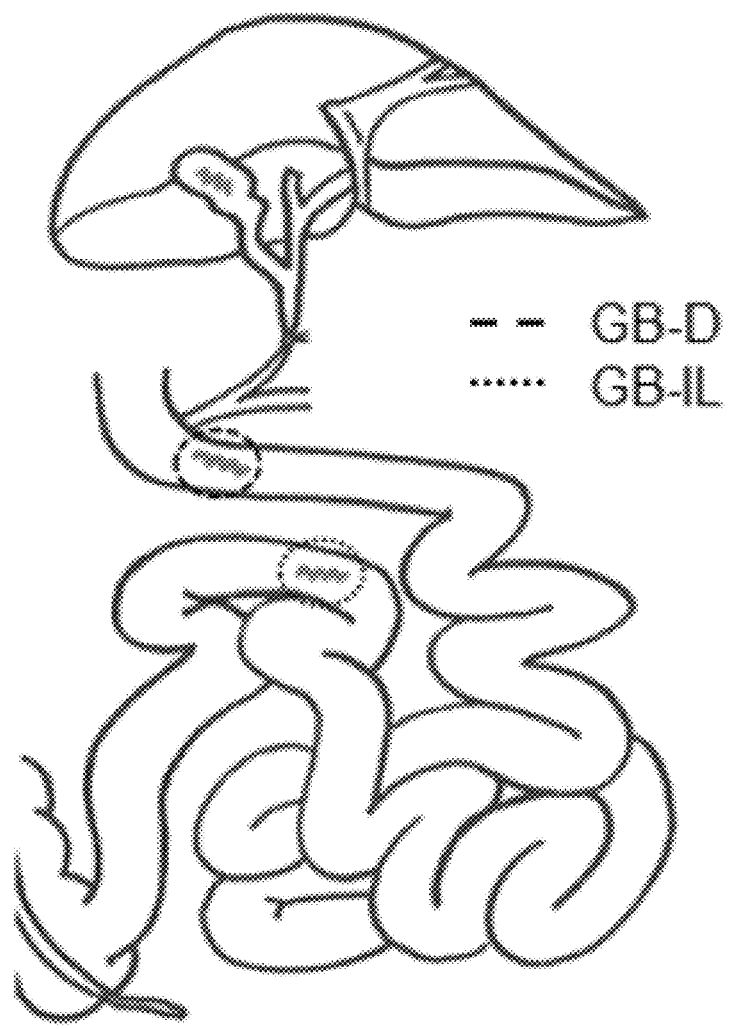

Example 3: Attenuated Cocaine Conditioned Reward in Surgical and Drug Models of Altered Bile Acid Signaling Results Biliary diversion involves ligation of the common bile duct and anastomosis of the gall bladder to the ileum (FIG. 21A; GB-IL), a part of the small intestine densely populated by bile acid receptors and reuptake transporters, immune cells, and enteroendocrine cells. Normally, bile acids produced from cholesterol in the liver enter the proximal small intestine at the duodenum; the result of biliary diversion surgery is thus to divert the flow of bile acids to the distal small intestine. In the sham surgery, the common bile duct is ligated and the gall bladder is anastomosed to the duodenum (FIG. 21A; GB-D). Consequently, in the sham, bile acids enter gut lumen at a level of the small intestine consistent with normal anatomy.

As shown in Example 1, GB-IL mice reduced their consumption of high fat food and exhibited significant long-term weight loss. It is conceivable that, by reducing the intake of calorically dense, rewarding food, biliary diversion produces weight loss in part through changes in reward circuitries. To test the hypothesis that biliary diversion modulates reward processes, and to define strategies to normalize impairments in the brain's reward system, the effect of the surgery was studied on the stimulant and rewarding properties of cocaine. Psychostimulants such as cocaine and amphetamine hijack brain reward circuits for natural rewards (e.g. palatable food) to cause addiction. In light of the fact that cocaine acts directly on striatal-accumbal dopamine (DA) circuits in the brain, measuring cocaine's actions in the setting of biliary diversion offers a relatively pure measure of the effects of this bariatric surgery on reward pathways and addictive behaviors. Furthermore, this model may provide new hope for the treatment of reward-based (substance use) disorders, including cocaine abuse.

Figure 21B:
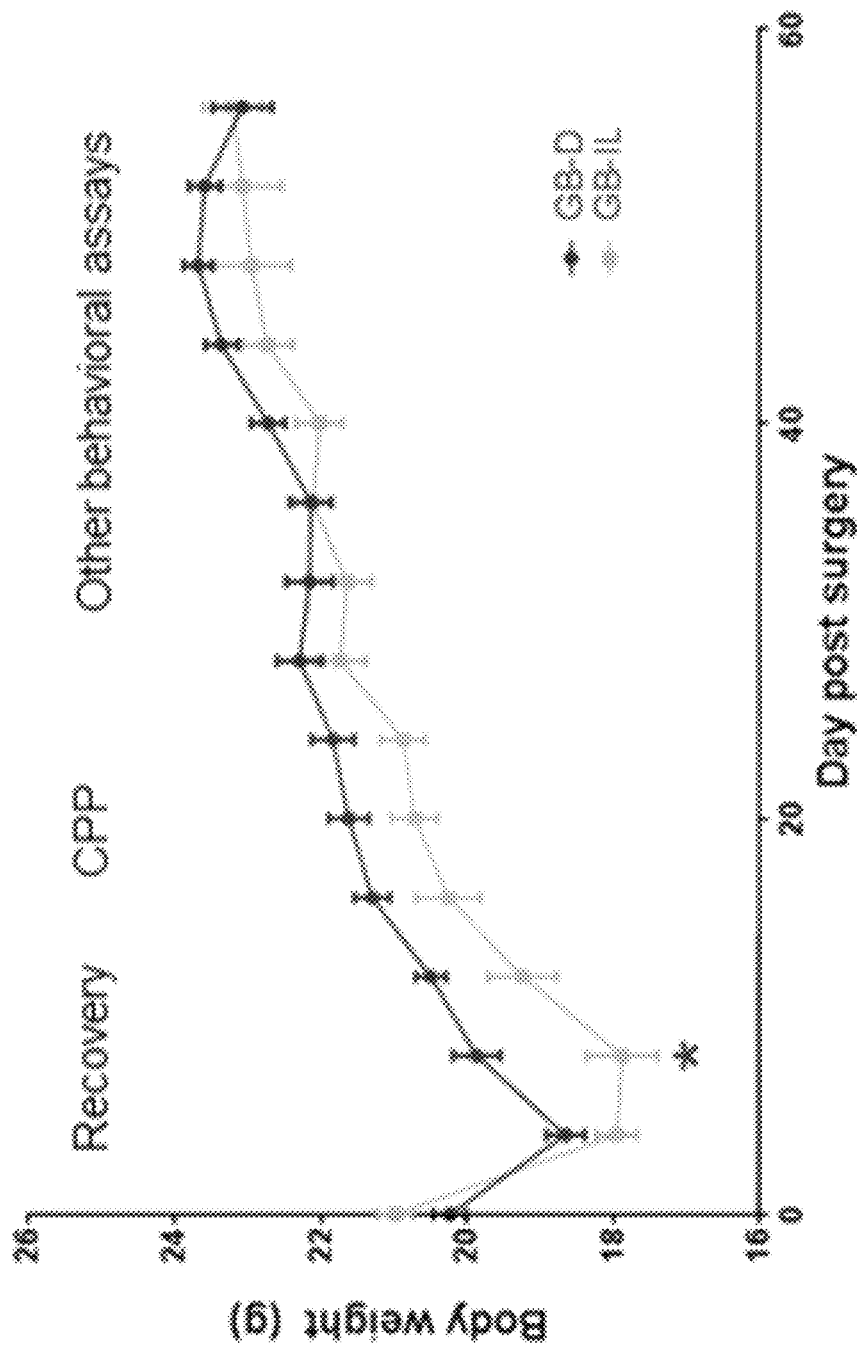

Unlike other bariatric surgeries, such as Roux-en-Y gastric bypass, mice undergoing biliary diversion experience fewer complications, surgery time, and do not require post-surgical dietary supplementation. To avoid physiological adaptations induced by a high fat diet, experiments were performed in lean animals fed a chow diet for the entirety of the study. Early post-surgical weight loss was greater in the GB-IL group compared with the GB-D sham group (FIG. 21B). However, by day 12 post-surgery, there were no significant differences in body weight between groups. This strongly suggests that the homeostatic regulation of body weight in GB-IL mice parallels that of the GB-D sham group.

Figure 21D:
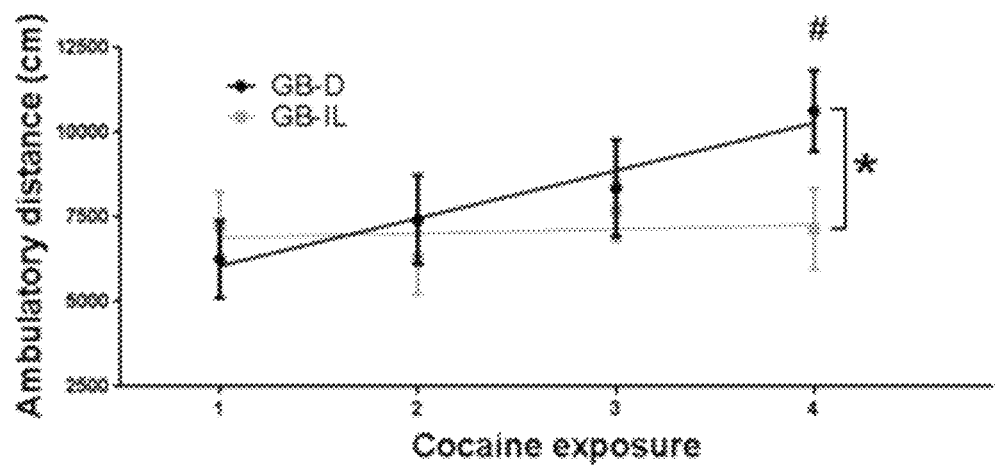
Figure 21E:
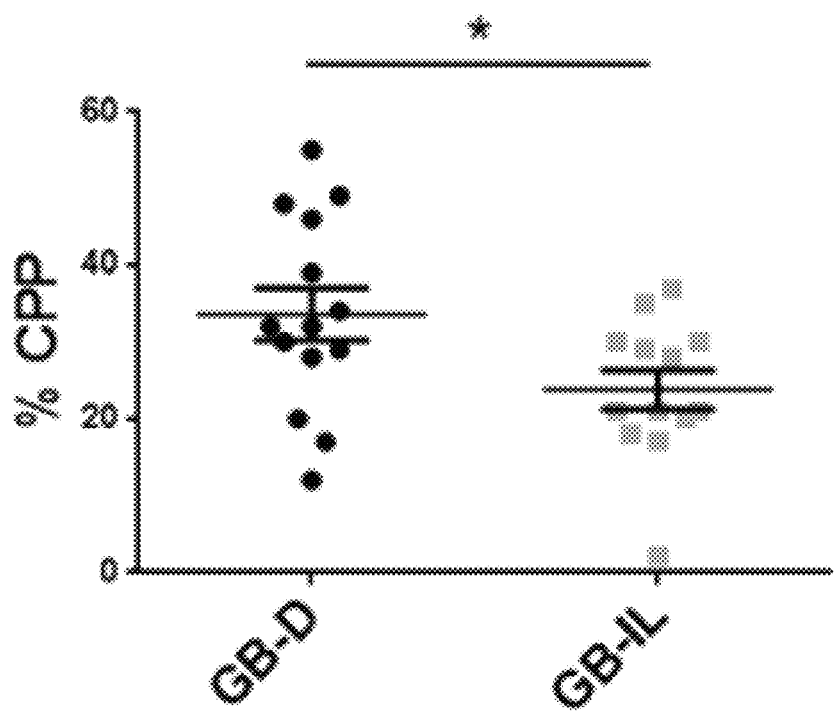
Figure 21F:
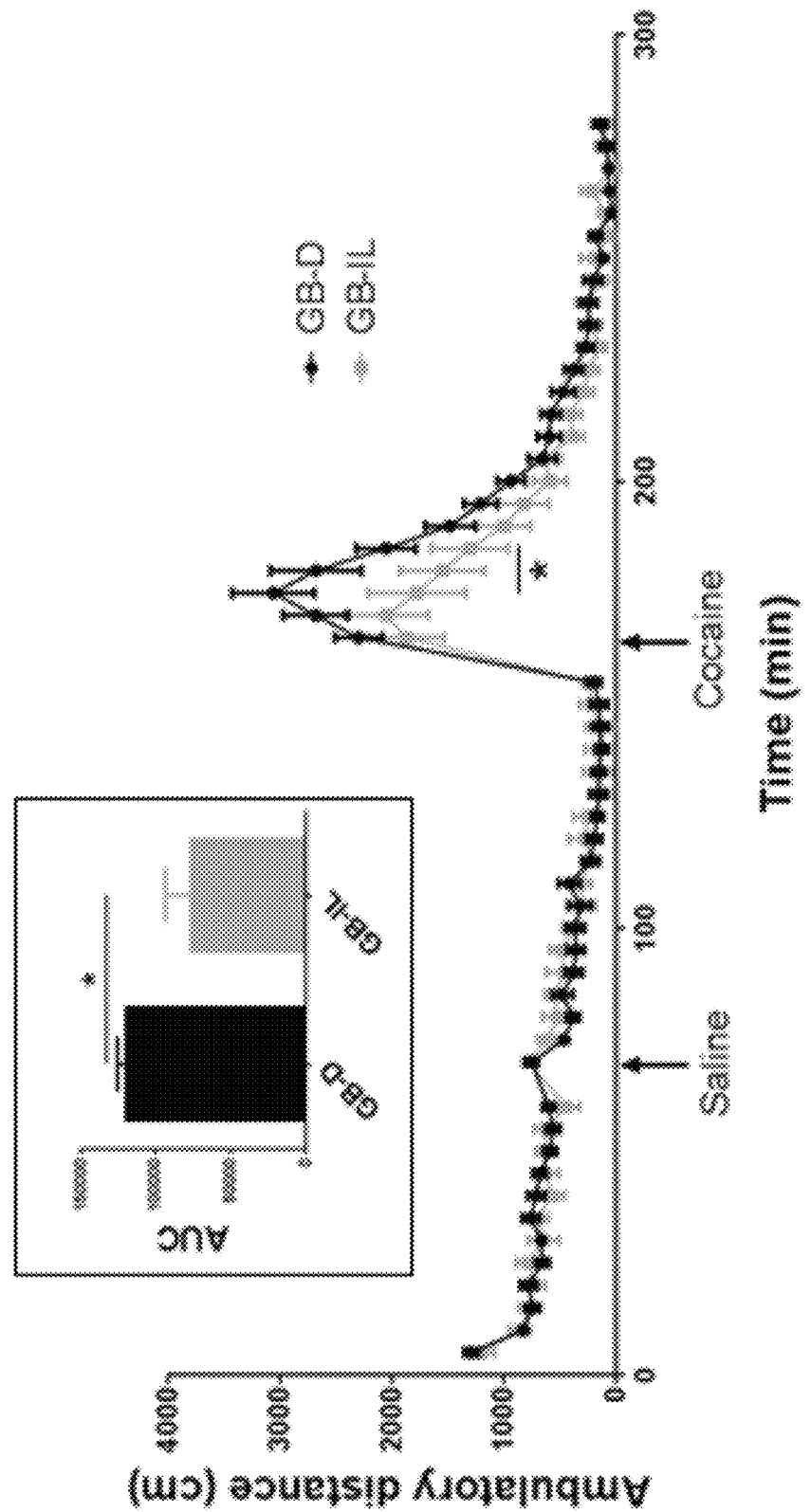

After a 14 day post-surgical recovery period, mice began the cocaine CPP paradigm to measure preference for a cocaine-paired environment (FIG. 21C). Afterwards, mice underwent further behavioral testing and were later sacrificed. Cocaine CPP involved a single preconditioning session in the absence of drug followed by 8 days of conditioning alternating between saline and cocaine injections (20 mg/kg, i.p.) in a dual compartment apparatus. Finally, a post-conditioning, drug-free preference test was performed on day 10. During conditioning sessions, locomotor behavior was measured. Notably, while control mice exhibited significant locomotor sensitization by the fourth exposure to cocaine, the GB-IL mice did not (FIG. 21D). In contrast to the GB-D controls, the regression of locomotor activity over the four cocaine exposures revealed no significant deviance from a zero slope in the GB-IL group (FIG. 21D). Previous work strongly suggests that psychomotor sensitization indirectly points to the development of "incentive sensitization", indicating important molecular adaptations have occurred in mesotelencephalic DA systems in the process of developing an addiction (Robinson T E, et al. (2008). Philos Trans R Soc Lond B Biol Sci. 363(1507):3137-3146). The lack of locomotor sensitization in the bariatric model may thus support impairments in the central encoding of reward. To this end, analysis of conditioning in the CPP paradigm revealed that, while both groups formed a place preference for cocaine, the preference of the GB-IL mice for the cocaine-paired side of the chamber was significantly less than that observed for the GB-D mice (FIG. 21E). Finally, in an open field paradigm performed following CPP, neither spontaneous locomotion nor saline-induced locomotion in GB-IL mice significantly differed from control mice; however, in agreement with FIG. 21D, cocaine-induced locomotion (20 mg/kg, i.p.) was significantly attenuated between 15 and 25 minutes post-injection (FIGS. 21F and 21F inset).

Figure 24A:
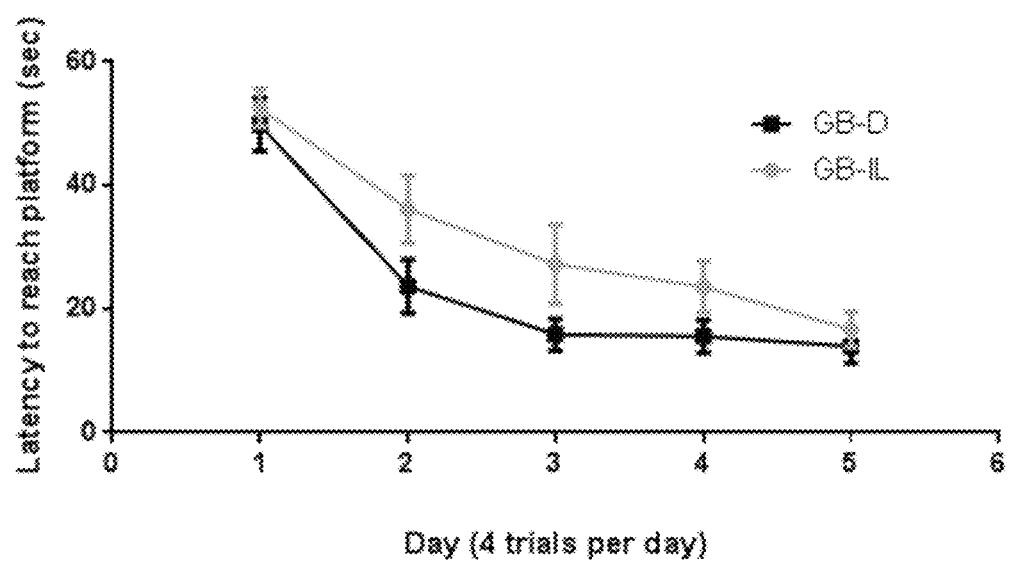
FIGS. 24A to 24F show biliary diversion does not alter learning, memory, motor function, or affective behavior.
Figure 24C:
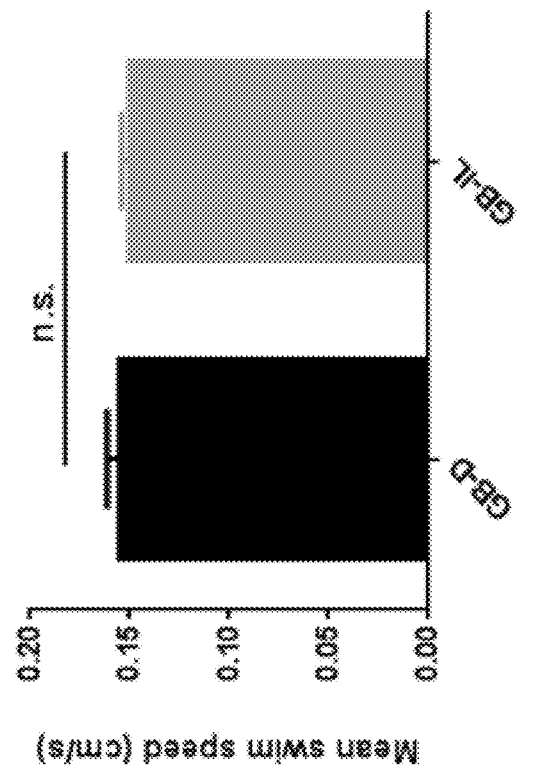
Figure 24B:
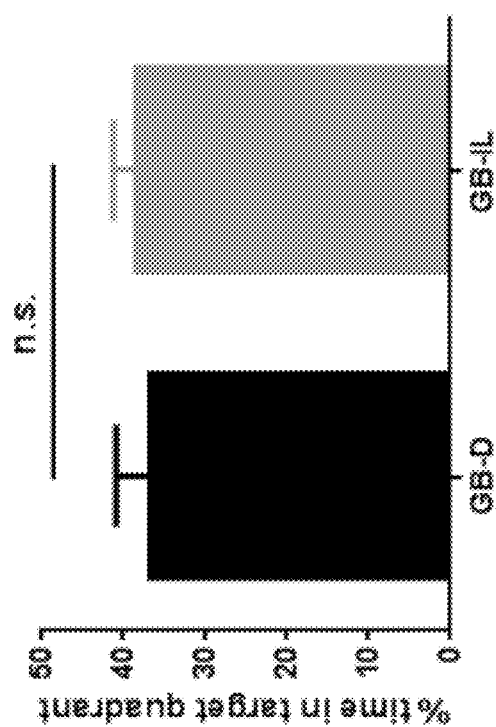
Figure 24D:
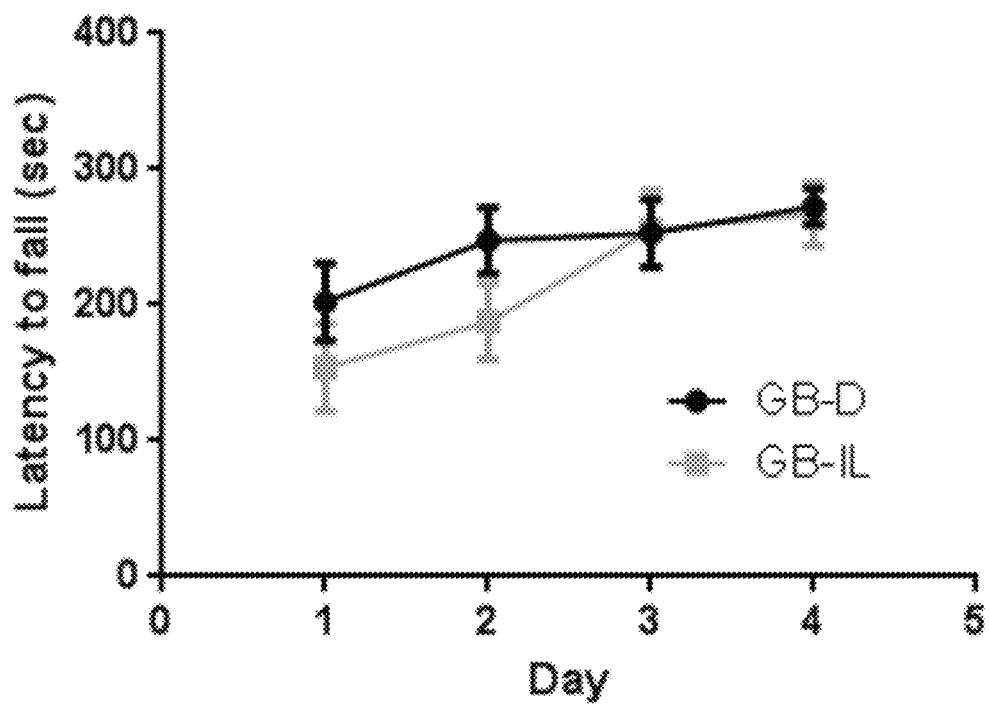
Figure 24E:
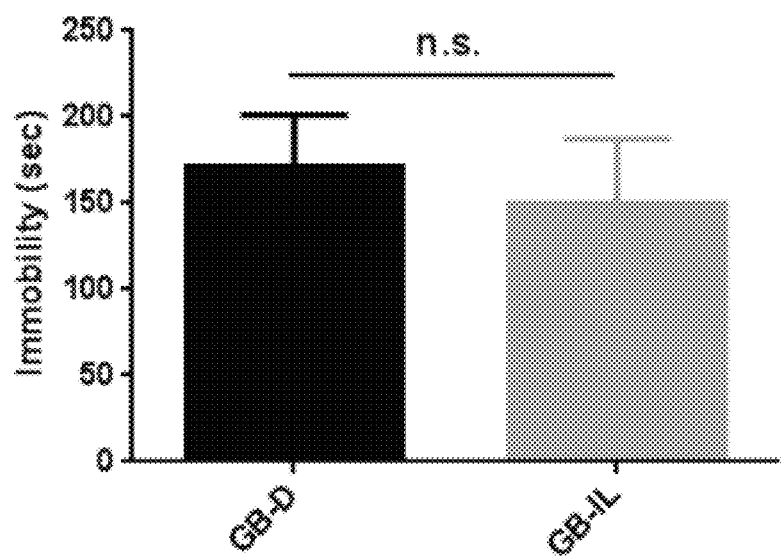
Figure 24F:
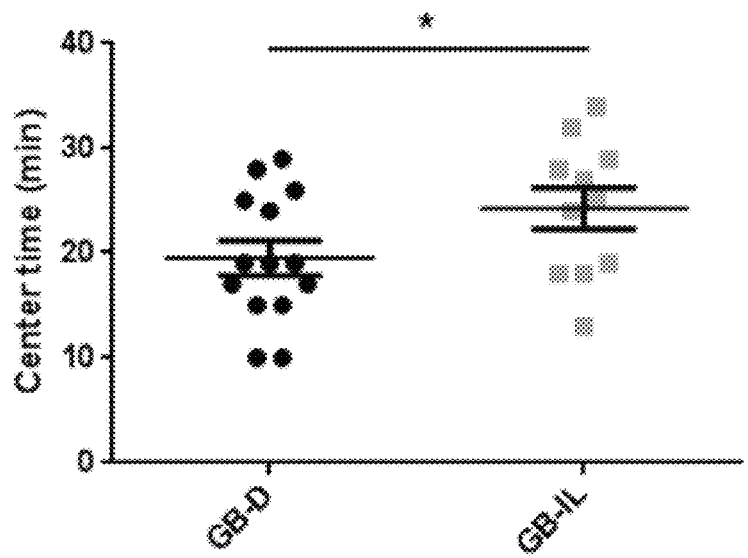

Importantly, reductions in conditioning to cocaine were not attributed to impaired spatial learning or memory capabilities, as no significant impairments in performance on a hidden water maze task were observed (FIGS. 24A-C). Moreover, no generalized impairments were observed in motor abilities (FIG. 24D) or motivated behavior/affective state in a tail suspension test (FIG. 24E). However in the open field setup, a significant increase was not observed in center time in the GB-IL group (FIG. 24F), suggesting that the surgery may also be anxiolytic.

Figure 22B:
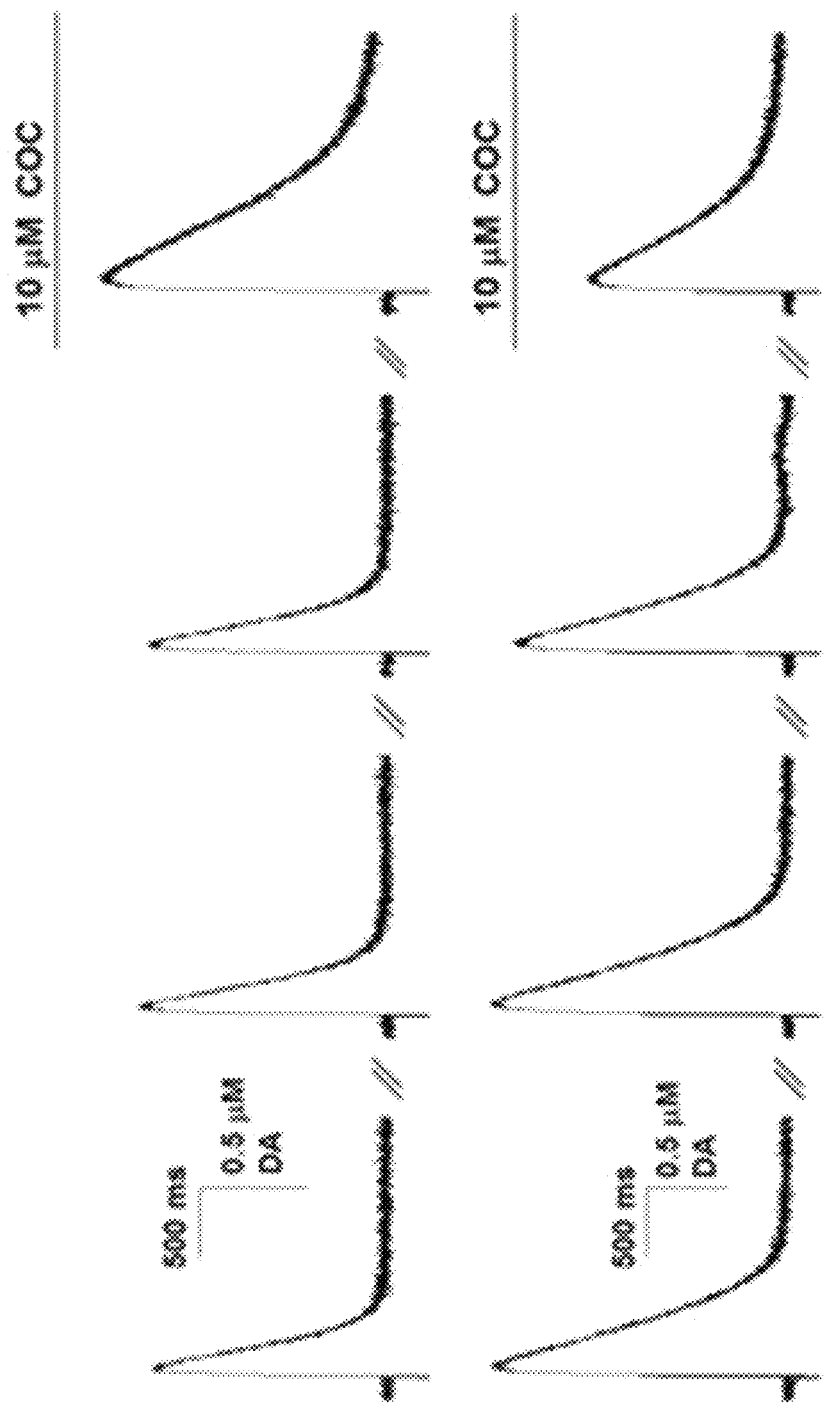
FIGS. 22A to 22F shows constant voltage amperometric recording of DA from the nucleus accumbens.
Figure 22A:
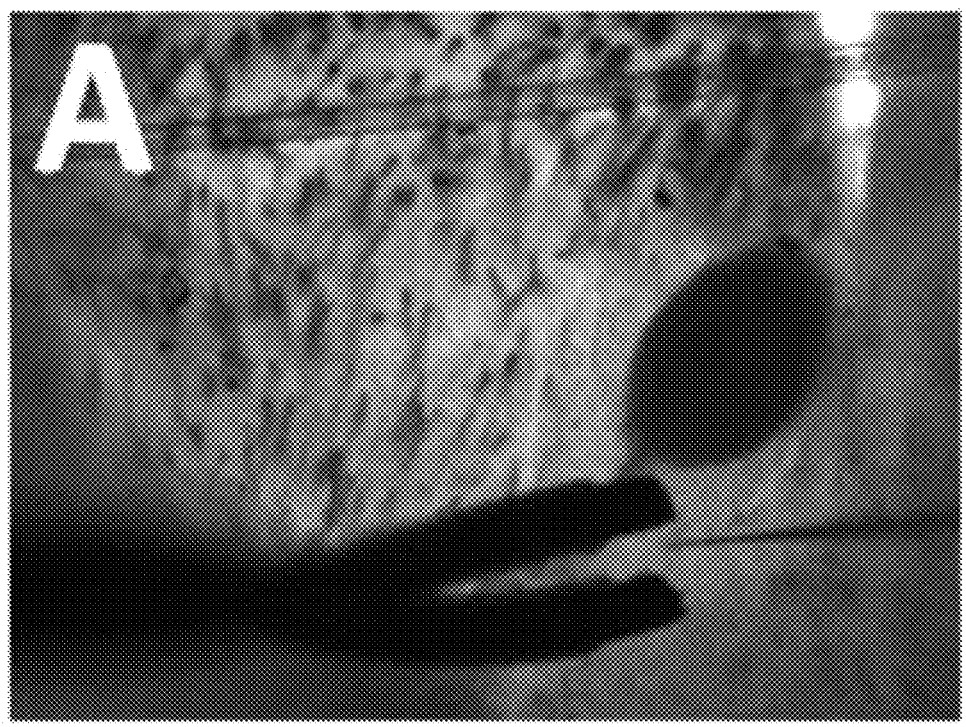
Figure 22C:
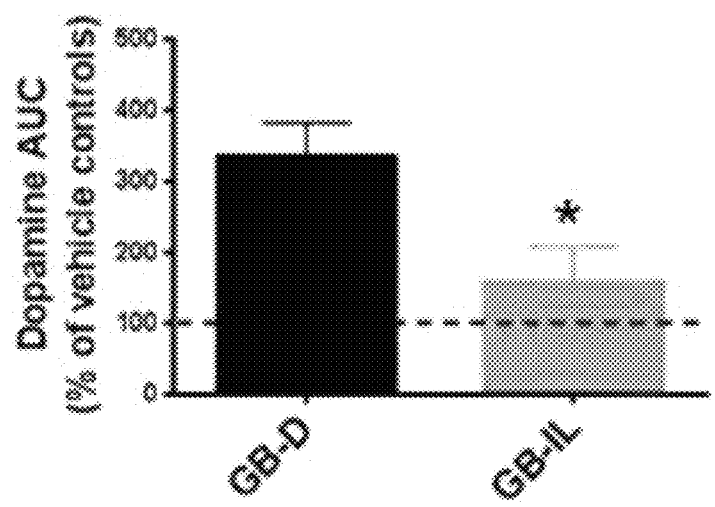
Figure 22D:
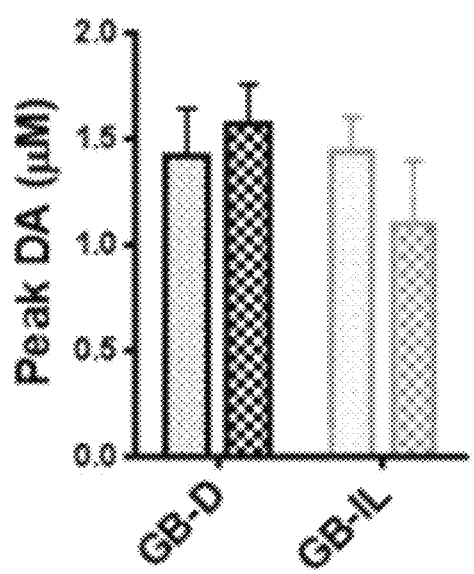
Figure 22E:
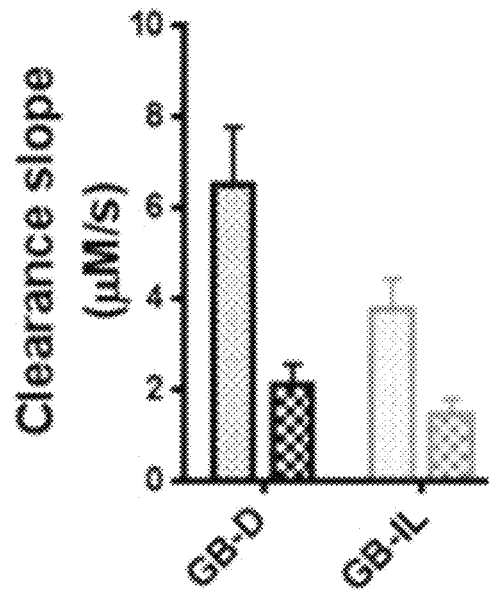
Figure 22F:
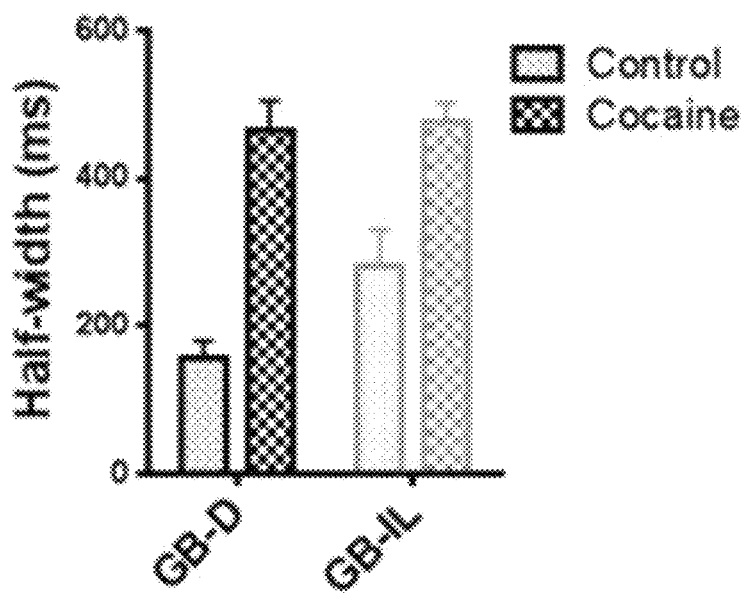
Figure 25:
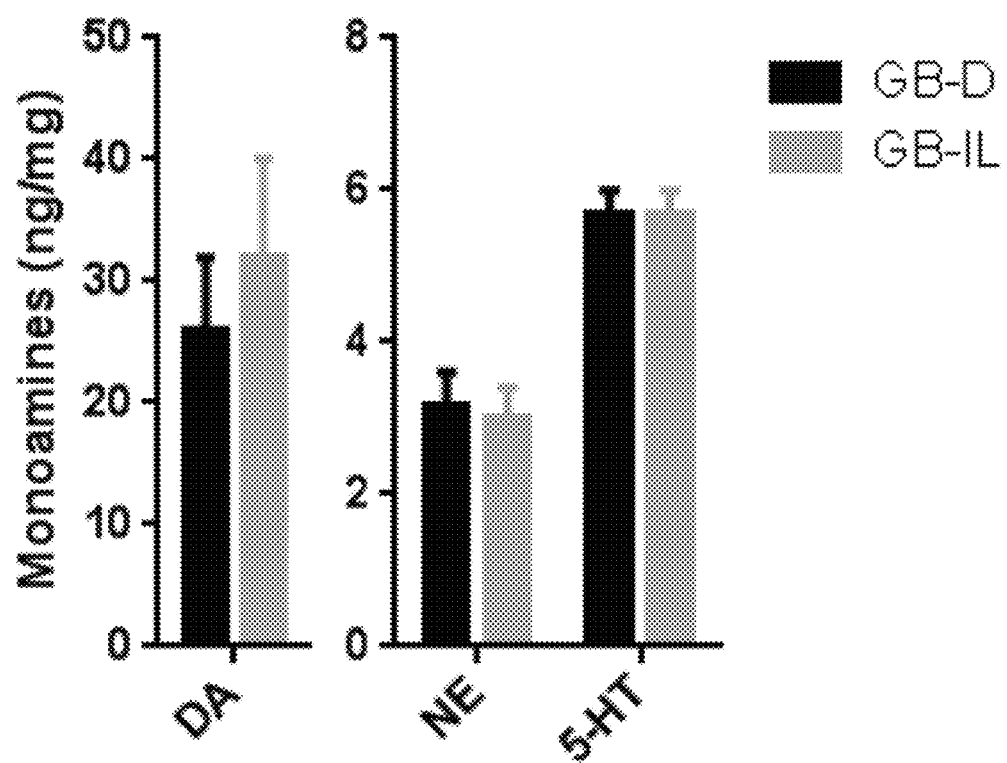
FIG. 25 shows biliary diversion does not alter monoamine levels in nucleus accumbens, as measured by HPLC. There were no significant differences between groups in levels of accumbal DA, NE, or 5-HT.
Figure 26:
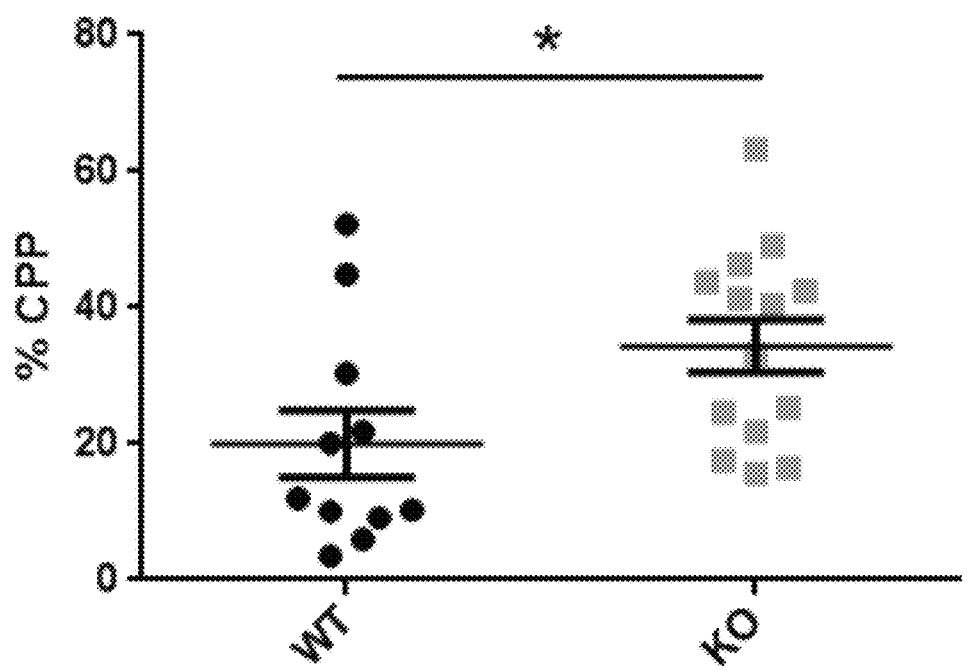
FIG. 26 shows cocaine CPP is elevated in TGR5 knock-out mice compared to their wild-type littermates. TGR5 constitutive knock-out (KO) mice exhibited significantly elevated preference for the cocaine-paired compartment over their wild-type (WT) littermates, suggesting that endogenous signaling through the TGR5 bile acid receptor may act to suppress the rewarding properties of cocaine.

Experiments were then conducted to define potential central mechanisms by which biliary diversion attenuates cocaine reward. Attention was focused on the accumbal DA system, the major target of cocaine actions. Total accumbal tissue levels of DA and its related monoamines, norepinephrine (NE) and serotonin (5-HT), were not significantly altered in the GB-IL mice with respect to GB-D (FIG. 25). In the absence of an overt neurochemical phenotype, evoked DA responses were measured at baseline and in the presence of cocaine using an ex vivo preparation from the nucleus accumbens of GB-IL and GB-D mice sensitized to cocaine (FIG. 22A). Three comparable baseline amperometric recordings were taken under electrical stimulation at five minute intervals (FIG. 22B). Cocaine (10 µM) was washed into the bath solution just prior to the final electrical stimulation. As expected, cocaine prolonged the evoked DA response in both groups. Interestingly, the area under the curve for the response in the presence of cocaine compared to the average baseline evoked DA revealed a significantly blunted response in the GB-IL mice (FIG. 22C). Somewhat surprisingly, this effect appears to be mediated by reduced DA clearance at baseline, as the clearance slope was reduced in the GB-IL mice at baseline compared to GB-D, while the half-width of clearance was elevated (FIG. 22E-2F). There were no differences in peak DA amplitude between the two groups at baseline or with cocaine (FIG. 22D).

Figure 23A:
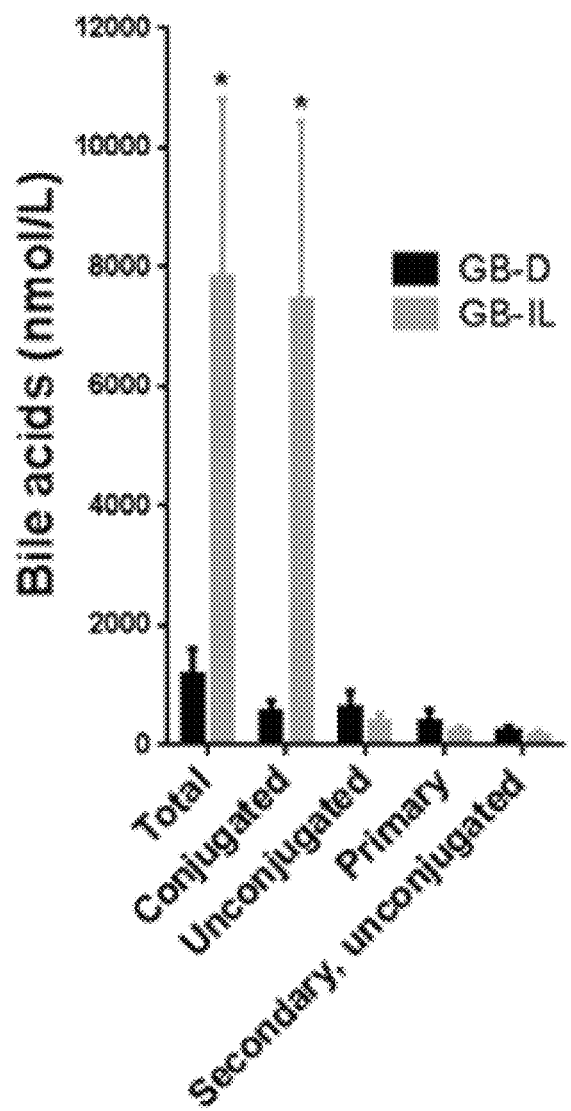
FIGS. 23A to 23C show treatment with a bile acid receptor agonist recapitulates reduction in cocaine CPP.
Figure 23B:
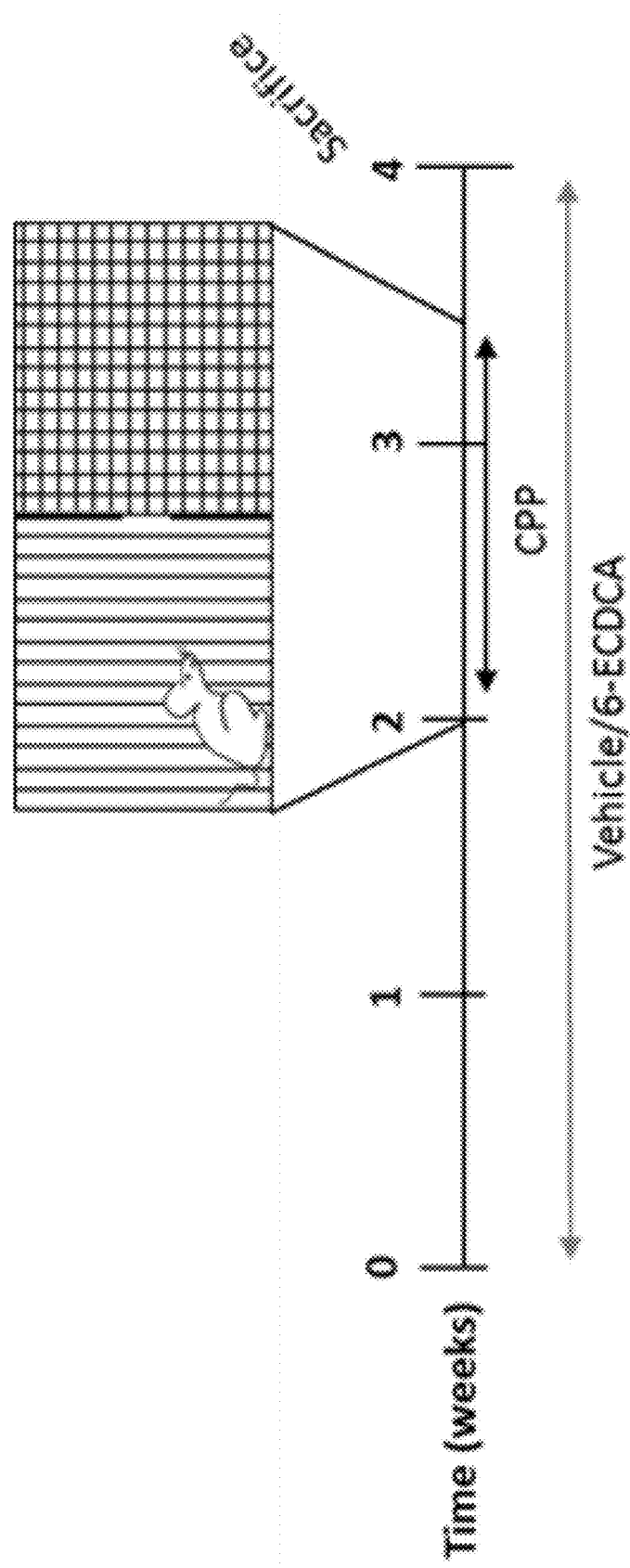
Figure 23C:
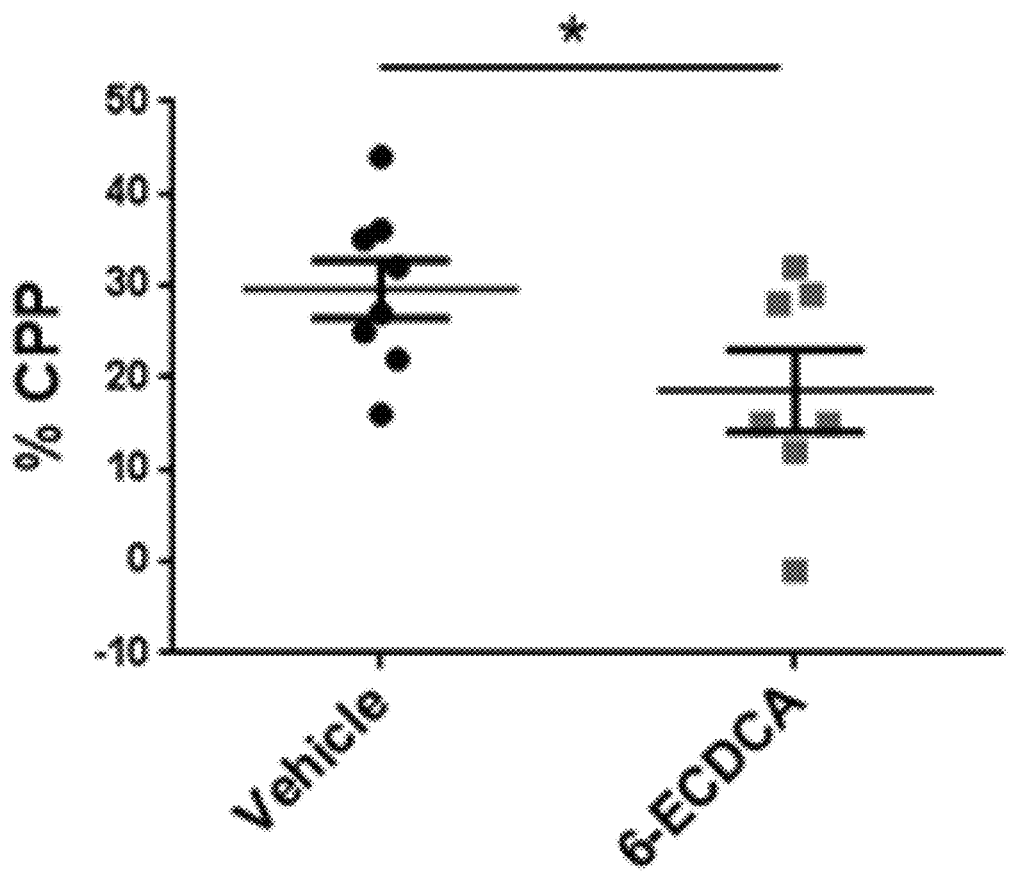

Hormonal bile acid signaling was a clear mechanistic candidate for the observed effects on cocaine actions based on the fact that this surgery diverts the flow of bile acids to a region of the intestine uniquely populated by bile acid receptors. In addition to their canonical role as fat emulsifiers, bile acids are increasingly recognized for their hormonal effects through two main bile acid receptors, the farnesoid x receptor (FXR) and TGR5 (Fiorucci S, et al. (2009). Trends Pharmacol Sci. 30(11):570-580). Of note, GB-IL mice exhibit an increase in total and conjugated circulating bile acids, while levels of primary, secondary, and unconjugated bile acids remained unchanged (FIG. 23A). This increased population of bile acids might promote enhanced hormonal signaling with direct or indirect effects on the central nervous system. To determine whether enhanced agonism at bile acid receptors is sufficient to reduce the rewarding properties of cocaine, a chronic pharmacologic model was developed to replicate the time course of changes following surgery. For two weeks prior to the initiation of cocaine CPP, mice were treated orally with obeticholic acid (OCA, 10 mg/kg), a potent bile acid receptor agonist ($EC_{50}$ TGR5/FXR ratio=2.1) (Pellicciari R, et al. (2007). J Med Chem. 50(18):4265-4268), or vehicle (FIG. 23B). The treatment continued until sacrifice 4 weeks following drug initiation. No differences in body weight were noted throughout the study. As hypothesized, this intervention paralleled the results from the surgical model: mice treated with OCA, compared with vehicle treatment, exhibited decreased cocaine CPP (FIG. 23C) and impaired cocaine-induced locomotion.

In summary, a weight loss surgery that alters bile acid signaling in lean mice induces changes in the stimulant and rewarding properties of cocaine. Notably, this gut-based surgery alters brain DA homeostasis at cocaine's site of action. These findings inspired development of a pharmacologic model under the hypothesis that changes in hormonal bile acid signaling are involved in the effects of the surgery. Using this model, it was determined that treatment with a bile acid receptor agonist is sufficient to recapitulate a reduction in cocaine CPP and that this effect is driven by TGR5 receptor signaling. While it seems most likely that peripheral TGR5 in the ileum is the primary mechanistic driver, a direct central mechanism cannot be ruled out as TGR5 receptors are expressed in the brain (Keitel V, et al. (2010). Glia. 58(15):1794-1805). Within the ileum, TGR5 receptors are expressed on enteroendocrine L cells. Their activation is known to induce the production of hormones like glucagon-like peptide 1 (GLP-1) with effects on neural responses and behavior (Reddy I A, et al. (2014). Neurochem Int. 73:49-55). Furthermore, signaling through the GLP-1 receptor has been shown to modulate DA neurotransmission (Reddy I A, et al. (2014). Neurochem Int. 73:49-55; Narayanan N S, et al. (2010). Front Neuroendocrinol. 31(1): 104-112).

The implications of these findings on clinical therapies are profound. The powerfully addictive nature of cocaine and other psychostimulants has presented a major public health challenge. So far, treatment of addiction to drugs in this class is limited to behavioral therapy. Using a surgery to treat cocaine dependence may seem an extreme solution, although a surgical approach subverts concerns of patient adherence which is an impediment to the treatment of reward-based disorders. The finding that the TGR5 bile acid receptor underlies, in part, the efficacy of biliary diversion on cocaine reward, may provide a more moderate pharmacologic approach. Indeed, the TGR5 agonist used in the current study is already in clinical trials to treat several hepatic disorders (Fiorucci S, et al. (2011). Mini Rev Med Chem. 11(9):753-762).

Methods

Mice:

Male wild-type C57BL/6J mice were acquired from Jackson Laboratories (Bar Harbor, Me.) at 5 weeks of age. Mice were group housed at a Vanderbilt University housing facility with ad libitum access to standard chow and water. The temperature- and humidity-controlled facility is maintained on a 12:12 h light:dark cycle (lights on 0700-1900 h) and all experiments were performed during the light phase. Mice were acclimated to the Vanderbilt housing facility for one week prior to surgery. Surgery (GB-D or GB-IL) occurred at 6 weeks of age. Mice were given at least 2 weeks to recover from surgery after which they were moved to the Neurobehavior Core facility at Vanderbilt and were handled for 3 days. At this point, mice either underwent behavioral testing (beginning with conditioned place preference) or were sensitized to cocaine without behavioral testing. All protocols were approved by the Vanderbilt University Institutional Animal Care and Use Committee.

Surgery:

The control surgery (GB-D) and experimental surgery (GB-IL) were performed as 163 previously described (see Abumrad paper, Nature Communications, in press, 2015).

Amperometry in Ex Vivo Slice Preparation:

Electrically evoked dopamine release in the nucleus accumbens was measured by standard methods (see Schmitz et al J Neurosci. 2002 Sep. 15; 22(18):8002-9). DA release was stimulated with a bipolar electrode placed on the surface of the slice and recorded with a carbon fiber electrode.

High Performance Liquid Chromatography:

HPLC to measure monoamines in the nucleus accumbens was performed as previously described (Reddy I A, et al. (2014). ACS Chem Neurosci. 5(10):943-951).

Conditioned Place Preference and Locomotor Sensitization:

CPP was performed as previously described, with modifications (Graham D L, et al. (2013). Mol Psychiatry. 18(9): 961-962). Briefly, mice were weighed and then acclimated to the testing room for at least 20 minutes prior to testing each day. During the first phase (pre-conditioning, day 1), mice were placed on the grid floor side of a two chamber apparatus. For 30 min, the mice had free access to both sides of the apparatus, which each contained their own distinct visual and tactile cues. During the second phase (conditioning, days 2-9), on alternate days mice were restricted to one side or the other of the apparatus for 30 min by use of a dividing door. Just prior to being placed in the chamber, each mouse was given an injection of either cocaine (20 mg/kg, i.p.) or saline (i.p.). The cocaine was paired with the side of the apparatus less preferred during the first phase of testing. Approximately half the mice were started on cocaine, while the other half were started on saline. During this time, the mouse's locomotor activity was measured by infrared sensors and used to determine cocaine-induced locomotor sensitization. The final phase of testing (post-conditioning, day 10) consisted of placing the mouse on the cocaine-paired side initially with the dividing door removed; however, no drug was given on this day. Thus mice were given full access to both compartments and their time spent on each side was measured. % CPP was calculated as the time spent on the cocaine-paired side between post-conditioning minus the time spent on the cocaine-paired side during pre-conditioning divided by the time spent on the saline-paired side during pre-conditioning. Only the first 20 minutes of pre-conditioning and post-conditioning was used in the calculation of % CPP. Locomotor sensitization to cocaine was determined by the ambulatory distance on days when mice received cocaine during the conditioning phase of CPP.

Morris Hidden Water Maze (HWM):

The water maze protocol here was modified from a protocol previously described (Vorhees, et al. (2006). Nat Protoc. 1(2):848-858). Mice were acclimated to the testing room for at least 10 minutes after which behavioral testing began. For the first 5 days, a platform was placed just under the water in the northeast corner of the maze such that mice could not see it. Each day for 4 trials per day, mice were placed into the pool facing the wall and were given 60 seconds to find and stand on the platform. If they found it, they were allowed to sit on it for 10 seconds before being removed. If they did not find the platform in the 60 seconds, they were placed on the platform by the experimenter for 20 seconds. After each trial, mice were allowed to dry in a clean cage on top of a warming pad, with at least 10 minutes in between each trial. On the final day of testing, the platform was removed. The mice were placed in the pool for a single trial and the time spent in each quadrant was measured. All analyses of behavioral performance on the water maze were made using ANY-maze software.

Tail Suspension Test (TST):

The tail suspension task involved taping a mouse by the tail to a force sensor connected to a computerized monitoring system. The force sensor measured the amount of time each mouse spent struggling to right itself. The mouse was taped to the sensor for 6 minutes. The last 4 minutes of the trial were used to calculate time immobile (i.e. not struggling). A single trial was performed for each mouse.

Rotarod:

The rotarod machine consisted of a rotating, grooved rubber cylinder (approx. 3 cm in diameter) with dividers so that multiple mice could be placed on the machine at once. Mice were placed on the cylinder, which rotated for five min gradually increasing from 4 rpm to 40 rpm. The amount of time spent on the cylinder before safely falling was recorded. Three trials were performed each day for 4 days, with 5 min in between trials.

Open Field (OF) Locomotion:

Following 20 minutes of acclimation to the testing room, mice were initially placed in open field chambers for 60 min and ambulatory distance was recorded. Mice were then removed from the chamber, injected with saline (i.p., equivalent to a 20 mg/kg dose of cocaine) and placed back in the chamber for 90 min. Finally, mice were removed again and injected with cocaine (20 mg/kg, i.p.) before being placed back in the chamber for an additional 120 minutes.

Bile Acid Determination:

Serum bile acids were measured by mass spectrometry via the Vanderbilt Mass Spectrometry Core facility.

Obeticholic Acid (OCA) Administration:

OCA/6-ECDCA (Adipogen, San Diego, Calif.) was initially dissolved in beta cyclodextrin (20% w/v) and then dissolved within palatable drug-laced jellies. Jellies were composed of gelatin (10% w/v), sucralose (18.5% w/v), artificial strawberry flavoring (8% v/v); beta cyclodextrin (2% w/v) in water. Jellies containing OCA were made to contain approximately 10 mg/kg based on each mouse's original weight. Jellies containing vehicle contained the same amount of beta cyclodextrin. Mice were given jellies by voluntary oral administration six days per week for four weeks. They were given the jellies between 3 pm and 6 pm by placing each mouse into an open field chamber containing the jelly. To ensure that mice consumed the jellies consistently, all mice were initially trained to eat jellies without drug for 5 days prior to drug/vehicle jelly administration. Mice in this group underwent behavioral testing for cocaine conditioned place preference after 2 weeks of chronic drug administration. During this time, drug administrations were continued until sacrifice.

Figure 27A:
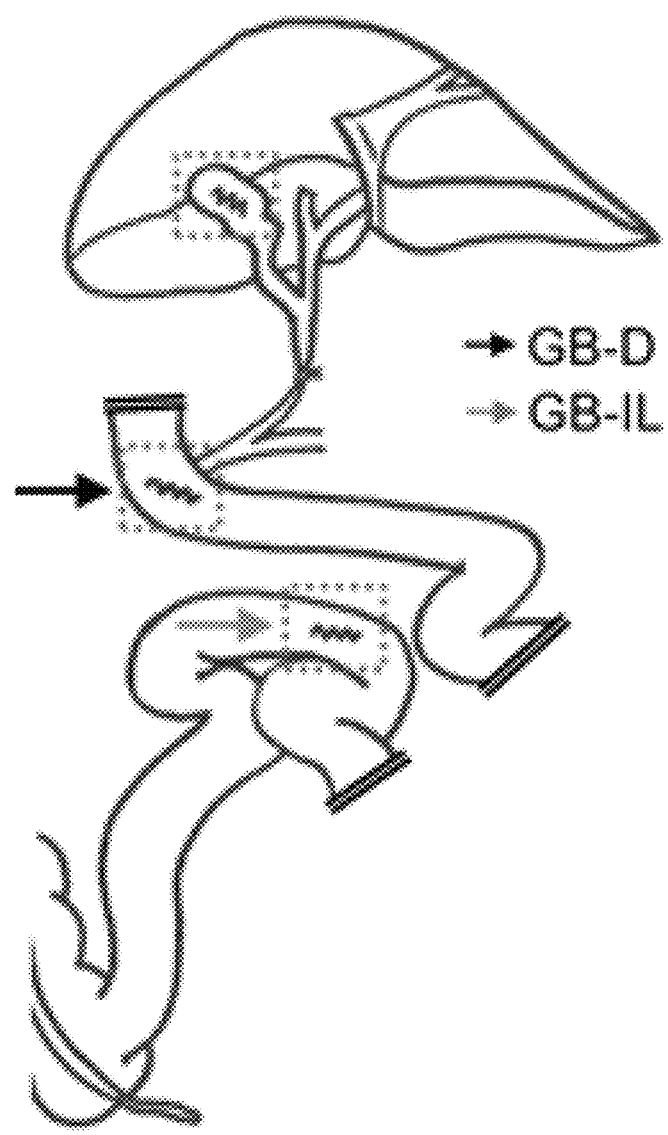
FIGS. 27A to 27F shows biliary diversion blocks cocaine's ability to increase DA levels in the NAc.

Example 4: Bariatric Surgery Controls Bile Acid Signaling and Impairs Cocaine Reward Results Traditionally, bile acids have been seen as simple detergents participating in the emulsification of ingested fats. However, it is increasingly apparent that bile acids also function as steroid hormones with targets in the intestine, liver, and brain (Kuipers, F., et al. Nature reviews. Endocrinology 10:488-498 (2014); Keitel, V., et al. Glia 58:1794-1805 (2010)). Bile acids produced from cholesterol in the liver enter the proximal small intestine at the duodenum and are taken back up into portal circulation at the distal ileum, a segment of the small intestine densely populated by bile acid receptors and reuptake transporters. Biliary diversion—a newly developed bariatric surgical procedure in mice—is capable of chronically elevating circulating bile acids through ligation of the common bile duct and anastomosis of the gallbladder to the ileum (FIG. 27A; GB45-IL) (Flynn, C. R., et al. Nature communications 6:7715 (2015)). In the control surgery, the gallbladder is anastomosed to the duodenum (FIG. 27A; GB-D), restoring normal bile flow independent of the sphincter of Oddi.

Biliary diversion was developed in mice to treat high fat diet-induced obesity (Flynn, C. R., et al. Nature communications 6:7715 (2015)). GB-IL mice exhibited reduced high fat food consumption and weight loss. This reduction in the intake of rewarding, calorically-dense food could stem at least in part from altered reward for palatable food. Dysregulated mesolimbic dopamine (DA) circuitry has been linked to high fat, high calorie food consumption as well as cocaine abuse (Hernandez, L., et al. Life Sci 42:1705-1712 (1988); Johnson, P. M. & Kenny, P. J. Nat Neurosci 13:635-641 (2010); Volkow, N. D., et al. Biol Psychiatry 73:811-818 (2013)). Indeed, psychostimulants such as cocaine hijack these circuits to cause addiction. It was thus hypothesized that bile diversion to the ileum, which reduces high fat intake and increases circulating bile acids (Flynn, C. R., et al. Nature communications 6:7715 (2015)), might also reduce the rewarding properties of cocaine.

Figure 27B:
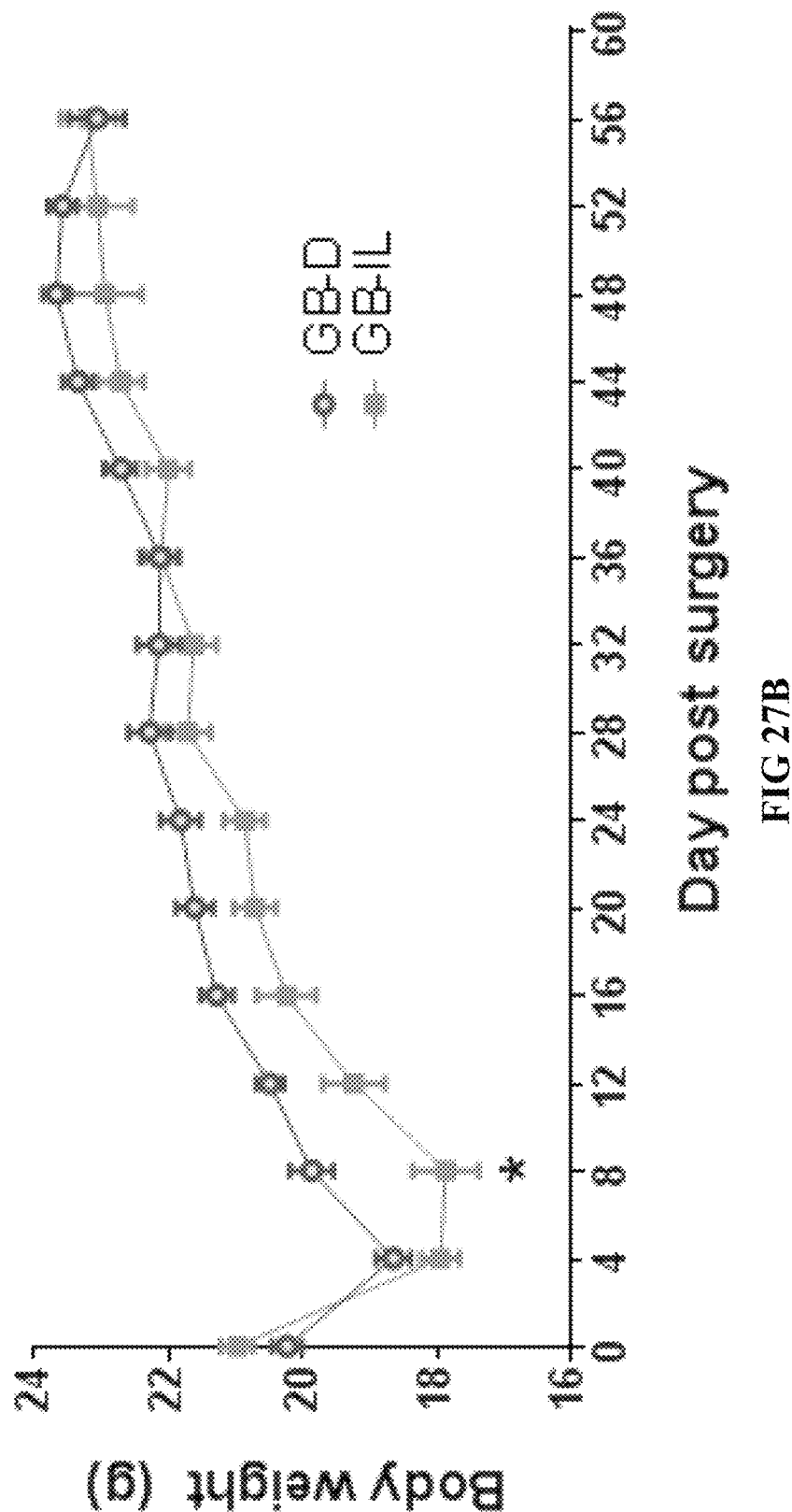
Figure 27C:
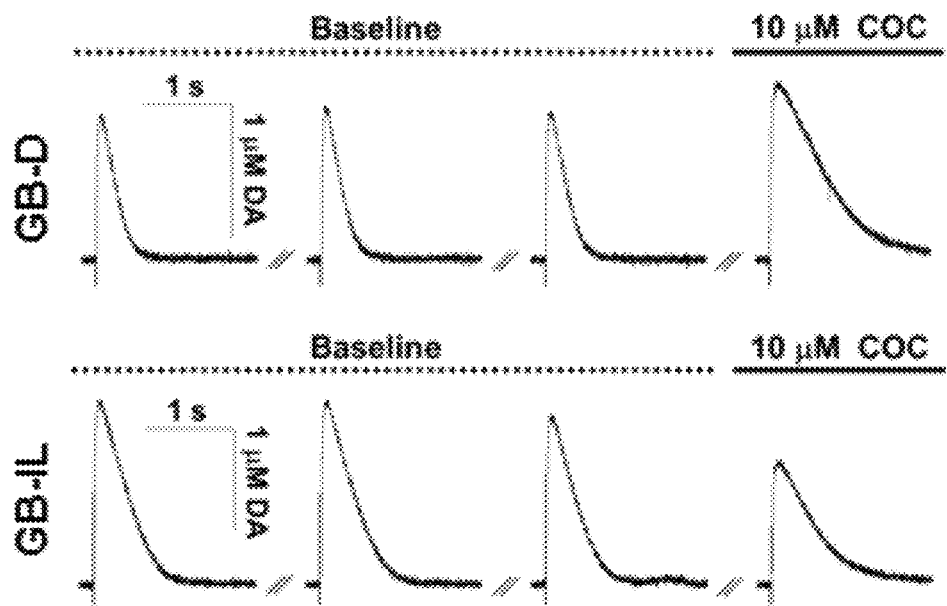
Figure 27D:
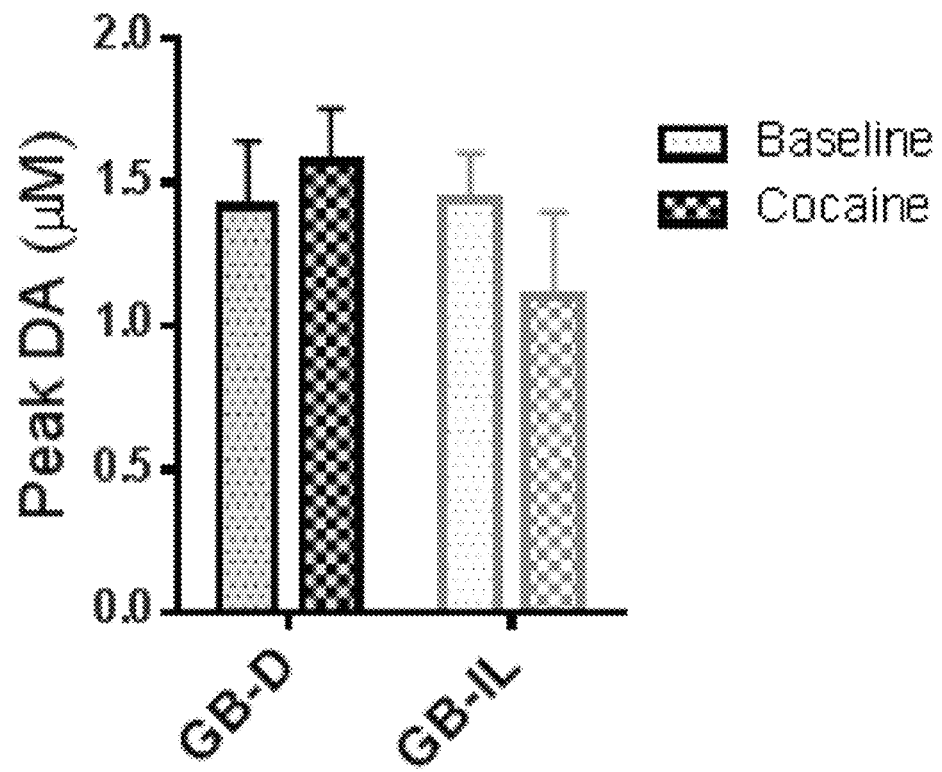
Figure 27E:
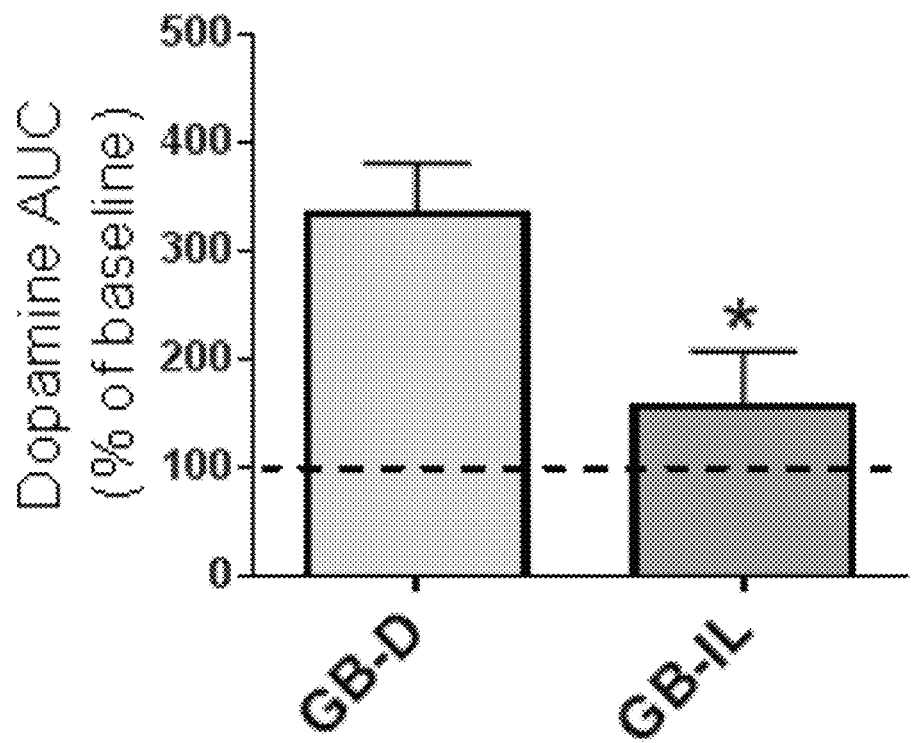
Figure 27F:
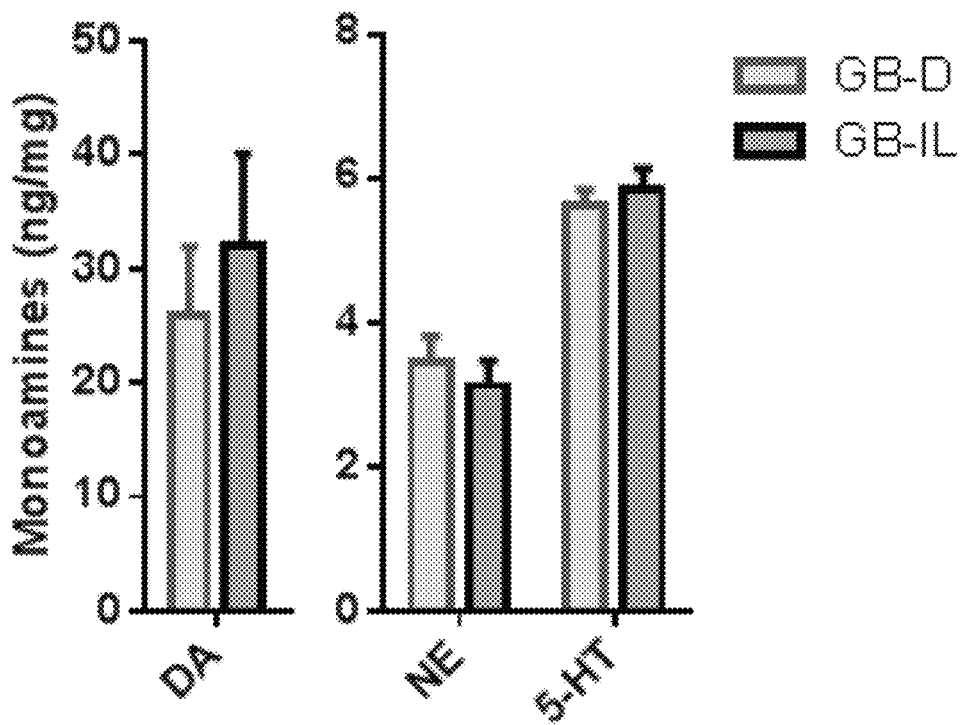

Cocaine directly alters DA neurotransmission and produces its rewarding effects by increasing available extracellular DA in specific brain regions, including the nucleus accumbens NAc) (Hernandez, L., et al. Life Sci 42:1705-1712 (1988); Roberts, D. C. S. & Koob, G. F. Pharmacology, Biochemistry, and Behavior 17:901-904 (1982)). The effect of the surgery was first studied on cocaine's ability to enhance DA availability in NAc. Experiments were performed in animals fed a chow diet. In GB-IL mice, there were no significant differences in body weight as compared to GB-D as early as day 12 post-surgery (FIG. 27B). This strongly suggests that, on a regular chow diet, the long-term homeostatic regulation of body weight in GB-IL parallels that of the GB-D mice. Here, the effect of cocaine on electrically-evoked DA release was measured in NAc slices. Three stable baseline recordings were taken at five minute stimulation intervals for GB-D (FIG. 27C, baseline) and GB-IL (FIG. 27C, baseline) mice. The increase in electrically-evoked DA release promoted by 10 μM cocaine for GB-D and GB-IL mice is shown in FIG. 27C (cocaine). Quantitation of the peak of the amperometric currents, under baseline or cocaine conditions (FIG. 27D) demonstrates no significant difference between GB-D and GB-IL mice. However, quantitation of the area under the curve (AUC) of the amperometric traces in the presence of cocaine (FIG. 27E) clearly demonstrates that GB-IL mice are resistant to the ability of cocaine to increase accumbal DA. Importantly, GB-IL mice do not exhibit an overt neurochemical phenotype, as total accumbal issue levels of DA and its related monoamines, norepinephrine (NE) and serotonin (5-HT), were not significantly altered with respect to GB-D (FIG. 27F).

Figure 28A:
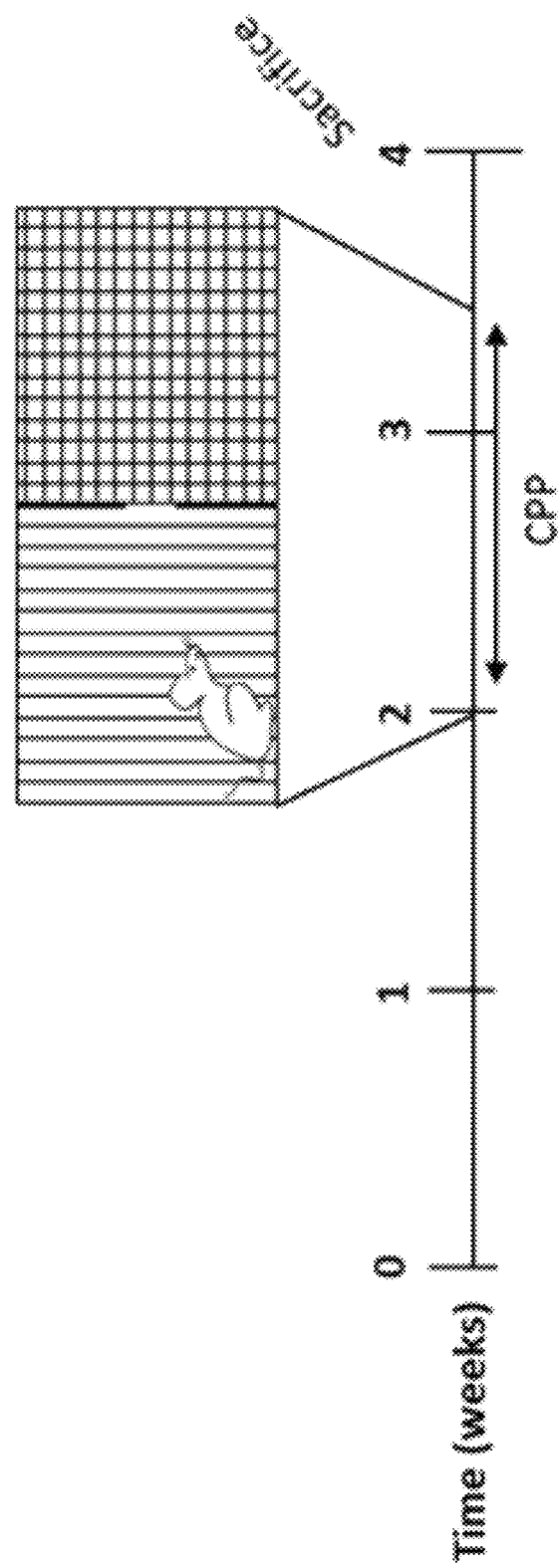
Figure 28B:
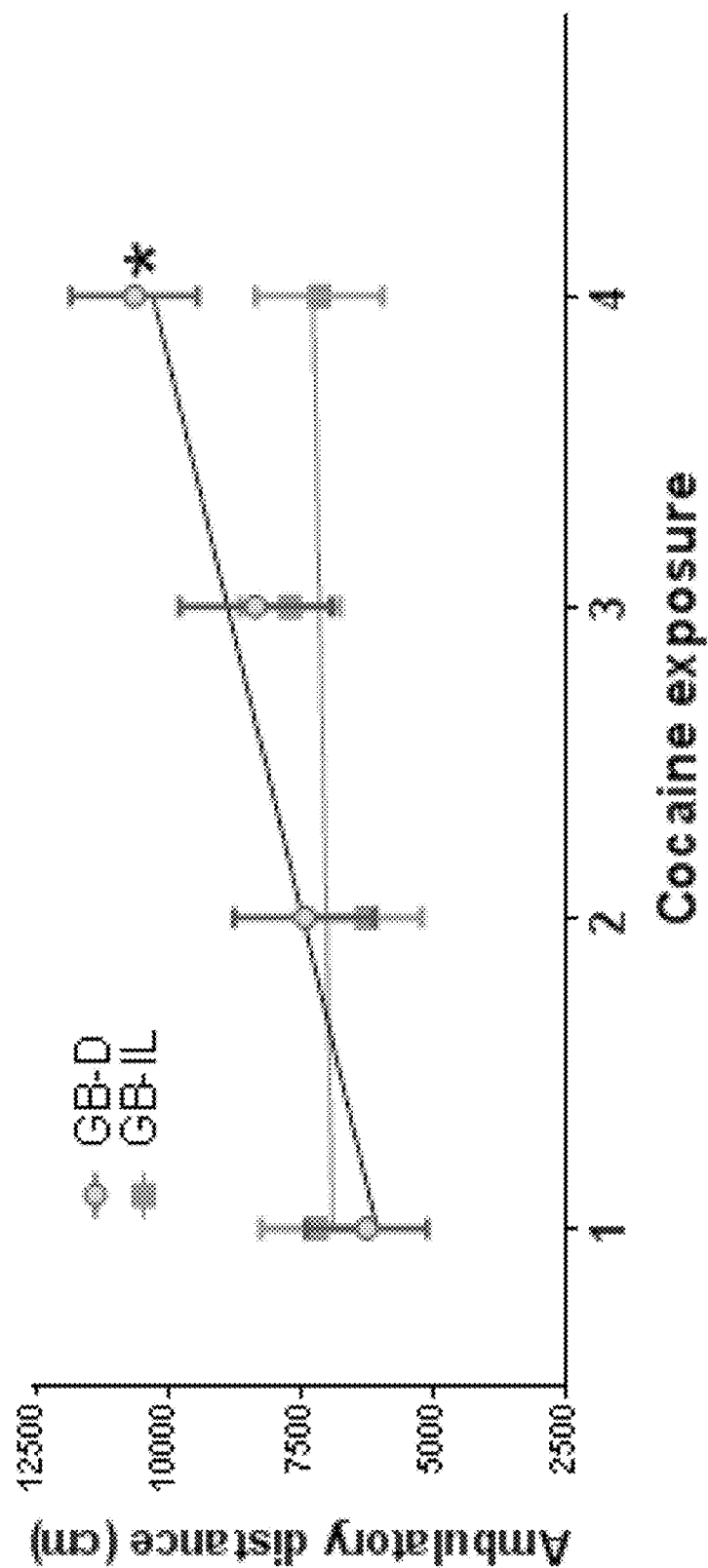
Figure 28D:
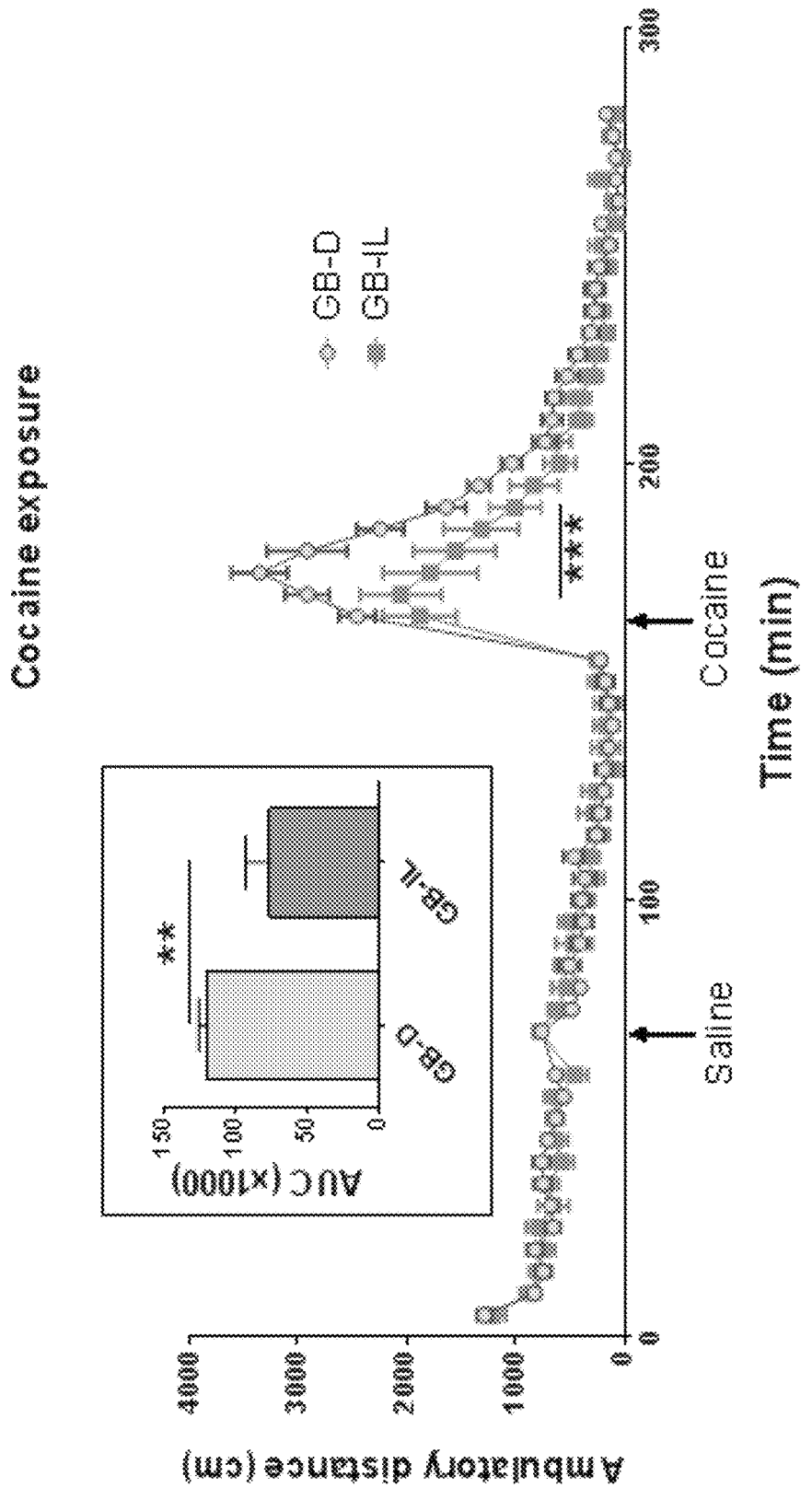
Figure 29A:
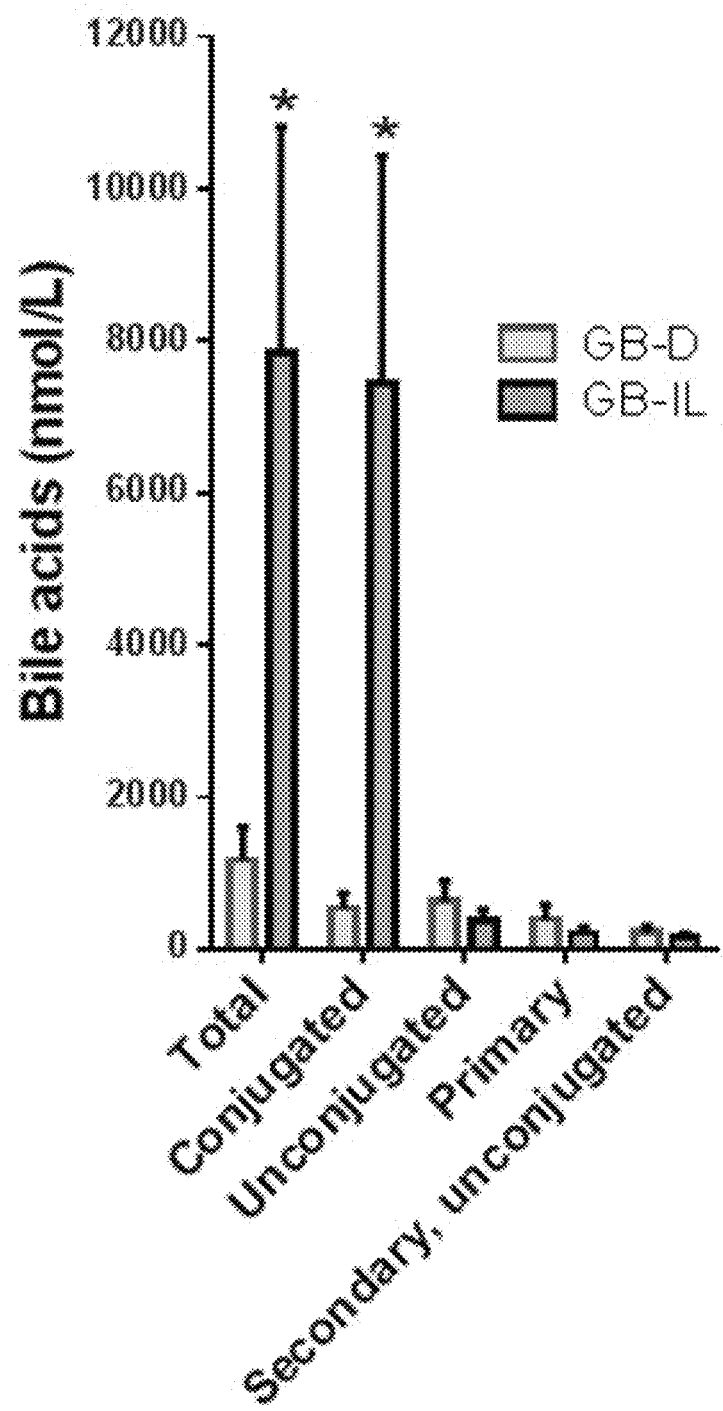
FIGS. 29A to 29E show bile acid signaling regulates cocaine reward.
Figure 29B:
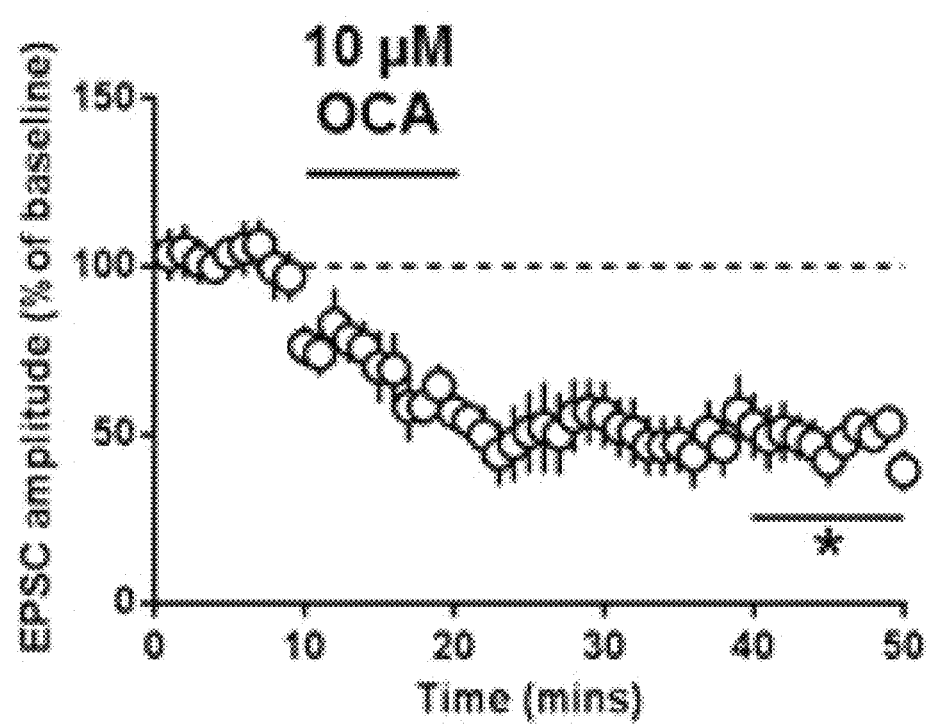
Figure 29C:
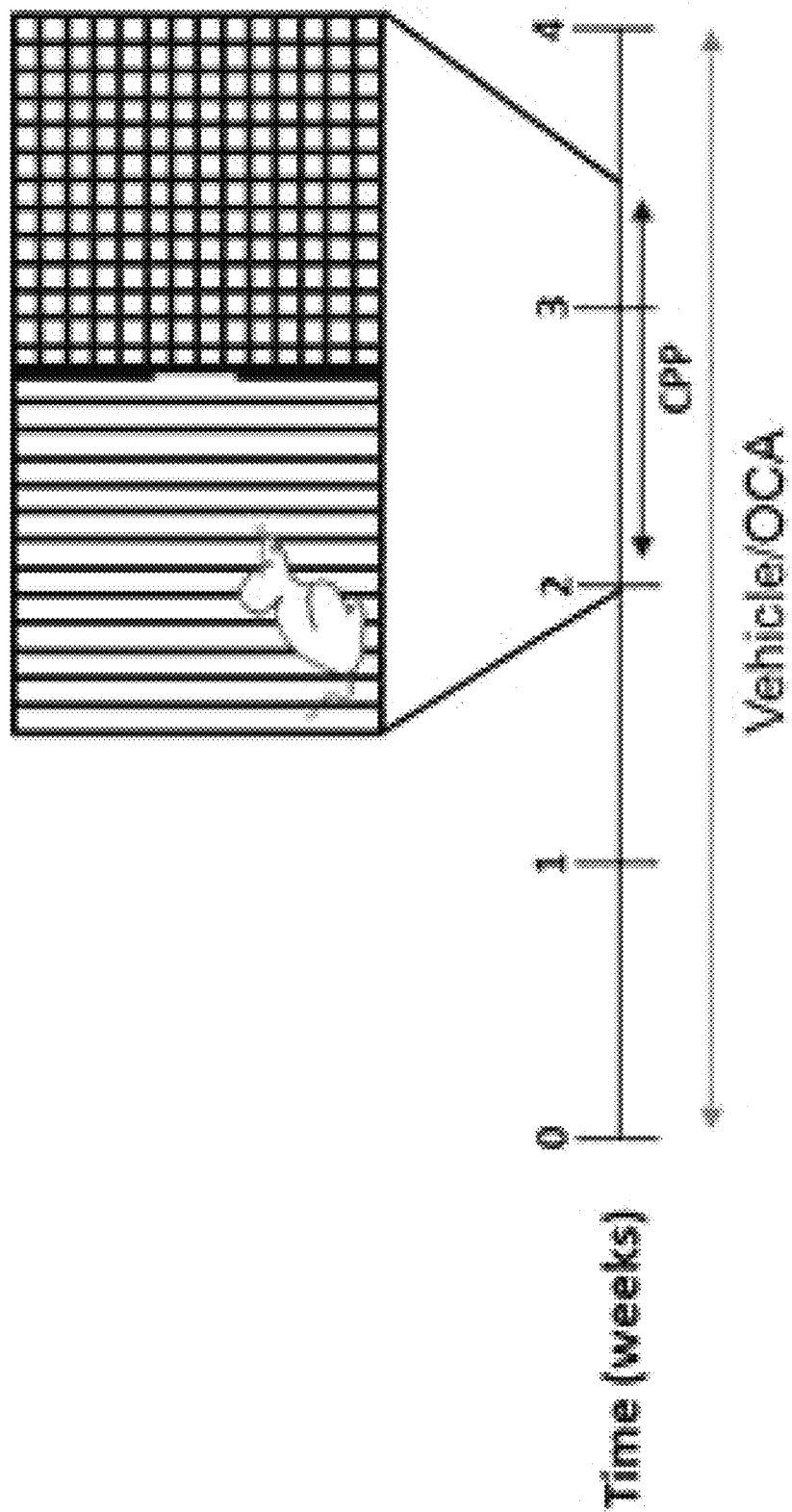
Figure 29D:
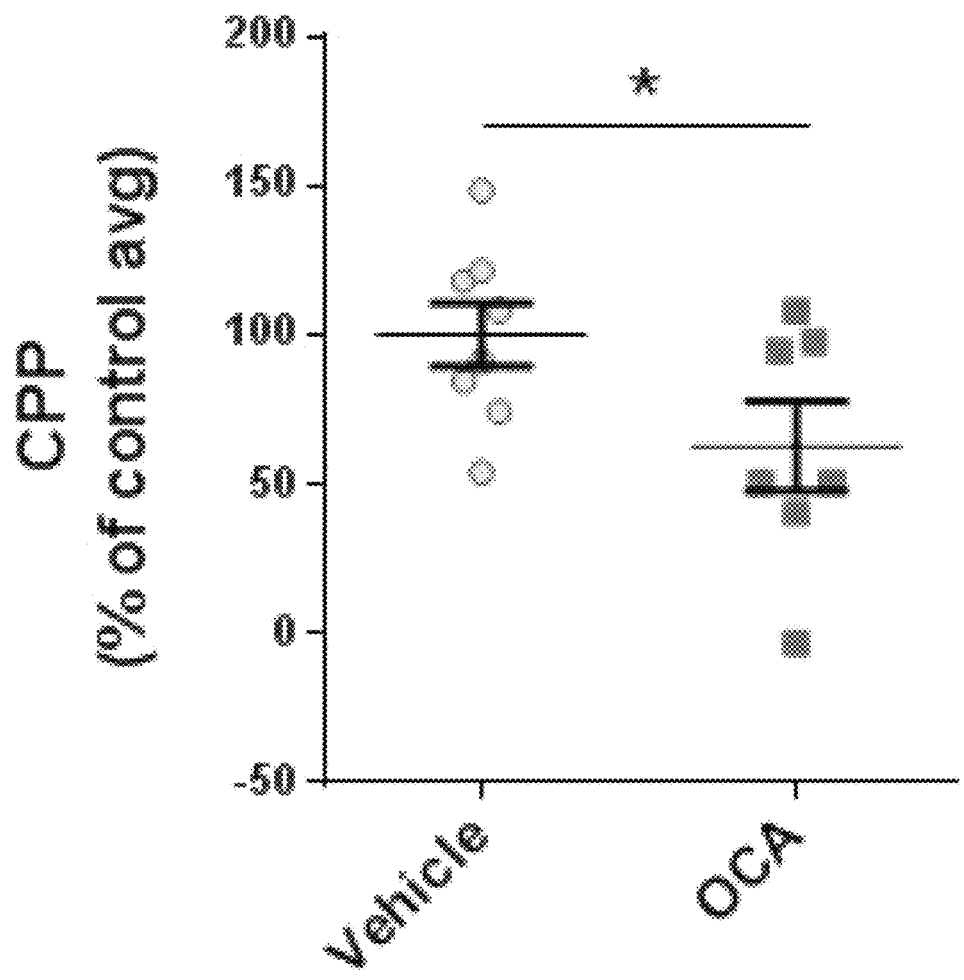
Figure 29E:
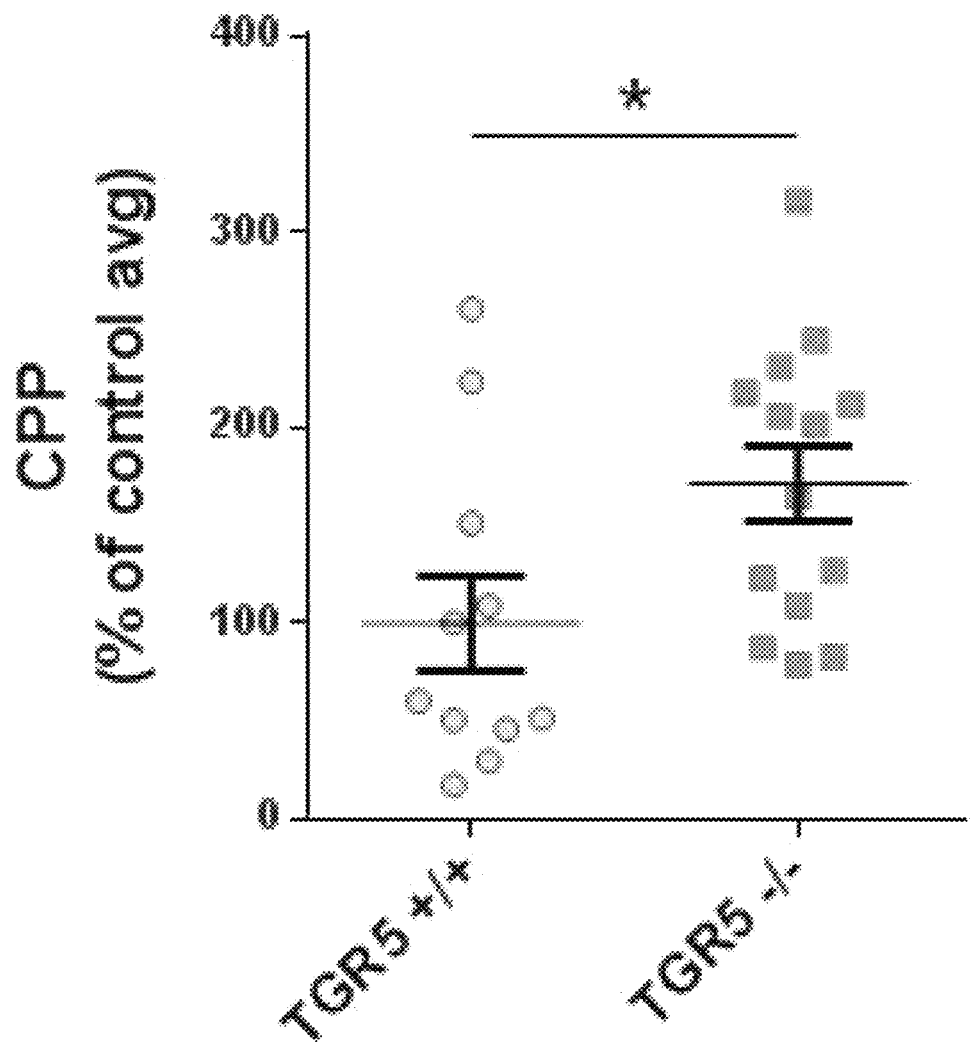
Figure 30:
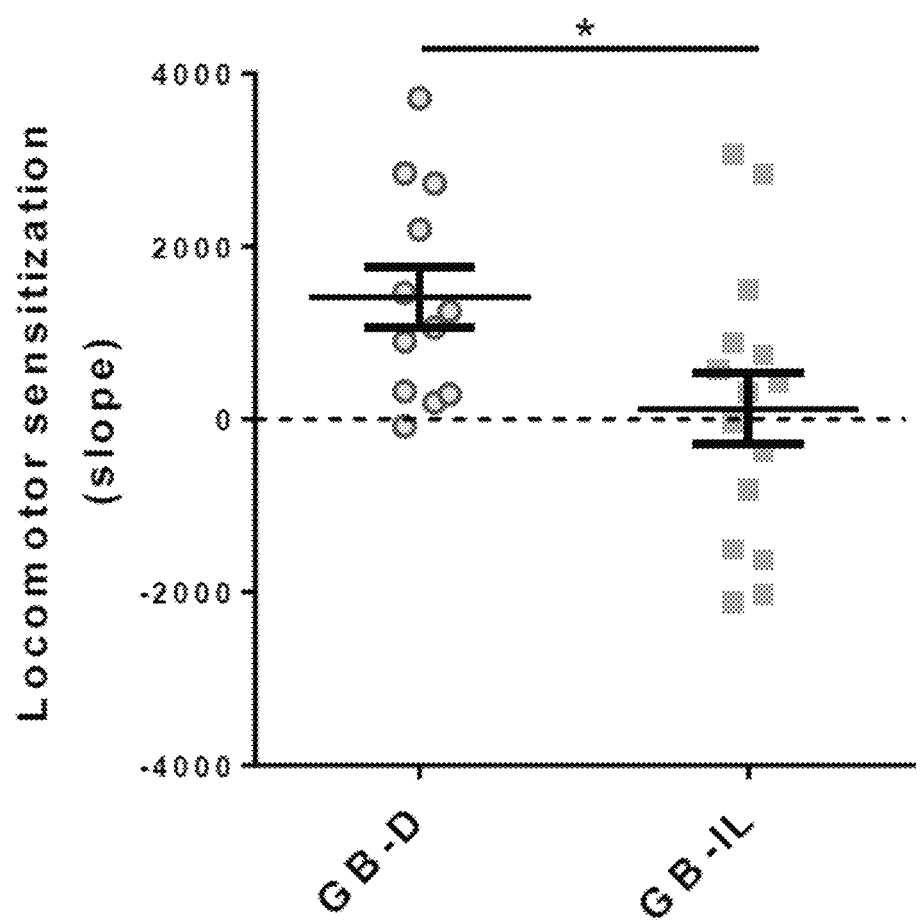
FIG. 30 shows biliary diversion reduces locomotor sensitization to cocaine. Each dot indicates the slope of the linear regression of the ambulatory distance induced by the four cocaine exposures in each individual mouse (n=12-15; *p<0.05 by Student's t test).

It was next determined whether GB-IL mice display reduced behavioral responses to cocaine. Mice were tested for cocaine conditioned place preference (CPP; 20 mg/kg, i.p.) in a dual compartment apparatus (FIG. 28A). During conditioning sessions, locomotor behavior was measured. On first exposure to cocaine, cocaine-induced hyperlocomotion was indistinguishable between the two groups, suggesting that GB-D and GB-IL mice experienced similar levels of cocaine centrally. Notably, while control mice exhibited significant locomotor sensitization to cocaine over multiple exposures (*$p<0.05$), the GB-IL mice did not (FIG. 28B, 30). Prior work strongly suggests that psychomotor sensitization is associated with the development of molecular adaptations within the mesocorticolimbic system in the development of an addiction (Robinson, T. E. & Berridge, K. C. Philos Trans R Soc Lond B Biol Sci 363:3137-3146 (2008)). The lack of locomotor sensitization in the biliary diversion model may thus support impairments in the central encoding of cocaine reward. Importantly, while both groups formed a place preference for cocaine, the preference of GB-IL mice for the cocaine-paired side was significantly less than that observed for GB-D mice (FIG. 28C). In an open field, neither spontaneous nor saline-induced locomotion in GB-IL mice significantly differed from GB-D mice; however cocaine-induced locomotion (20 mg/kg, i.p.) was significantly attenuated between 10 and 30 minutes post-injection (FIG. 28D and inset).

Figure 31A:
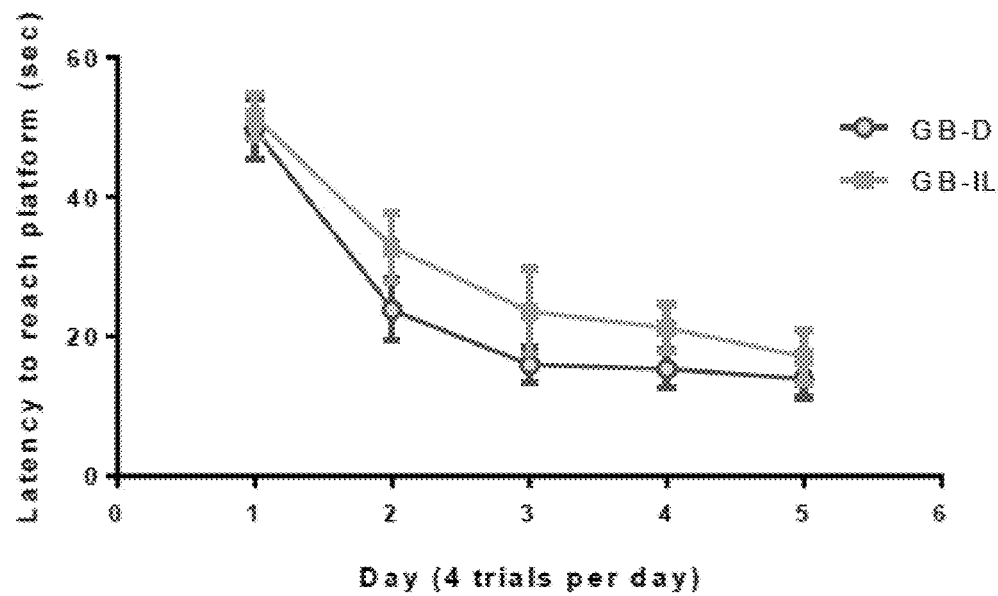
FIGS. 31A to 31F show biliary diversion does not alter learning, memory, motor function, or affective behavior.
Figure 31B:
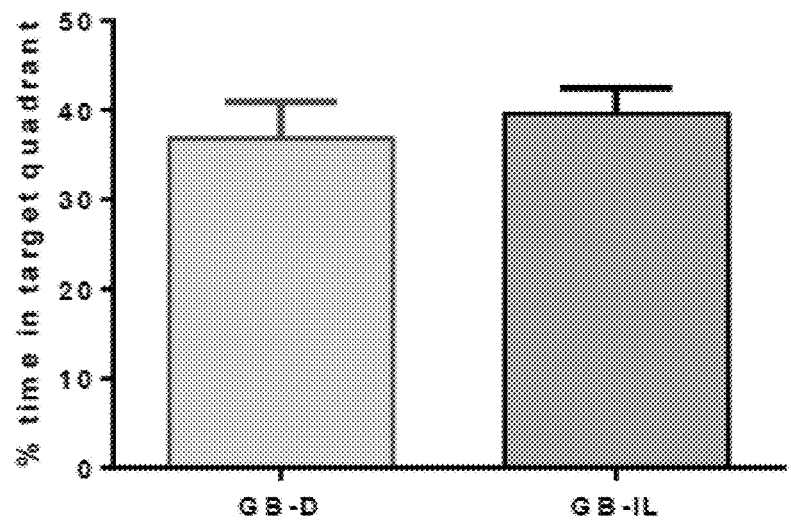
Figure 31C:
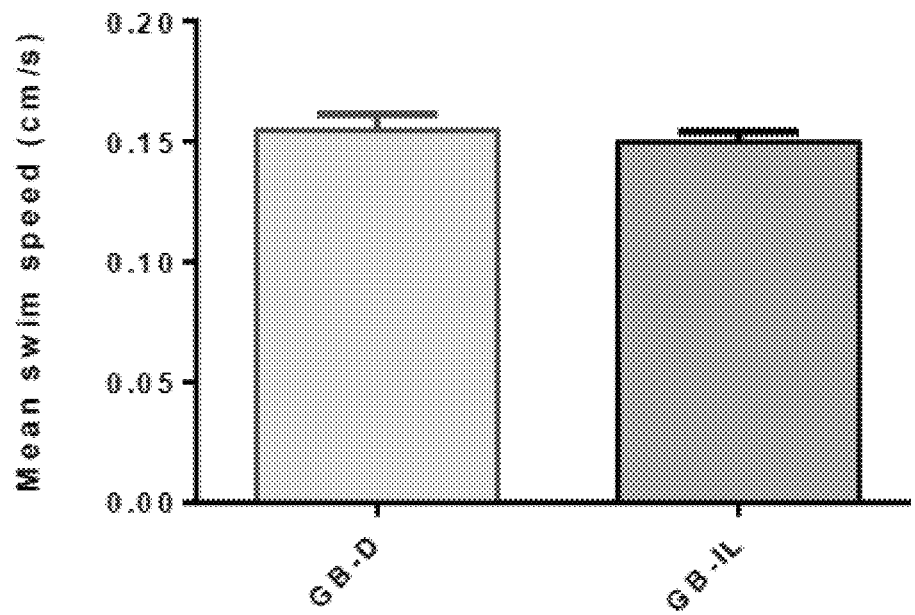
Figure 31D:
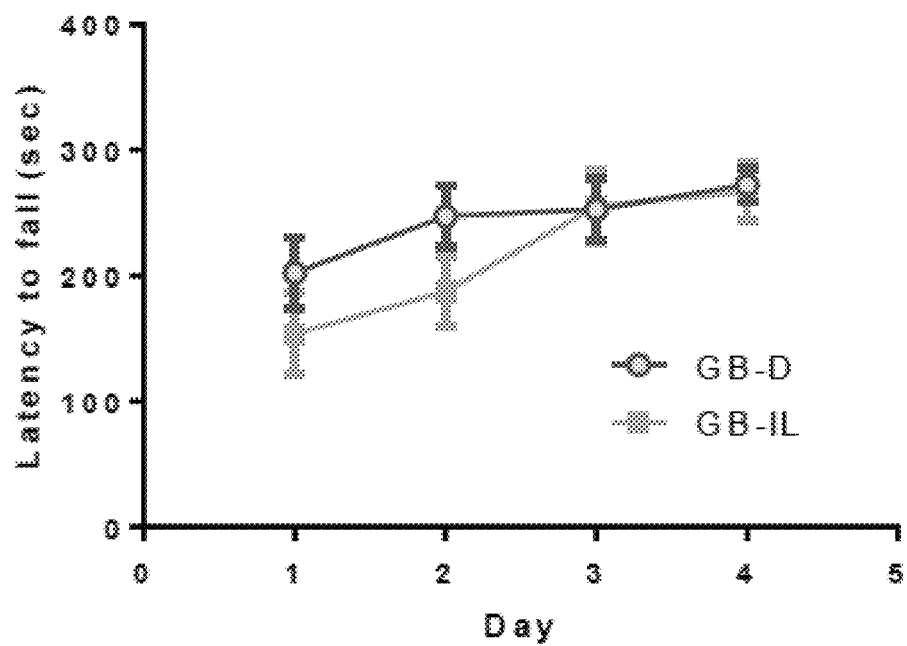
Figure 31E:
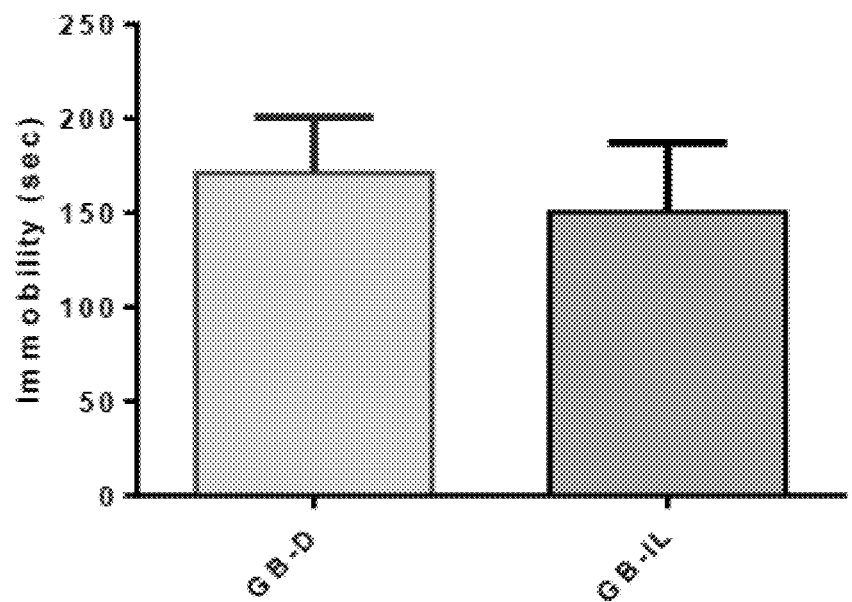
Figure 31F:
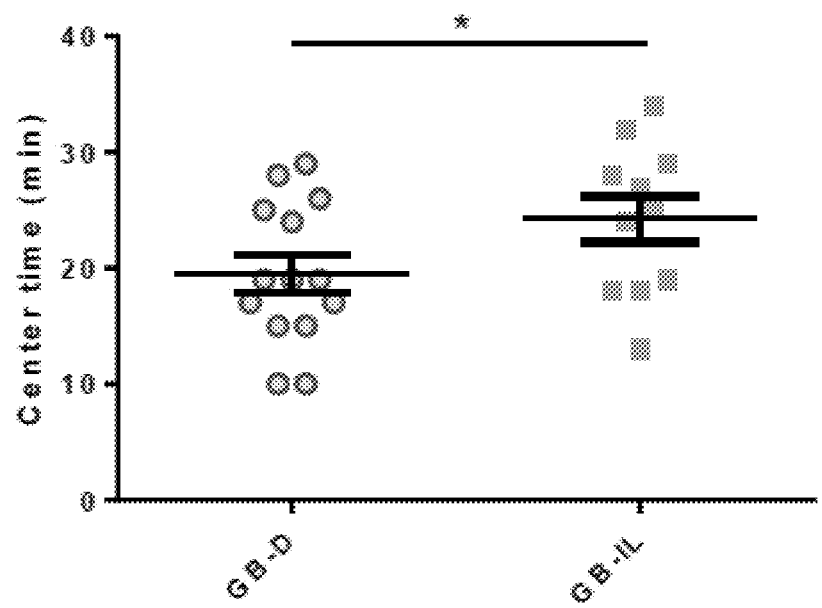

The reduction in conditioning to cocaine cannot be attributed to impaired spatial learning or memory capabilities, as there was no significant impairment in performance on a hidden water maze task (FIG. 31A-C). Moreover, no generalized impairments in abilities (FIG. 31D) or motivated behavior/affective state in a tail suspension test (FIG. 31E) were observed. However, in the open field, there was a small but significant increase in center time in the GB-IL group (FIG. 31F), suggesting that the surgery may also affect systems regulating exploratory behavior or anxiety.

GB-IL mice exhibit greatly increased levels of total and conjugated circulating bile acids relative to GB-D, while levels of primary, secondary, and unconjugated bile acids remain unchanged (FIG. 32A). This finding, in conjunction with behavioral data, points to a potent and previously unexplored role for conjugated bile acids as regulators of cocaine reward. However, whether bile acids signal directly within the brain was unknown. Prior work suggests that AMPA receptor signaling in the NAc participates in molecular mechanisms underlying cocaine-seeking behavior (Wolf, M. E. & Ferrario, C. R. Neurosci Biobehav Rev 35:185-211 (2010); Grueter, B. A., et al. Curr Opin Neurobiol 22:545-551 (2012)). As disclosed herein, the synthetic bile acid obeticholic acid (OCA) induces a robust depression of AMPA receptor-mediated excitatory post-synaptic currents (EPSCs) in the NAc (FIG. 32B). This result indicates that bile acid signaling acutely regulates excitatory neurotransmission in the NAc, an important component of the development of reward-context associations in the CPP test (Grueter, B. A., et al. Curr Opin Neurobiol 22:545-551

Figure 32:
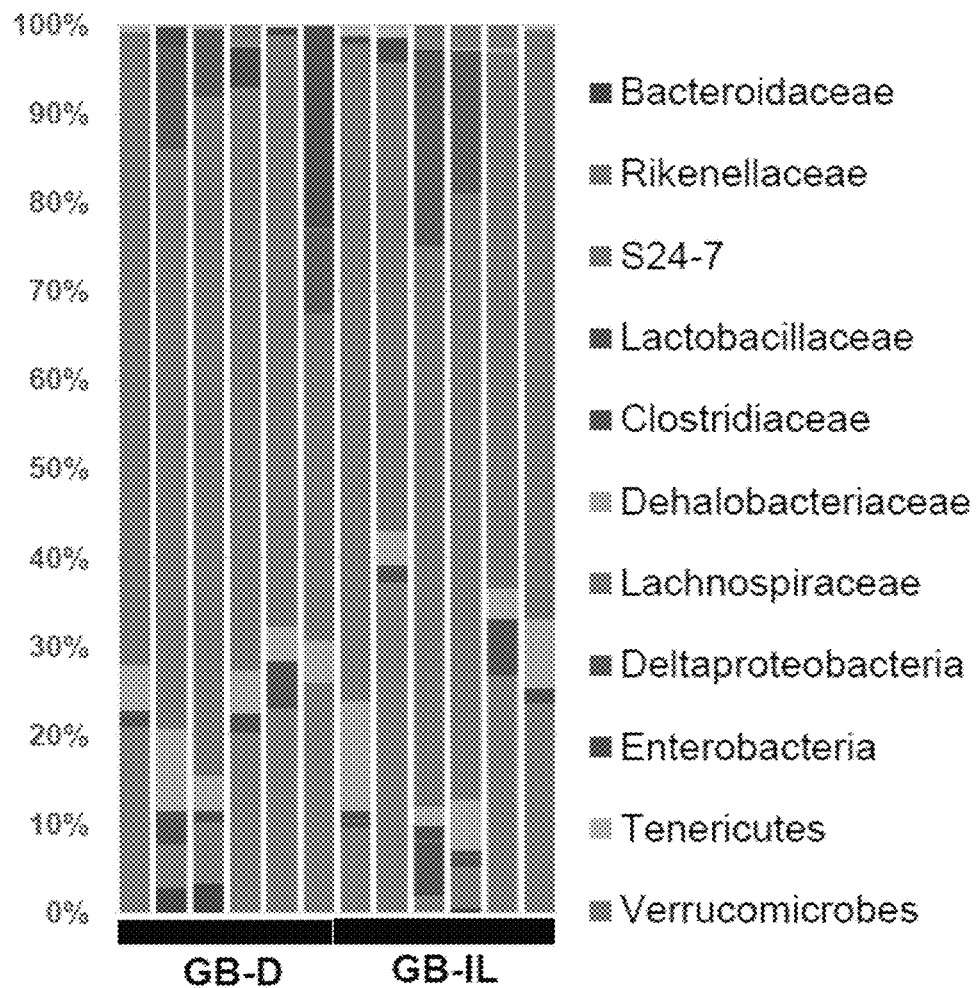
FIG. 32 shows GB-IL mice do not exhibit altered gut microbiota compared to GB-D controls. Stacked column bar graph depicting the relative abundances and distributions of the most highly abundant resolved bacterial phyla across the 12 fecal samples analyzed. Cecal contents from mice subject to GB-D (n=6) or GB-IL (n=6) were subjected to 16S RNA sequencing. Bacteroidetes are colored in shades of red, proteobacteria in shades of blue, tenericutes in purple and verrucomicrobes in pink. Each column represents a single mouse. No significant differences in bacterial abundances were noted by a Student's t test comparison of each bacterial phylum comparing grouped GB-D and GB-IL averages (p>0.05).

(2012); Calipari, E. S., et al. Proc Natl Acad Sci USA 113(10):2726-31 (2016)). Using an in vivo pharmacologic model, chronic OCA administration was shown to be sufficient to reduce cocaine CPP (FIG. 32). For two weeks prior to the initiation of cocaine CPP, mice were treated with OCA (10 mg/kg, p.o.) or vehicle (FIG. 32C). The treatment continued until sacrifice 4 weeks following drug initiation. Mice treated with OCA, compared with vehicle treatment, exhibited decreased cocaine CPP (FIG. 32D).

In addition to their canonical role as fat emulsifiers, bile acids signal in a hormonal fashion mainly through two bile acid receptors, the farnesoid x receptor (FXR) and g protein coupled bile acid receptor 1 (TGR5) (Fiorucci, S., et al. Trends in pharmacological sciences 30:570-580 (2009)); only TGR5 is expressed in the brain (Keitel, V., et al. Glia 58:1794-1805 (2010); Maruyama, T., et al. J Endocrinol 191:197-205 (2006)). To test whether TGR5 receptor signaling contributes to reduced susceptibility to the rewarding properties of cocaine, we measured cocaine CPP in TGR5 knockout mice. We found that deletion of the TGR5 receptor results in significantly increased preference for the cocaine-paired chamber relative to wild-type littermates (FIG. 32E). This enhancement in cocaine reward identifies a role for the TGR5 receptor in reward processes and supports basal signaling through TGR5 as a contributor to resilience to cocaine reward.

These findings support a pivotal role for bile acid signaling in neuronal function as well as in reward behaviors. This was first revealed by a new surgery where bile acids were diverted to the ileum to increase reabsorption and augment levels of circulating bile acids. This surgery was able to modify reward acquisition for cocaine. GB-IL blocks both sensitization and the rewarding properties of cocaine, which relies on increases in extracellular DA levels. Notably, the surgery alters cocaine's ability to increase DA levels in the NAc. These results thus reveal that a surgery designed for weight loss also regulates psychostimulant reward. Bile acid signaling is also shown to be important to this process. This notion is supported by the finding that chronic OCA treatment impairs cocaine reward. Conversely, TGR5 knockout mice exhibit enhanced cocaine preference compared to their wild-type counterparts. Together, these results point to a role for bile acid signaling in susceptibility or resilience to cocaine reward. Of note, no differences in the gut microbiome composition was detected in the surgical model (FIG. 32), suggesting that potential alterations to the gut microflora are unlikely to mediate altered gut-to-brain communication in this setting.

Interestingly, both dopaminergic and glutamatergic systems in the NAc appear to be affected by alterations in bile acid signaling as we were able to alter cocaine-induced increases in extracellular DA in the surgical model and acutely induce a long-lasting depression of EPSCs pharmacologically. Notably, both of these actions contribute to the rewarding and reinforcing effects of cocaine (Joffe, M. E., et al. Cognitive science 5:151-171 (2014)). Importantly, the bile acid receptor agonist used in the current study (OCA) has already completed a phase III clinical trial to treat hepatic steatosis (Fiorucci, S., et al. Mini reviews in medicinal chemistry 11:753-762 (2011)). This drug showed clinical efficacy in this setting with an excellent safety profile, thereby reducing barriers to its development for addiction.

Methods:

Mice:

Male wild-type C57BL/6J mice used for surgeries or for OCA treatment were acquired from Jackson Laboratories (Bar Harbor, Me.) at 5 weeks of age. Mice were acclimated to a Vanderbilt University housing facility for one week prior to surgery. Surgery (GB-D or GB-IL) occurred at 6 weeks of age. Mice were given at least 2 weeks to recover from surgery and were handled for 3 days prior to the start of the CPP paradigm. At this point, mice either underwent behavioral testing (beginning with CPP) or were sensitized to cocaine without behavioral testing. Mice from the surgical model were sacrificed at either 4-5 or 7-8 weeks post-surgery. Gpbar1 (TGR5) knockout heterozygous breeder mice were obtained from Dr. David Wasserman at the Vanderbilt University School of Medicine and their generation is described in Vassileva, G., et al. Biochem J 398:423-430 (2006). Permission to use the Gpbar1 knockout mouse line was generously provided by Merck & Co. (Kenilworth, N.J., USA). These mice were maintained on a C57BL/6J background. Heterozygous mice were mated to generate male and female knockout mice and wild-type mice used in behavioral experiments. These mice were handled for 3 days prior to the start of the CPP paradigm, which began at 8 weeks of age. All mice were group housed (at least 2 mice per cage) at a Vanderbilt University housing facility with ad libitum access to standard chow and water. The temperature- and humidity-controlled facility is maintained on a 12:12 h light:dark cycle (lights on 07:00-19:00 h) and all experiments were performed during the light phase. All protocols were approved by the Vanderbilt University Institutional Animal Care and Use Committee.

Surgery:

The control surgery (GB-D) and experimental surgery (GB-IL) were performed as previously described (Keitel, V., et al. Glia 58:1794-1805 (2010)). Body weights were measured immediately prior to surgery and following surgery up until sacrifice. Body weights for each mouse were averaged within 4 day bins and are represented as such in the group averages.

Amperometry in Ex Vivo Slice Preparation:

Following recovery from surgery as described above, GB-D and GB-IL mice were treated with saline or cocaine along the same schedule as used for cocaine CPP using 20 mg/kg cocaine (see below; briefly, i.p. injections of saline every other day for 8 days and injections of cocaine on alternate days). After each injection, mice were placed back in their home cages. Mice were sacrificed by rapid decapitation under isoflurane anesthesia 1-2 days following their final cocaine injection. Slices were prepared as previously described (Robertson, S. D., et al. J Neurosci 30:11305-11316 (2010)) and electrically-evoked DA release in the NAc was measured by standard methods (Schmitz, Y., et al. J Neurosci 22:8002-8009 (2002)). DA release was stimulated with a bipolar electrode placed on the surface of the slice and recorded with a carbon fiber electrode.

High Performance Liquid Chromatography:

Mice were sacrificed by rapid decapitation under isoflurane anesthesia at 4-5 weeks following GB-D or GB-IL surgery. The brain was quickly dissected, blocked, and the NAc was punched bilaterally. Punches were placed into Eppendorf tubes on dry ice and stored at −80° C. until processing. HPLC to measure monoamines from tissue was performed as previously described (Reddy, I. A., et al. ACS chemical neuroscience 5:943-951 (2014)).

CPP and Locomotor Sensitization:

CPP was performed as previously described, with modifications (Graham, D. L., et al. Mol Psychiatry 18:961-962 (2013)). Briefly, 2-chamber CPP apparati (MED-CPP2-MS; Med Associates, St. Albans, Vt.) with distinct rod and mesh floor inserts were used. The associated software allowed for automated measurement of beam breaks on X-Y-Z axes (16 infrared beams, 50 ms intervals). Mice were weighed and then acclimated to the testing room for 20 min prior to testing each day. During the first phase (pre-conditioning, day 1), mice were placed on the grid floor side of the 2 chamber apparatus. For 30 min, the mice had free access to both sides of the apparatus. During the second phase (conditioning, days 2-9), on alternate days mice were restricted to one side or the other of the apparatus for 30 min by use of a dividing door. Just prior to being placed in the chamber, each mouse was given an injection of either cocaine (20 mg/kg, i.p.) or saline (i.p.). Cocaine was paired with the side of the apparatus less preferred during pre-conditioning. Approximately half of the mice were started on cocaine, while the other half were started on saline. During this time, each mouse's locomotor activity was measured and used to determine cocaine-induced locomotor sensitization. The final phase of CPP (post-conditioning, day 10) consisted of placing the mouse on the cocaine-paired side initially with the dividing door removed; however, no drug was given on this day. Thus, mice were given full access to both compartments and their time spent on each side was measured. % CPP was calculated as the time spent on the cocaine-paired side during post-conditioning minus the time spent on the cocaine-paired side during pre-conditioning divided by the time spent on the saline-paired side during pre-conditioning. The first 20 min of pre-conditioning and post-conditioning were used in the calculation of % CPP. Locomotor sensitization to cocaine was determined by the ambulatory distance on days when mice received cocaine during the conditioning phase of CPP (4 exposures). All CPP was performed during the first phase of the light cycle. Activity Monitor v5.10 (MED Associates) was used to analyze CPP activity.

Open Field (OF) Locomotion:

4-7 days following CPP, GB-D and GB-IL mice from selected cohorts were tested for OF locomotion. Mice were initially weighed. Following 20 min of acclimation to the testing room, mice were placed in clean automated OF chambers (28×28 cm; MED-OFA-510; MED Associates) under constant illumination for 60 min and ambulatory distance was recorded. Time spent in the center of the chamber relative to the outer edges was calculated using the default center-surround analysis in the accompanying software. Mice were then removed from the chamber, injected with saline (i.p., equivalent to a 20 mg/kg dose of cocaine) and placed back in the chamber for 90 min. Finally, mice were removed again and injected with cocaine (20 mg/kg, i.p.) before being placed back in the chamber for an additional 120 min. Activity Monitor v5.10 (MED Associates) was used to analyze OF activity. AUC was calculated from the cocaine phase of testing.

Morris Hidden Water Maze (HWM):

Following CPP and OF locomotion, GB-D and GB-IL mice from selected cohorts were tested on the HWM. The water maze protocol here was modified from a protocol previously described (Vorhees, C. V. & Williams, M. T. Nature protocols 1:848-858 (2006)). A round tub measuring 92×92 cm was filled with clean water the day before the first day of behavioral testing. On each morning of testing, mice were acclimated to the testing room for at least 10 min after which behavioral testing began. For the first 5 days, a platform was placed just under the water in the northeast corner of the maze such that mice could not see it. Each day for 4 trials per day, mice were placed into the pool facing the wall and were given 60 seconds to find and stand on the platform. If they found it, they were allowed to stand on it for 10 seconds before being removed by the experimenter. If they did not find the platform in the 60 seconds, they were placed on the platform by the experimenter for 20 seconds. After each trial, mice were allowed to dry in a clean cage on top of a warming pad, with at least 10 min in between each trial. On the final day of testing, the platform was removed. The mice were placed in the pool for a single trial and % time in the target quadrant was measured. All sessions were recorded by video and analyses of behavioral performance on the water maze were made using ANY-maze software (Stoelting Co., Wood Dale, Ill.).

Tail Suspension Test (TST):

Following CPP and OF locomotion, GB-D and GB-IL mice from selected cohorts were tested on the TST. This involved individually suspending each mouse by the tail using adhesive tape to a flat, stainless steel force sensor connected to a computerized monitoring system (v3.30, MED Associates). The force sensor measured the amount of time each mouse spent struggling to right itself. The mouse was suspended from the sensor for a total 6 min. The last 4 min of the trial were used to calculate time immobile, which was defined as the total time during which the mouse movement did not exceed a preset threshold of seven for 200 ms. A single trial was performed for each mouse.

Rotarod:

Following CPP and OF locomotion, GB-D and GB-IL mice from selected cohorts were tested on the rotarod. The rotarod consisted of a rotating, grooved rubber cylinder (approx. 3 cm in diameter) with dividers so that multiple mice could be placed on the machine at once. Mice were placed on the cylinder, which rotated for 5 min gradually increasing from 4 to 40 rpm. The amount of time spent on the cylinder before safely falling was recorded. Three trials were performed each day for 4 days, with 5 min in between trials.

Bile Acid Determination:

Serum bile acids were measured by mass spectrometry via the Vanderbilt Mass Spectrometry Core facility using methods previously described. 3 Bile acids were measured from trunk blood taken immediately 257 following decapition at sacrifice at 4-5 weeks and 7-8 weeks post-surgery.

OCA Administration:

To allow for gut bioavailability of OCA without the stress of oral gavage, OCA was administered to mice by voluntary oral administration. 22 OCA (Adipogen, San Diego, Calif.) was initially dissolved in beta cyclodextrin (20% w/v) and then dissolved within palatable drug-laced jellies. Jellies were composed of gelatin (10% w/v), sucralose (18.5% w/v), artificial strawberry flavoring (8% v/v); beta cyclodextrin (2% w/v) in water. Jellies containing OCA were made to contain 10 mg/kg based on each mouse's original weight on the first day of drug or vehicle administration. Jellies containing vehicle were identical to drug-laced jellies except that they contained beta cyclodextrin without dissolved drug. Mice were given jellies by voluntary oral administration on six consecutive days per week for 4 weeks. They were given the jellies between 3 pm and 6 pm by placing each mouse into an OF chamber containing the jelly for 20 min. To ensure that mice consumed the jellies consistently, all mice were initially trained to eat jellies without drug for 5 days prior to drug/vehicle jelly administration. Mice in this group underwent behavioral testing for cocaine CPP as described above 2 weeks into chronic drug administration. Drug administrations were continued until sacrifice at 4 weeks following the start of drug/vehicle administration.

Whole-Cell Electrophysiology:

Ex vivo mouse sagittal brain slices were prepared as previously described (Grueter, B. A., et al. Nat Neurosci 13:1519-1525 (2010)). Briefly, mice were acutely anesthetized using isoflurane and sacrificed by rapid decapitation. Brains were submerged in ice-cold sucrose dissecting solution (80 mM NaCl, 2.5 mM KCl, 7 mM MgCl2, 0.5 mM CaCl2, 1.25 mM NaH2PO4, 25 mM NaHCO3, 75 mM sucrose, and 25 mM glucose) and 250 µm thick slices were cut using the Leica 200VT Vibratome. Slices were allowed to recover for 10-15 min at 35° C. in an N-methyl D-glucamine (NMDG) based recovery solution (2.5 mM KCl, 20 mM HEPES, 1.2 mM NaH2PO4, 25 mM glucose, 93 mM NMDG, 30 mM NaHCO3, 5 mM sodium ascorbate, 3 mM sodium pyruvate, 10 mM MgSO4, and 0.5 mM CaCl2) before being transferred to a room temperature ACSF holding chamber for one hour prior to use. ASCF used for holding chamber and recordings contained 120 mM NaCl, 2.5 mM KCL, 1.5 mM MgCl2, 2.5 mM CaCl2, 1 mM NaH2PO4, 25 mM NaHCO3, and 10 mM glucose. The nucleus accumbens shell was identified by the shape of the anterior commissure, the corpus callosum, and the absence of stria in the brain slice. Accumbens shell medium spiny neurons were patched using the Scientifica Patch Star system and 4-7 MC/glass micropipettes made using the Sutter Brown/Fleming P1000 Micropipette Puller. Patch pipettes were filled with a cesium-based internal solution (120 mM CsMeSO3, 15 mM CsCl, 8 mM NaCl, 10 mM HEPES, 0.2 mM EGTA, 10 mM TEA-Cl, 4 mM ATP, 0.3 mM GTP, 0.1 mM spermine, and 5 mM QX-314 bromide). Evoked responses were elicited by electrical stimulation via the Iso-flex stimulation isolator and recorded using the Axopatch Multiclamp 700B amplifier and Axon Digidata 1550 low-noise data acquisition digitizer. All recordings were performed in 50 µM picrotoxin to isolate excitatory events and cells with an access resistance greater than 20 MΩ or those in which the access resistance changed greater than 20% during recording of a single experiment were excluded from analysis. For measurements of EPSC amplitude in the presence of OCA, OCA (Adipogen) stock aliquots in DMSO were diluted 1:1000 in ACSF (final concentration: 50 µM). OCA-containing ACSF was perfused into the recording chamber for 10 min following baseline acquisition while holding at −70 mV. Peak EPSC amplitude was measured for the duration of the experiment and normalized to the first 10 min. Analysis was performed by averaging six sweeps of identical interstimulus intervals and dividing the mean amplitude of the second event by the initial.

Cecal Content Sampling and Microbiota Analysis:

Cecal content samples were collected from GB-D and GB-IL mice at sacrifice 4-5 weeks after surgery and stored at −80° C. The DNA extractions, amplification, library prep, and sequencing were done by the Gut Microbiome Core, at the University of California at Davis. The 16S universal Eubacteria primers (PCR primers 515/806) were used to amplify the V4 variable region. A single-step 30 cycle PCR using HotStarTaq Plus Master Mix Kit (Qiagen, Valencia, Calif.) were used under the following conditions: 94° C. for 3 min, followed by 28 cycles of 94° C. for 30 seconds; 53° C. for 40 seconds and 72° C. for 1 min; after which a final elongation step at 72° C. for 5 min was performed. Following PCR, all amplicon products from different samples were mixed in equal concentrations and purified using Agencourt Ampure beads (Agencourt Bioscience Corporation, MA). Microbial sequencing was analyzed by bacterial tag encoded FLX amplicon pyrosequencing (bTEFAP) using a Roche 454 pyrosequencer and titanium reagents and 3-5K nominal sequences per sample of high quality extracted DNA. Sequences were depleted of barcodes and primers, then short sequences <200 base pairs are removed, sequences with >1 ambiguous base calls removed, and sequences with homopolymer runs exceeding 6 base pairs removed using the statistical software package Quantitative Insights Into Microbial Ecology (QIIME). A total number of 491,009 sequences passed a quality filter with a minimum score of 25 and an average length of 460 base pairs. Operational taxonomic units were defined after removal of chimeric and singleton sequences, clustering at 3% divergence (97% similarity). 24 OTUs were then taxonomically classified using BLASTn against a curated GreenGenes database.

Statistical Analysis:

Data are presented as means±standard error of the mean. Statistical analysis was performed with GraphPad Prism software, version 5.02 (GraphPad Software, San Diego, Calif.). Data were analyzed by statistical tests noted in figure legends, which included Student's t test, multiple t test, two-way RM ANOVA, and linear regression functions through Prism as appropriate. Outliers were defined as having values outside of quartile 1-1.5×interquartile range (IQR) and quartile3+1.5×IQR and were excluded. A p-value <0.05 defined statistical significance for all tests except for multiple t test analysis which determined significance with a false discovery rate of 1%.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

---

What is claimed is:

1. A method for treating addiction to a dopaminergic psychostimulant in a subject, comprising administering to the subject a therapeutically effective amount of a composition comprising a bile acid receptor agonist; wherein the bile acid receptor agonist comprises obeticholic acid (OCA).

2. The method of claim 1, wherein the bile acid receptor agonist is a synthetic bile acid receptor agonist.

3. The method of claim 1, wherein the bile acid receptor agonist is administered daily for at least 1 week.

4. The method of claim 1, wherein the dopaminergic psychostimulant is selected from the group consisting of cocaine, ketamine, methylenedioxypyrovalerone (MDPV), naphyrone, and Phencyclidine (PCP), amphetamine, methamphetamine, 3,4-methylenedioxymethamphetamine (MDMA), cathinone, methcathinone, mephedrone, methylone, methylphenidate (Ritalin, Metadate, Concerta), dexmethylphenidate (Focalin), dextroamphetamine (Dexedrine), mixed amphetamine salts (Adderall), dextromethamphetamine (Desoxyn), and lisdexamfetamine (Vyvanse).

* * * * *

UNITED STATES PATENT AND TRADEMARK OFFICE
CERTIFICATE OF CORRECTION

PATENT NO. : 10,064,876 B2
APPLICATION NO. : 15/218976
DATED : September 4, 2018
INVENTOR(S) : Aurelio Galli et al.

It is certified that error appears in the above-identified patent and that said Letters Patent is hereby corrected as shown below:

In the Specification

Column 1, under STATEMENT REGARDING FEDERALLY SPONSORED RESEARCH:
Line 15 - "Grant No. DK096527" should read "grant numbers GDA013975, DA036940 and DK105847".
Line 16 - "The Government has certain rights to the" should read "The government has certain rights in the".

Signed and Sealed this
Fifth Day of May, 2020

Andrei Iancu
*Director of the United States Patent and Trademark Office*